United States Patent
Borodic

(10) Patent No.: US 7,691,394 B2
(45) Date of Patent: *Apr. 6, 2010

(54) HIGH-POTENCY BOTULINUM TOXIN FORMULATIONS

(75) Inventor: Gary E. Borodic, Canton, MA (US)

(73) Assignee: Botulinum Toxin Research Associates, Inc., Quincy, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/111,951

(22) Filed: Apr. 22, 2005

(65) Prior Publication Data

US 2006/0182767 A1    Aug. 17, 2006

Related U.S. Application Data

(63) Continuation-in-part of application No. 10/740,755, filed on Dec. 22, 2003, and a continuation-in-part of application No. 10/446,562, filed on May 28, 2003.

(60) Provisional application No. 60/435,901, filed on Dec. 20, 2002, provisional application No. 60/383,570, filed on May 28, 2002.

(51) Int. Cl.
   *A61K 38/38*    (2006.01)
(52) U.S. Cl. .............. 424/239.1; 424/184.1; 424/234.1; 424/247.1; 514/12
(58) Field of Classification Search .................. None
   See application file for complete search history.

(56) References Cited

U.S. PATENT DOCUMENTS

| | | | |
|---|---|---|---|
| 4,845,042 A | 7/1989 | Newman et al. | |
| 4,861,627 A | 8/1989 | Mathiowitz et al. | |
| 5,053,005 A * | 10/1991 | Borodic | 604/51 |
| 5,069,936 A | 12/1991 | Yen et al. | |
| 5,437,291 A | 8/1995 | Pasricha et al. | |
| 5,512,547 A * | 4/1996 | Johnson et al. | 514/21 |
| 5,562,907 A * | 10/1996 | Arnon | 424/236.1 |
| 5,576,468 A | 11/1996 | Lubowitz | |
| 5,670,484 A * | 9/1997 | Binder | 514/14 |
| 5,696,077 A | 12/1997 | Johnson et al. | |
| 5,714,468 A * | 2/1998 | Binder | 514/14 |
| 5,721,205 A * | 2/1998 | Barnabas et al. | 510/522 |
| 5,846,929 A | 12/1998 | Johnson et al. | |
| 5,939,070 A | 8/1999 | Johnson et al. | |
| 5,989,545 A | 11/1999 | Foster et al. | |
| 6,051,239 A | 4/2000 | Simpson et al. | |
| 6,087,327 A | 7/2000 | Pearce et al. | |
| 6,100,306 A | 8/2000 | Li et al. | |
| 6,203,794 B1 | 3/2001 | Dolly et al. | |
| 6,210,707 B1 | 4/2001 | Papahadjopoulos et al. | |
| 6,306,423 B1 * | 10/2001 | Donovan et al. | 424/423 |
| 6,312,706 B1 | 11/2001 | Lai et al. | |
| 6,312,708 B1 | 11/2001 | Donovan | |
| 6,383,509 B1 | 5/2002 | Donovan et al. | |
| 6,429,189 B1 | 8/2002 | Borodic | |
| 6,447,787 B1 | 9/2002 | Gassner et al. | |
| 6,461,617 B1 * | 10/2002 | Shone et al. | 424/236.1 |
| 6,579,847 B1 | 6/2003 | Unger | |
| 6,585,993 B2 | 7/2003 | Donovan et al. | |
| 6,620,617 B2 | 9/2003 | Mathiowitz et al. | |
| 7,022,329 B2 * | 4/2006 | Donovan | 424/239.1 |
| 7,140,371 B2 | 11/2006 | Hanin et al. | |
| 7,192,596 B2 * | 3/2007 | Shone et al. | 424/247.1 |
| 7,211,261 B1 | 5/2007 | Moyer et al. | |
| 7,238,357 B2 * | 7/2007 | Barron | 424/239.1 |
| 7,288,259 B2 * | 10/2007 | Sanders et al. | 424/239.1 |
| 2001/0043930 A1 | 11/2001 | Aoki et al. | |
| 2001/0053370 A1 * | 12/2001 | Donovan | 424/239.1 |
| 2002/0006905 A1 * | 1/2002 | Aoki et al. | 514/12 |
| 2002/0107199 A1 | 8/2002 | Walker | |
| 2002/0192239 A1 * | 12/2002 | Borodic et al. | 424/247.1 |

(Continued)

FOREIGN PATENT DOCUMENTS

WO    WO 94/00481    1/1994

(Continued)

OTHER PUBLICATIONS

Giorgio, Maria et al, The Lancet, vol. 352, Aug. 22, 1998, pp. 625.*

(Continued)

*Primary Examiner*—Robert B Mondesi
*Assistant Examiner*—Ginny Portner
(74) *Attorney, Agent, or Firm*—Milbank, Tweed, Hadley & McCloy LLP

(57) ABSTRACT

The present invention provides improved formulations of *botulinum* toxin that increase delivery of the *botulinum* toxin to neural and associated tissues and exhibit a higher specific neurotoxicity and higher potency (in $LD_{50}$ Units) than available formulations of *botulinum* toxins. These improved formulations enable physicians to treat a wide variety of pathological conditions with a lower toxin load that reduces the risk of inducing an immune response against the toxin and its associated proteins that may ultimately lead to the development of toxin resistance. These benefits are particularly important in the treatment of conditions that require high-dose or chronic administration of *botulinum* toxin. Additionally, the decreased in $LD_{50}$ Unit doses of inventive formulations allows for controlled administration limits diffusion. The present invention also provides methods of treating neuromuscular diseases and pain, using low-dose *botulinum* toxin.

107 Claims, 2 Drawing Sheets

U.S. PATENT DOCUMENTS

| | | | |
|---|---|---|---|
| 2002/0197279 A1* | 12/2002 | Aoki et al. | 424/239.1 |
| 2003/0054975 A1* | 3/2003 | Voet | 514/2 |
| 2003/0086899 A1 | 5/2003 | Jafari | |
| 2003/0108597 A1 | 6/2003 | Chancellor et al. | |
| 2003/0118598 A1 | 6/2003 | Hunt | |
| 2003/0138437 A1 | 7/2003 | Hunt | |
| 2003/0143249 A1* | 7/2003 | Lamb | 424/239.1 |
| 2003/0166238 A1* | 9/2003 | Shone et al. | 435/219 |
| 2003/0180289 A1* | 9/2003 | Foster et al. | 424/132.1 |
| 2004/0037853 A1 | 2/2004 | Borodic | |
| 2004/0071735 A1 | 4/2004 | Marchini et al. | |
| 2004/0082540 A1 | 4/2004 | Hermida Ochoa | |
| 2004/0126396 A1 | 7/2004 | Aoki et al. | |
| 2005/0112146 A1 | 5/2005 | Graham | |
| 2005/0142150 A1 | 6/2005 | Graham | |
| 2005/0208076 A1 | 9/2005 | Hunt | |
| 2005/0238663 A1 | 10/2005 | Hunt | |
| 2005/0238664 A1 | 10/2005 | Hunt | |
| 2005/0238667 A1* | 10/2005 | Hunt | 424/239.1 |
| 2006/0269575 A1 | 11/2006 | Hunt | |
| 2007/0020294 A1 | 1/2007 | Marchini et al. | |
| 2007/0026019 A1 | 2/2007 | Hunt | |

FOREIGN PATENT DOCUMENTS

| | | | |
|---|---|---|---|
| WO | WO 96/39166 | | 12/1996 |
| WO | WO 97/35604 | | 10/1997 |
| WO | 99/03483 | * | 1/1999 |
| WO | 00/15245 | * | 3/2000 |
| WO | 00/24419 | * | 5/2000 |
| WO | WO 00/24419 A1 | | 5/2000 |
| WO | WO 01/58472 A2 | | 8/2001 |
| WO | 03/041724 | * | 5/2003 |
| WO | WO 03/041724 A1 | | 5/2003 |
| WO | WO 2004/060384 A2 | | 7/2004 |

OTHER PUBLICATIONS

O'Day, Justin, MD, Use of botulinum toxin in neruo-ophthalmology, 2001, vol. 12(6), pp. 419-422.*

Verheyden, Jean et al, Other noncosmetic uses of BOTOX, Seminars in Cutaneous Medicine and Surgery, vol. 20(2), Jun. 2001, pp. 121-126.*

European Neurology, vol. 43(1), pp. 9-12, Jan. 2000 (teaches a composition with 4000 ug albumin per 100 MU botulinum toxin). ( reference of record).*

Rollnik e tal (2000), reference of record.1.*

Bigalke et al (reference of record).*

Sesardic, et al, Biologicals, vol. 31, 2003, pp. 265-276.*

McIellan, K et al, Toxicon, vol. 34(9), pp. 975-985, 1996.*

Borodic, G et al, Neurology, vol. 46, pp. 26-29, 1996.*

Schmidt, James J et al, Journal of Protein Chemistry, vol. 16(1), 1997, Endoproteinase activity of Type A botulinum Neurotoxin, Substrate Requirements and activation by Serum Albumin.*

Bigalke et al, 2001.*

Rollnik et al, 1999.*

Borodic, "Botulinum A Toxin for (expressionistic) ptosis overcorrection after frontalis sling," Ophtalmic Plastic & Recostructive Surg. 8(2): 137-142, (1992).

Borodic et al. Botulinum A Toxin for the treatment of spasmodic torticollis, Dysphagia and Regional Toxin Spread. Head & Neck, 12: 392-398 (1990).

Nussgens et al. "Comparison of two botulinum-toxin preparations in the treatment of essential blepharospasm," Graefes Arch Clin Exp Ophthalmol 235(4): 197-199 (1997).

Bigalke et al. Botulinum A Toxin: DYSPORT improvement of biological availability,: Exp. Neurol. 168(1): 162-170 (2001).

Lew et al. "Botulinum toxin type B: a double-blind, placebo-controlled, safety and efficacy study in cervical dystonia," Neurology 49(3): 701-707 (1997).

Borodic et al "Botulinum Toxin: Clinical and Scientific Aspects." Ophthalmology Clinics of North America 4: 491-503 (1991).

Borodic et al. "Botulinum: a toxin for spasmodic torticollis, multiple vs single point injections per muscle," Head and Neck 14:33-37 (1992).

Ranoux et al. "Respective potencies of DYSPORT and BOTOX: a double blind, randomized, crossover study in cervical dystonia," J. Neuro. Neurosurg. Psychiatry 72: 459-462 (2002).

Borodic et al. "Butolinum toxin therapy, immunologic resistance, and problems with available materials," Neurology 996; 46:26-29.

Borodic et al "Botulinum B Toxin as an Alternative to Botulinum A Toxin, A Histologic study," Ophthalmic Plastic and Reconstructive Surgery 9(3): 182-190 (1993).

Journal of Clin Anesth. 11(7): 615-6.

Borodic et al. "Botulinum A Toxin for Treatment of Aberrant Facial Nerve Regeneration," Plastic and Reconstructive Surger, (91)6: 1042-1045, 1993.

Schantz, Edward J. et al. "Standardized Assay for *Clostridium botulinum* Toxins," Journal of the AOAC, vol. 61, No. 1, 1978.

Rollnik, J. et al., "Low-Dose Treatment of Cervical Dystonia, Blepharospasm and Facial Hemispasm with Albumin-Diluted Botulinum Toxin Type A Under EMG Guidance", Eur Neurol 2000; 43:9-12.

Goodnough, M. et al., "Stabilization of Botulinum Toxin Type A during Lyophilization," Allied and Environmental Microbiologu, Oct. 1992, p. 3426-3428.

Gassner, H. et al., "Addition of an Anesthetic Agent to Enhance the Predictability of the Effects of Botulinum Toxin Type A Injections: A Randomized Controlled Study", Mayo Clin Proc, Jul. 2000, vol. 75.

Johnson, M. et al., "The Use of a Water-Soluble Carbodiimide as a Coupling. Reagent in the Passive Hemagglutination Test", The Journal of Immunology, vol. 97, No. 6.

Langhein, C. et al., "Antibody response to bacterial antigens covalently bound to biodegradable polymerized serum albumin beads", Journal of Applied Bacteriology 1987, 63, 443-448.

International Search Report for PCT No. PCT/IB03/06145 dated Aug. 11, 2005.

Epinephrine package insert #58-6165, Abbott Laboratories, pp. 1-5, May 2000.

Botox package insert Allergan Pharmaceuticals, pp. 1-4.

International Search Report and Written Opinion for PCT/US2006/015459 dated Mar. 1, 2007.

Allergan, Inc. Botox® Product Insert, Revised Oct. 2004, 1-4, U.S.A.

Rollnik, Jens D., et al., "Low-Dose Treatment of Cervical Dystonia, Blepharospasm and Facial Hemispan with Albumin-Diluted Botulinum Toxin Type A under EMG Guidance", European Neurology vol. 43, 2000, pp. 9-12.

Communication pursuant to Article 96(2) EPC for 03 814 518.1-2107 dated Sep. 4, 2006.

Notice of References Cited mailed May 14, 2007 in U.S. Appl. No. 10/740,755.

Borodic, Gary et al., "Botulinum Toxin for Aberrant Facial Nerve Regeneration: Double-Blind, Placebo-Controlled Trial Using Subjective Endpoints", Face Nerve Regeneration, vol. 116, No. 1, Jul. 2005.

Pearce, L. Bruce et al., "The Median Paralysis Unit: A More Pharmacologically Relevant Unit of Biologic Activity for Botulinum Toxin", Toxicon, vol. 33, No. 2, pp. 217-227, 1995.

Wohlfarth, Kai et al., "Pharmacokinetic Properties of Different Formulations of Botulinum Neurotoxin Type A", Movement Disorders, vol. 19, Suppl. 8, 2004, pp. S65-S67.

Pearce, L. Bruce et al., "Review Article: Pharmacologic Characterization of Botulinum Toxin for Basic Science and Medicine", Toxicon, vol. 35, No. 9, pp. 1373-1412, 1997.

Abstract, Wholfarth, Kai et al., "Pharmacokinetic Properties of Different Formulations of Botulinum Neurotoxin Type A" Naunyn—Schmiedeberg Archives of Pharmacology (2002).

Borodic, Gary E. et al., "New Concepts in Botulinum Toxin Therapy", Drug Safety 11 (3): 145-152, 1994.

Marchetti, Albert. et al., "Retrospective Evaluation of the Dose of Dysport and BOTOX in the Management of Cervical Dystonia and Blepharospasm: The Real Dose Study," Movement Disorders, vol. 20, No. 8, 2005, pp. 937-944.

* cited by examiner

HIGH-POTENCY BOTULINUM TOXIN FORMULATIONS

This application is a continuation-in-part of U.S. patent application Ser. No. 10/740,755, filed Dec. 22, 2003, which claims benefit to U.S. Provisional Application Ser. No. 60/435,901, filed on Dec. 20, 2002, both of which are hereby incorporated by reference herein in their entirety. This application is also a continuation-in-part of U.S. patent application Ser. No. 10/446,562, filed on May 28, 2003, which claims benefit to U.S. Provisional Application Ser. No. 60/383,570, filed on May 28, 2002, both of which are hereby incorporated by reference herein in their entirety.

TECHNICAL FIELD OF THE INVENTION

This invention relates to pharmaceutical formulations of *botulinum* neurotoxin that have high specific neurotoxicity and that allow the therapeutically effective use of fewer $LD_{50}$ Units in clinical applications. The invention further relates to methods for the treatment of a variety of neuromuscular diseases, pain, inflammatory and cutaneous disorders with low-dose neurotoxin formulations based both on the delivery of reduced mass of neurotoxin and lower $LD_{50}$ Units.

BACKGROUND OF THE INVENTION

A. *Botulinum* Toxin: Mechanism of Action

*Botulinum* neurotoxin is a toxin isolated from a strain of *Clostridium botulinum*, that acts at the neuromuscular junction by inhibiting release of acetylcholine. *Botulinum* toxin is initially formed as a single-chain polypeptide that is cleaved to form a light chain that is bound to a heavy chain through a disulfide bond. The denervating effect of *botulinum* toxin occurs through: 1) the binding of the heavy chain to high-affinity receptors at the presynaptic terminal; 2) internalization of *botulinum* toxin through endocytosis; 3) translocation of the light chain into the cytoplasm of the nerve terminal; and 4) the endo-metalloprotease activity of the light chain (zinc cofactor) cleaves specific synaptic proteins that inhibit fusion of synaptic vesicles with the presynaptic membrane, thereby inhibiting the release of acetylcholine contained in the vesicles. Absent acetylcholine, the muscle does not receive the necessary signal for the muscle to contract. Subsequent to injection, neurogenic muscular atrophy ensues after several weeks.

B. *Botulinum* Toxin: Clinical Applications

A deadly toxin at high concentrations and quantities, *botulinum* toxin has been used as a valuable therapeutic for the treatment of many neuromuscular diseases (e.g., dystonia, hemifacial spasm, bruxism, spasticity, cerebral palsy, torticollis), as well as sensory disorders and cutaneous disorders (myofascial pain, migraine, tension headaches, neuropathy, hyperhydrosis), and in the treatment of disorders involving inflammation. The therapeutic value of *botulinum* toxin in its ability to produce local regional denervation of specific muscles and tissues.

The action of *botulinum* toxin on nerve terminals is irreversible. Axon sprouting, however, reverses the denervating effects of the toxin within two to six months. Consequently, a variety of conditions and disorders require repeated administration of the neurotoxin. Resistance to *botulinum* toxin is an important clinical consequence and problem resulting from repeated administration of *botulinum* toxin and the production of neutralizing antibodies. (Naumann et al. (1998) *J. Neurol. Neurosurg. Psychiatry* 65: 924-927; Hauna et al. (1998) *J. Neurol. Neurosurg. Psychiatry* 66: 612-616). The problem is most noted in high-dose applications such as cervical dystonia, however, immunity and resistance to the *botulinum* neurotoxin may occur with lower dose applications such as blepharospasm. Recently, the inventor observed that resistance can occur even with low-dose cosmetic applications, such as the treatment of facial rhytides. Accordingly, it is an object of the present invention to provide high-potency formulations and corresponding methods that reduce the likelihood of neutralizing antibodies in subjects treated with *botulinum* toxin.

The antigenicity of *botulinum* toxin stimulates antibody formation that reduces and most often completely obliterates the therapeutic effectiveness of botulinum-neurotoxin-based pharmaceuticals and may ultimately lead to abandonment of *botulinum* therapy. Several strategies to minimize the development of resistance have been directed toward reducing the antigenicity of the *botulinum* neurotoxin itself. For example, pegylated *botulinum* toxin (*botulinum* toxin covalently coupled to polyethylene glycol) have been developed for the treatment of neuromuscular disorders. Pegylation of the toxin is site directed thereby reducing antigenicity without interfering with neurotoxic effect. (See, U.S. Patent Publication No. 20020197278). Also, hybrid-toxin molecules with reduced antigenicity have been synthesized using the targeting and internalization portion (heavy chain) of one toxin serotype and the catalytic portion of a different serotype (light chain). The hybrid-toxin molecules exhibit reduced antigenicity but retain the inherent-binding specificity of the *botulinal*-heavy chain from the first serotype and the catalytic potency of the light chain from the second serotype. (See, U.S. Pat. No. 6,444,209).

Reduced antigenicity may also be achieved by further purifying the neurotoxin by reducing the antigenic complex proteins and other *clostridial* proteins associated with the toxin. (See, U.S. Pat. Nos. 5,756,468 and 5,512,547). Type A neurotoxin produced by *C. botulinum* is present as part of a complex of at least seven different noncovalently bound proteins. These nontoxic proteins range in size from about 17 to 118 kD. and are associated with the neurotoxin that has a molecular weight of about 147 kD. (Goodnough et al. (1993) *Appl. Environ. Microbiol.* 59: 2339-2342; Gimenez et al. (1993) *Protein Chem.* 12: 349-361; DasGupta (1980) *Canad. J. Microbiol.* 26: 992-997). Some of the non-toxic proteins associated with the various toxin complexes have hemagglutinating abilities (Sugiyama (1980) *Microbiol. Rev.* 44: 419-448; Somers et al. (1991) *J. Protein Chem.* 10:415-425). In particular, non-neurotoxic fractions of the L complexes of type A, B, C, and D have been shown to have hemagglutinating activity. Hemagglutinin fractions isolated from the different serotypes show some serological cross-reactivity. Non-toxic fractions from type A and B serotypes cross-react (Goodnough and Johnson (1993) *Appl. Environ. Microbiol.* 59: 2339-2342) as do non-toxic fractions from types E and F. The non-toxic fractions of types $C_1$ and D are antigenically identical as determined by Ouchterlony diffusion (Sakaguchi et al. (1974) *Jpn. J. Med. Sci. Biol.* 27: 161-170). By removing these proteins, more neurotoxin may be delivered to a therapeutic site with less antigenic proteins that may lead to the production of neutralizing antibodies.

C. Complications Associated with Conventional *Botulinum*-Toxin Formulations.

Substantial differences in the complication rate have also been noted at therapeutic quantities of different *botulinum* preparations. Side effects such as those resulting from diffusion of the *botulinum* toxin from the site of administration appear to be dependent on the formulation of *botulinum* toxin. For instance, dysphagia rates (difficulty swallowing) is a well-known complication of *botulinum* toxin administration when used for the treatment of cervical dystonia. (Borodic et al. (1990) Botulinum A toxin for the treatment of spasmodic torticollis. *Dysphagia and Regional Toxin Spread. Head & Neck*, 12: 392-398; incorporated herein by reference in its entirety). Differences in the rate of this complication between various formulations has been well appreciated when reviewing prior art literature between 1984-1995. Furthermore differences in the rate of ptosis (drooping eyelid) have been reported when comparing various immunotypes and different preparations of the same immunotype (see Table 1). It has become well accepted that this complication is the result of diffusion of *botulinum* toxin away from the injections sites, a property which is in conflict with the clinical goal of containing the denervating or biologic effect to a specific target region. The formulations and methods disclosed herein contain the biologic effect of the neurotoxin to a targeted anatomic region and thereby reduce the diffusion potential of the *botulinum* toxin pharmaceutical and decrease the associated side effects.

TABLE 2

Diffusion-related complications between various pharmaceutical formulations of botulinum toxin.

| Complication | BOTOX ® | DYSPORT ®[2] | MYOBLOC ®[3] |
|---|---|---|---|
| Ptosis[1] | <2% | 12-15% | 30-40% |
| Dysphagia | <2% | 14-21% | 10-17% |

[1]Nussgens et al. (1997) Comparison of two botulinum-toxin preparations in the treatment of essential blepharospasm. Graefes Arch Clin Exp Ophthalmol 235(4): 197-199.
[2]Phase 3 Studies 1998-1989 for Oculinum Meta-analysis of clinical studies on Dysphagia and Botulinum 1995 at NIH (Borodic).
[3]Lew et al. (1997) Botulinum toxin type B: a double-blind, placebo-controlled, safety and efficacy study in cervical dystonia. Neurology 49(3): 701-707.

In 1991, Borodic et al. developed a histologic model demonstrating a histochemical and morphologic diffusion gradient from point injections of *botulinum* toxin. (Borodic et al. (1991) Botulinum toxin: Clinical and scientific aspects. *Opthamology Clinics of North America* 4: 491-503; incorporated herein by reference in its entirety). The gradient was dose dependent over single muscle strips and capable of crossing fascial planes. The diffusion model was further demonstrated on the facial wrinkling pattern of the human forehead. (Borodic et al (1992) Botulinum toxin for spasmodic torticollis, multiple vs single point injections per muscle. *Head and Neck* 14: 33-37). Diffusion was thereafter used to explain the mechanism for dysphagia after surface injections of *botulinum* injection for the human neck and ptosis (drooping eyelid) after periocular injections for the treatment of essential blepharospasm. Ptosis results from diffusion of neuromuscular blocking activity from the lid edge to the muscular portion of the upper eyelid retractor, which lies in the upper orbital space. Dysphagia results from diffusion of neuromuscular weakening effect from the sternomastoid muscle, targeted for treatment of torticollis, to the peripharygeal musculature which generates the force for effective swallowing. From both histologic models and clinical experience, diffusion appears directly related to the quantity of toxin (in $LD_{50}$ units) administered. Consequently, the greater the quantity of toxin used as an injection in units used, the greater the diffusion from that point. A review of the scientific literature from the 1980's and early 1990's reveals that dysphagia is more commonly with observed with DYSPORT® than BOTOX®.

Recently, from studies done at European centers, the differences in dysphagia rates have been confirmed (Ranoux et al. (2002) Respective potencies of DYSPORT® and BOTOX®: a double blind, randomized, crossover study in cervical dystonia. *J. Neurol. Neurosurg. Psychiatry* 72: 459-462). Differences in ptosis rates for the treatment of blepharospasm have also been observed comparing BOTOX®. Ptosis is less frequently observed with BOTOX® (Nussgens et al. (1997) Comparison of two *botulinum*-toxin preparations in the treatment of essential Blepharospasm. *Graefes Arch Clin Exp Ophthalmol.* 235(4): 197-199). Major differences in the ptosis complication have also been reported when using *botulinum* toxin type B for the treatment of glabellar and forehead wrinkles when compared to *botulinum* type A (BOTOX®). (Holck et al. Comparison of High Dose *Botulinum* Toxin Type B to *Botulinum* Type A in the Treatment of Lateral Canthal Rhytides American Society of Ophthalmic Plastic and reconstructive Surgeons Annual Meeting, Anaheim, Calif. Nov. 14, 2003).

Prior to this invention, the in vivo binding of sequestration agents, such as albumin, to *botulinum* toxin has never been identified as important to clinical effectiveness of *botulinum*-toxin-based pharmaceuticals. By enhancing regional sequestration of the neurotoxin and facilitating saturation of neurotoxin receptors on neural tissues, high-concentration-albumin formulations improve the clinical effectiveness of *botulinum* toxin and reduce side effects such as those resulting from diffusion of the *botulinum* toxin from the site of administration. There has been no prior suggestion that increasing the albumin concentration, for example, relative to the neurotoxin, could enhance the effectiveness for the treatment of human disease. The existing *botulinum* toxin preparations currently available for clinical practice are BOTOX®, DYSPORT®, and MYOBLOC®. The present invention identifies the mechanism and provides compositions of improved utility of *botulinum*-toxin-based pharmaceuticals by increasing the concentration of a sequestration agent and other viscous agents to enhance sequestration and improve the effectiveness where other available *botulinum* toxin preparations have failed.

D. Sequestration.

Albumin was initially used to formulate *botulinum*-toxin-based pharmaceuticals because of its stabilizing effect on the biologic activity of the neurotoxin at high dilutions (see Schantz, *Botulinum* Toxin Therapy, Marcel Dekker 1994). Dilution of the purified *botulinum* toxin crystals with physiologic saline or water would cause the biologic activity and pharmaceutical properties to be lost at high dilutions. Additionally, the albumin has been reported to help keep the neurotoxin molecule from binding to glass containers. During the pre-clinical development of BOTOX® or any other *botulinum* toxin prepared for pharmaceutical use, there was no appreciation for the importance of albumin in the formulation other than a dilution stabilizer and excipient to keep the neurotoxin from binding to glass.

BOTOX® and DYSPORT® are derived from different strains of *Clostridial* species. BOTOX® is derived from the Hall strain of *Clostridium botulinum* originally maintained by the University of Wisconsin, whereas DYSPORT® is derived from British Microbiology Collection. Immunologic cross reactivity exists between the products as both products were derived from immunotype A strains. Despite similar immunotypes, the clinical responses between BOTOX® and DYSPORT® may be explained by the differences in the excipients used in each formulation. The difference in human serum albumin concentrations between BOTOX® and DYSPORT® are outlined in Table 3.

TABLE 3

Human Serum Albumin content of various pharmaceutical formulations of botulinum toxin.

| Formulation | Albumin[1] | $LD_{50}/\mu g$ albumin |
|---|---|---|
| BOTOX ® | 500 µg | 0.2 |
| DYSPORT ® | 125 µg | 5.0 |

[1]Albumin is represented in mg per 100 $LD_{50}$ units of botulinum toxin. Other differences exist including the presence of stabilizing sugars, Lactose is used in DYSPORT ® and not used in BOTOX ®.

The albumin discrepancy between BOTOX® and DYSPORT® is almost identical to the difference in dose requirements observed between BOTOX® and DYSPORT® in multiple clinical studies. The correlation between the albumin ratio/clinical potency ratio is further strengthened by changes in pharmacologic properties of DYSPORT® when albumin is added to the vials using a mouse hemidiaphram animal model. Wohlfahrt et al. noted using this model that adding albumin to one vials of DYSPORT® brought biologic activity higher using the mouse hemi-diaphragm model. (Biglalke et al (2001) *Botulinum* A toxin: DYSPORT® improvement of biological availability. *Exp. Neurol.* 168(1): 162-170). The authors suggested the increased biologic activity resulted from increased stability as measured with the mouse $LD_{50}$ bioassay afforded by the albumin concentration increase. (Biglalke et al (2001) *Botulinum* A toxin: DYSPORT® improvement of biological availability. *Exp. Neurol.* 168(1): 162-170). The authors explained the differences of albumin on the $LD_{50}$ bioassay without reference to mechanism of action in tissues or pharmacologic-pharmacokinetic importance, that is, in vivo albumin binding, enhanced sequestration, and improvement in therapeutic effects. The same authors further observed in a rat-diaphragm preparation, that the addition of albumin to the BOTOX® preparation could not substantially increase regional denervative effects and did not advocate any changes in formulation. The findings of these researchers concluded that there was an effect of the albumin concentration on the $LD_{50}$ measurements, however, their work did not demonstrate any increased potency of BOTOX® on regional denervation or that DYSPORT® could be enhanced to give any greater denervation potency over BOTOX®. Their work was limited by the in vitro nature of their experiments, that is, using a non-blood-perfused-animal dissection of a motor nerve (phrenic nerve) and diaphragm muscle, which fails to accounts for dilutions and tissue fluid flow capable of washing injected toxin away from targeted tissue prior to binding with the nerve axon terminal receptors. The real time application requires an in vivo analysis of the effects of albumin on regional denervation as outlined in the following experiments. Their work did identify reasons for differences in $LD_{50}$ as measured by the mouse lethality assay. These workers, however, concluded that no improvements in potency or effectiveness could be made over existing BOTOX® preparation. (Hanover Germany International *Botulinum* Toxin Meeting 2002).

Differences in potency, issues relating diffusion and containment of the biologic effect, and the development of resistance are important in the pharmacology of *botulinum*-based pharmaceuticals. Described herein is a method for altering compositions of *botulinum* based pharmaceuticals to enhance potency, increase sequestration of the *botulinum* toxin and limit adverse effects of *botulinum*-based pharmaceuticals.

SUMMARY OF THE INVENTION

The present invention provides a pharmaceutical formulation comprising a *botulinum* neurotoxin and a sequestration agent present in an amount greater than about 500 micrograms per 100 $LD_{50}$ Units neurotoxin, wherein fewer $LD_{50}$ Units of said formulation are required to achieve a therapeutic response than a formulation comprising *botulinum* toxin and a sequestration agent present in an amount greater than about 500 micrograms per 100 $LD_{50}$ Units neurotoxin. In one embodiment, fewer $LD_{50}$ Units of the pharmaceutical formulation are required to achieve a reduction of glabellar lines than a formulation comprising *botulinum* toxin and a sequestration agent present in an amount greater than about 500 micrograms per 100 $LD_{50}$ Units neurotoxin. Although the reduction of glabellar lines may be assessed by any means accepted in the art, patient self-grading and assessment and physician-based photo-scale grading are preferred. In another embodiment, fewer $LD_{50}$ Units of the pharmaceutical formulation are required to reduce muscle contraction in cervical dystonia than a formulation comprising *botulinum* toxin and a sequestration agent present in an amount greater than about 500 micrograms per 100 $LD_{50}$ Units neurotoxin.

The pharmaceutical formulations of the present invention are comprised of *botulinum* toxin and a sequestration agent in an amount greater than about 500 micrograms per 100 $LD_{50}$ Units neurotoxin, wherein the *botulinum* toxin may be selected from any one or a combination of the various *botulinum* toxin immunotypes such as A, B, $C_1$, $C_2$, $C_3$, D, E, F and G. In a preferred embodiment, the *botulinum* neurotoxin is *botulinum* toxin type A. In a preferred embodiment, the sequestration agent is human serum albumin or hyaluronate. In a more preferred embodiment, the sequestration agent is human serum albumin. The pharmaceutical formulations of the present invention may further comprise a stabilization or stabilizing agent that stabilizes the activity of the *botulinum* neurotoxin. As used herein, "stabilization agent" or "stabilizing agent" means any agent that prolongs the biologic activity, or specifically the neurotoxicity of the *botulinum* neurotoxin, upon storage. In a preferred embodiment, the stabilization or stabilizing agent is a monosaccharide or disaccharide. In a more preferred embodiment, trehalose is the stabilization or stabilizing agent.

The pharmaceutical formulations of the present invention are comprised of *botulinum* toxin and a sequestration agent in an amount greater than about 500 micrograms per 100 $LD_{50}$ Units neurotoxin. Preferably, the sequestration agent is present in an amount greater than about 500 µg per 100 $LD_{50}$ Units neurotoxin, 550 µg per 100 $LD_{50}$ Units neurotoxin, 600 µg per 100 $LD_{50}$ Units neurotoxin, 650 µg per 100 $LD_{50}$ Units neurotoxin, 700 µg per 100 $LD_{50}$ Units neurotoxin, 750 µg per 100 $LD_{50}$ Units neurotoxin, 800 µg per 100 $LD_{50}$ Units neurotoxin, 850 µg per 100 $LD_{50}$ Units neurotoxin, 900 µg per 100 $LD_{50}$ Units neurotoxin, 950 µg per 100 $LD_{50}$ Units neurotoxin, 1000 µg per 100 $LD_{50}$ Units neurotoxin, 1100 µg per 100 $LD_{50}$ Units neurotoxin, 1200 µg per 100 $LD_{50}$ Units neurotoxin, 1300 µg per 100 $LD_{50}$ Units neurotoxin, 1400 µg per 100 $LD_{50}$ Units neurotoxin, 1500 µg per 100 $LD_{50}$ Units neurotoxin, 1600 µg per 100 $LD_{50}$ Units neurotoxin, 1700 µg per 100 $LD_{50}$ Units neurotoxin, 1800 µg per 100 $LD_{50}$ Units neurotoxin, 1900 µg per 100 $LD_{50}$ Units neurotoxin, 2000 µg per 100 $LD_{50}$ Units neurotoxin, 2250 µg per 100 $LD_{50}$ Units neurotoxin, 2500 µg per 100 $LD_{50}$ Units neurotoxin, 2750 µg per 100 $LD_{50}$ Units neurotoxin, 3000 µg per 100 $LD_{50}$ Units neurotoxin, 3250 μg per 100 $LD_{50}$ Units neurotoxin, 3500 μg per 100 $LD_{50}$ Units neurotoxin, 3750 μg per 100 $LD_{50}$ Units neurotoxin, 4000 μg per 100 $LD_{50}$ Units neurotoxin, 4250 μg per 100 $LD_{50}$ Units neurotoxin, 5000 μg per 100 $LD_{50}$ Units neurotoxin, 5250 μg per 100 $LD_{50}$ Units neurotoxin, 5500 μg per 100 $LD_{50}$ Units neurotoxin, 5750 μg per 100 $LD_{50}$ Units neurotoxin, 6000 μg per 100 $LD_{50}$ Units neurotoxin, 7000 μg per 100 $LD_{50}$ Units neurotoxin, 8000 μg per 100 $LD_{50}$ Units neurotoxin, 9000 μg per 100 $LD_{50}$ Units neurotoxin, or 10,000 μg per 100 $LD_{50}$ Units neurotoxin.

More preferably, the sequestration agent is present in an amount between about 500 and 750 μg per 100 $LD_{50}$ Units neurotoxin, about 750 and 1000 μg per 100 $LD_{50}$ Units neurotoxin, about 1000 and 1250 μg per 100 $LD_{50}$ Units neurotoxin, about 1250 and 1500 μg per 100 $LD_{50}$ Units neurotoxin, about 1500 and 1750 μg per 100 $LD_{50}$ Units neurotoxin, about 1750 and 2000 μg per 100 $LD_{50}$ Units neurotoxin, about 2000 and 2250 μg per 100 $LD_{50}$ Units neurotoxin, about 2250 and 2500 μg per 100 $LD_{50}$ Units neurotoxin, about 2500 and 2750 μg per 100 $LD_{50}$ Units neurotoxin, about 2750 and 3000 μg per 100 $LD_{50}$ Units neurotoxin, about 3000 and 3250 μg per 100 $LD_{50}$ Units neurotoxin, about 3250 and 3500 μg per 100 $LD_{50}$ Units neurotoxin, about 3500 and 3750 μg per 100 $LD_{50}$ Units neurotoxin, about 3750 and 4000 μg per 100 $LD_{50}$ Units neurotoxin, about 4000 and 4250 μg per 100 $LD_{50}$ Units neurotoxin, about 4250 and 4500 μg per 100 $LD_{50}$ Units neurotoxin, about 4500 and 4750 μg per 100 $LD_{50}$ Units neurotoxin, about 4750 and 5000 μg per 100 $LD_{50}$ Units neurotoxin, about 5000 and 5250 μg per 100 $LD_{50}$ Units neurotoxin, about 5250 and 5500 μg per 100 $LD_{50}$ Units neurotoxin, about 5500 and 5750 μg per 100 $LD_{50}$ Units neurotoxin, about 5750 and 6000 μg per 100 $LD_{50}$ Units neurotoxin, about 6000 and 6250 μg per 100 $LD_{50}$ Units neurotoxin, about 6250 and 6500 μg per 100 $LD_{50}$ Units neurotoxin, about 6500 and 6750 μg per 100 $LD_{50}$ Units neurotoxin, about 6750 and 7000 μg per 100 $LD_{50}$ Units neurotoxin, about 7000 and 7500 μg per 100 $LD_{50}$ Units neurotoxin, about 7500 and 7750 μg per 100 $LD_{50}$ Units neurotoxin, about 7750 and 8000 μg per 100 $LD_{50}$ Units neurotoxin, about 8000 and 8250 μg per 100 $LD_{50}$ Units neurotoxin, about 8250 and 8500 μg per 100 $LD_{50}$ Units neurotoxin, about 8500 and 8750 μg per 100 $LD_{50}$ Units neurotoxin, about 8750 and 9000 μg per 100 $LD_{50}$ Units neurotoxin, about 9000 and 9250 μg per 100 $LD_{50}$ Units neurotoxin, about 9250 and 9500 μg per 100 $LD_{50}$ Units neurotoxin, about 9500 and 9750 μg per 100 $LD_{50}$ Units neurotoxin, or about 9750 and 10,000 μg per 100 $LD_{50}$ Units neurotoxin.

The pharmaceutical formulations of the present invention are comprised of *botulinum* toxin and a sequestration agent in an amount greater than about 500 micrograms per 100 $LD_{50}$ Units neurotoxin, wherein the *botulinum* toxin may be of any purity, as described by specific activity or specific neurotoxicity. In a preferred embodiment, the *botulinum* toxin has a specific neurotoxicity of between about 20 and 250 Units/ng neurotoxin, about 50 and 250 Units/ng neurotoxin, about 80 and 250 Units/ng neurotoxin, about 90 and 250 Units/ng neurotoxin, about 100 and 250 Units/ng neurotoxin, about 150 and 250 Units/ng neurotoxin, or about 200 and 250 Units/ng neurotoxin. In a more preferred embodiment, the *botulinum* toxin has a specific neurotoxicity of about 20 Units/ng neurotoxin, 30 Units/ng neurotoxin, 40 Units/ng neurotoxin, 50 Units/ng neurotoxin, 60 Units/ng neurotoxin, 70 Units/ng neurotoxin, 80 Units/ng neurotoxin, 90 Units/ng neurotoxin, 100 Units/ng neurotoxin, 110 Units/ng neurotoxin, 120 Units/ng neurotoxin, 130 Units/ng neurotoxin, 140 Units/ng neurotoxin, 150 Units/ng neurotoxin, 160 Units/ng neurotoxin, 170 Units/ng neurotoxin, 180 Units/ng neurotoxin, 190 Units/ng neurotoxin, 200 Units/ng neurotoxin, 210 Units/ng neurotoxin, 220 Units/ng neurotoxin, 230 Units/ng neurotoxin, 240 Units/ng neurotoxin, or 250 Units/ng neurotoxin.

In another embodiment of the present invention, the pharmaceutical formulations are essentially free of salt. More preferably, the formulation contains less than about 0.9% salt.

In one embodiment of the present invention, the pharmaceutical formulations have a pH of between about 5.6 to 6.0, about 6.0 to 6.4, about 6.4 to 6.8, about 6.8 to 7.2, about 5.8 to 7.4, about 6 to 7.4, about 6.2 to 7.4, about 6.5 to 7.4, about 6.7 to 7.4, about 7 to 7.4, or about 7.2 to 7.4. Preferably, the pharmaceutical formulations have a pH of about 5.8, about 5.9, about 6.0, about 6.1, about 6.2, about 6.3, about 6.4, about 6.5, about 6.6, about 6.7, about 6.8, about 6.9, about 7.0, about 7. 1, about 7.2, about 7.3, or about 7.4.

The pharmaceutical formulations of the present invention may be administered by any means known in the art sufficient to deliver the *botulinum* toxin to the desired therapeutic target. Preferably, the pharmaceutical formulations are delivered by transmucosal administration, transcutaneous administration, intramuscular administration or topically. Preferably, the pharmaceutical formulations of the present invention are administered by injection.

The pharmaceutical formulations of the present invention may be used in any of the methods of treatment disclosed herein. According to the inventive methods described herein, the pharmaceutical formulations of the present invention may be administered as a single treatment or repeated periodically to provide multiple treatments.

The present invention also provides methods for muscle denervation comprising the step of administering any of the pharmaceutical formulations of the present invention to a subject in need thereof in an amount sufficient to produce local muscle denervation. In another embodiment, the pharmaceutical formulations are administered to the muscles of a head, face, eye, neck, back, or tissues overlying one or more nasal sinuses.

In another embodiment, the present invention provides methods treating neuromuscular diseases comprising the step of administering any of the pharmaceutical formulations of the present invention to a subject in need thereof in an amount sufficient to produce muscle weakness. In another embodiment, the neuromuscular disease is cervical dystonia, hemifacial spasm, bruxism, blepharospasm, strabismus, or muscle spasticity. In a preferred embodiment, the neuromuscular disease hemifacial spasm, cervical dystonia, blepharospasm, strabismus, or muscle spasticity.

In a preferred embodiment, the neuromuscular disease is hemifacial spasm. A subject suffering from hemifacial spasm preferably receives between about 1.5 to 15 Units per treatment of any of the pharmaceutical formulations of the present invention. More preferably, between about 1.5 to 3 Units, 1.5 to 5 Units, 1.5 to 7 Units, 1.5 to 10 Units, 1.5 to 12 Units, 1.5 to 15 Units, 5 to 10 Units, 5 to 15 Units, or 10 to 15 Units per treatment are administered to a patient with hemifacial spasm. Most preferably, about 1.5, about 2, about 2.5, about 3, about 3.5, about 4, about 4.5 about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, or about 15 Units per treatment are administered to a patient with hemifacial spasm. Dosages greater than 15 Units per treatment may also be administered to patients with hemifacial spasm to achieve a therapeutic response.

In a preferred embodiment, the neuromuscular disease is cervical dystonia. A subject suffering from cervical dystonia preferably receives between about 15 to 150 Units per treatment of any of the pharmaceutical formulations of the present invention. More preferably, between about 15 to 30 Units, 15 to 50 Units, 15 to 75 Units, 15 to 100 Units, 15, to 125 Units, 15 to 150 Units, 20 to 100 Units, 20 to 150 Units, or 100 to 150 Units per treatment are administered to a patient with cervical dystonia. Most preferably, about 15, about 20, about 25, about 30, about 35, about 40, about 45 about 50, about 55, about 60, about 65, about 70, about 75, about 80, about 85, about 90, about 95, about 100, about 105, about 110, about 115, about 120, about 125, about 130, about 135, about 140, about 145, or about 150 Units per treatment are administered to a patient with cervical dystonia. Dosages greater than 150 Units per treatment may also be administered to patients with cervical dystonia to achieve a therapeutic response.

In a preferred embodiment, the neuromuscular disease is blepharospasm. A subject suffering from blepharospasm preferably receives between about 1.5 to 20 Units per treatment of any of the pharmaceutical formulations of the present invention. More preferably, between about 1.5 to 5 Units, 1.5 to 7 Units, 1.5 to 10 Units, 1.5 to 12 Units, 1.5 to 15 Units, 1.5 to 17 Units, 2.0 to 5 Units, 2 to 10 Units, 2 to 15, 2 to 20, 5 to 10, 5 to 15, or 5 to 20 Units per treatment are administered to a patient with blepharospasm. Most preferably, about 1.5, about 2.0, about 2.5, about 3.0, about 3.5, about 4.0, about 4.5 about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, or about 20.0 Units per treatment are administered to a patient with blepharospasm. Dosages greater than 20 Units per treatment may also be administered to patients with blepharospasm to achieve a therapeutic response.

In a preferred embodiment, the neuromuscular disease is strabismus. A subject suffering from strabismus preferably receives between about 4 to 40 Units per treatment of any of the pharmaceutical formulations of the present invention. More preferably, between about 4 to 10 Units, 4 to 15 Units, 4 to 20 Units, 4 to 25 Units, 4 to 30 Units, 4 to 35 Units, 7 to 15 Units, 7 to 20 Units, 7 to 25, 7 to 30, 7 to 35, or 7 to 40 Units per treatment are administered to a patient with strabismus. Most preferably, about 4, about 5, about 7.5, about 10, about 12.5, about 15, about 17.5 about 20.0, about 22.5, about 25.0, about 27.5, about 30.0, about 32.5, about 35, about 37.5, or about 40 Units per treatment are administered to a patient with strabismus. Dosages greater than 40 Units per treatment may also be administered to patients with strabismus to achieve a therapeutic response.

In a preferred embodiment, the neuromuscular disease is muscle spasticity. A subject suffering from muscle spasticity preferably receives between about 20 to 200 Units per treatment of any of the pharmaceutical formulations of the present invention. More preferably, between about 20 to 30 Units, 20 to 40 Units, 20 to 60 Units, 20 to 80 Units, 20 to 100 Units, 20 to 125 Units, 20 to 150 Units, or 20 to 175 Units per treatment are administered to a patient with muscle spasticity. Most preferably, about 20, about 25, about 30, about 35, about 40, about 45 about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 Units per treatment are administered to a patient with muscle spasticity. Dosages greater than 200 Units per treatment may also be administered to patients with muscle spasticity to achieve a therapeutic response.

In another embodiment, the present invention provides methods for treating pain comprising the step of administering any of the pharmaceutical formulations of the present invention to a subject in need thereof in an amount sufficient to reduce pain. In another embodiment, the patient suffers from myofascial pain, migraine headache pain, tension headache pain, neuropathic pain, facial pain, lower-back pain, sinus-headache pain, pain associated with temporomandibular joint disease, pain associated with spasticity or cervical dystonia, post-surgical wound pain, or neuralgia.

In a preferred embodiment, the patient suffers from sinus-headache pain. A subject suffering from sinus-headache pain preferably receives between about 4 to 40 Units per treatment of any of the pharmaceutical formulations of the present invention. More preferably, between about 4 to 10 Units, 4 to 15 Units, 4 to 20 Units, 4 to 25 Units, 4 to 30 Units, 4 to 35 Units, 7 to 15 Units, 7 to 20 Units, 7 to 25, 7 to 30, 7 to 35, or 7 to 40 Units per treatment are administered to a patient suffering from sinus-headache pain. Most preferably, about 4, about 5, about 7.5, about 10, about 12.5, about 15, about 17.5 about 20.0, about 22.5, about 25.0, about 27.5, about 30.0, about 32.5, about 35, about 37.5, or about 40 Units per treatment are administered to a patient with sinus-headache pain. Dosages greater than 40 Units per treatment may also be administered to patients with sinus headache-pain to achieve a therapeutic response.

In a preferred embodiment, the patient suffers from facial pain. A subject suffering from facial pain preferably receives between about 4 to 40 Units per treatment of any of the pharmaceutical formulations of the present invention. More preferably, between about 4 to 10 Units, 4 to 15 Units, 4 to 20 Units, 4 to 25 Units, 4 to 30 Units, 4 to 35 Units 7 to 15 Units, 7 to 20 Units, 7 to 25, 7 to 30, 7 to 35, or 7 to 40 Units per treatment are administered to a patient suffering from facial pain. Most preferably, about 4, about 5, about 7.5, about 10, about 12.5, about 15, about 17.5 about 20.0, about 22.5, about 25.0, about 27.5, about 30.0, about 32.5, about 35, about 37.5, or about 40 Units per treatment are administered to a patient with facial pain. Dosages greater than 40 Units per treatment may also be administered to patients with facial pain to achieve a therapeutic response.

In a preferred embodiment, the patient suffers from myofascial pain. A subject suffering from myofascial pain preferably receives between about 5 to 100 Units per treatment of any of the pharmaceutical formulations of the present invention. More preferably, between about 5 to 10 Units, 5 to 20 Units, 5 to 30 Units, 5 to 40 Units, 5 to 50 Units, 5 to 60 Units, 5 to 70 Units, 5 to 80 Units, 5 to 90, 10 to 20, 10 to 30, 10 to 50 or 10 to 60, or 10 to 70, or 10 to 80, 10 to 90 or 10 to 100 Units per treatment are administered to a patient suffering from myofascial pain. Most preferably, about 5, about 10, about 15, about 20, about 25, about 30, about 35 about 40, about 45, about 50, about 55, about 60, about 65, about 70, about 75, about 80, about 85, about 90, about 95 or about 100 Units per treatment are administered to a patient with myofascial pain. Dosages greater than 100 Units per treatment may also be administered to patients with myofascial pain to achieve a therapeutic response.

In a preferred embodiment, the patient suffers from migraine-headache pain. A subject suffering from migraine-headache pain preferably receives between about 0.5 to 50 Units per treatment of any of the pharmaceutical formulations of the present invention. More preferably, between about 0.5 to 5 Units, 0.5 to 10 Units, 0.5 to 15 Units, 0.5 to 20 Units, 0.5 to 25 Units, 0.5 to 30 Units, 0.5 to 35 Units, 0.5 to 40 Units, 0.5 to 45, 0.5 to 50, 2 to 10, 2 to 20, 2 to 30, 2 to 40, or 2 to 50 Units per treatment are administered to a patient suffering from migraine-headache pain. Most preferably, about 0.5, about 1.0, about 1.5, about 2.0, about 2.5, about 3.0, about 3.5 about 4.0, about 4.5, about 5.0, about 5.5, about 6.0, about 6.5, about 7.0, about 7.5, about 8.0, about 8.5, about 9.0, about 9.5, about 10.0, about 12, about 15, about 17, about 20, about 22, about 25, about 27, about 30, about 32, about 35, about 37, about 40, about 42, about 45, about 47, or about 50 Units per treatment are administered to a patient with migraine-headache pain. Dosages greater than 50 Units per treatment may also be administered to patients with migraine-headache pain to achieve a therapeutic response.

In a preferred embodiment, the suffers from lower-back pain. A subject suffering from lower-back pain preferably receives between about 15 to 150 Units per treatment of any of the pharmaceutical formulations of the present invention. More preferably, between about 15 to 30 Units, 15 to 50 Units, 15 to 75 Units, 15 to 100 Units, 15 to 125 Units, 15 to 150 Units, 20 to 100 Units, 20 to 150 Units, or 100 to 150 Units per treatment are administered to a patient with lower-back pain. Most preferably, about 15, about 20, about 25, about 30, about 35, about 40, about 45 about 50, about 55, about 60, about 65, about 70, about 75, about 80, about 85, about 90, about 95, about 100, about 105, about 110, about 115, about 120, about 125, about 130, about 135, about 140, about 145, or about 150 Units per treatment are administered to a patient with lower-back pain. Dosages greater than 150 Units per treatment may also be administered to patients with lower-back pain to achieve a therapeutic response.

In a preferred embodiment, the patient suffers from tension-headache pain. A subject suffering from tension-headache pain preferably receives between about 5 to 50 Units per treatment of any of the pharmaceutical formulations of the present invention. More preferably, between about 5 to 10 Units, 5 to 15 Units, 5 to 20 Units, 5 to 25 Units, 5 to 30 Units, 5 to 35 Units, 5 to 40 Units, 5 to 45 Units, 10 to 20, 10 to 25, 10 to 30, 10 to 35, 10 to 40, 10 to 45, or 10 to 45 Units per treatment are administered to a patient with tension-headache pain. Most preferably, about 5, about 10, about 20; about 25, about 30, about 35, about 40, about 45, or about 50 Units per treatment are administered to a patient with tension-headache pain. Dosages greater than 50 Units per treatment may also be administered to patients with tension-headache pain to achieve a therapeutic response.

In a preferred embodiment, the patient suffers from sinus headache pain or facial pain associated with acute or recurrent chronic sinusitis. Preferably, any of the pharmaceutical formulations of the present invention may be administered to the nasal mucosa or to the subcutaneous structures overlying the sinuses, wherein the administration of the formulation reduces the headache and/or facial pain associated with acute recurrent or chronic sinusitis. More preferably, any of the pharmaceutical formulations of the present invention may be administered to the nasal mucosa. The subcutaneous structures overlying the sinuses preferably overly one or more of the sinuses selected from the group consisting of: ethmoid; maxillary; mastoid; frontal; and sphenoid. In another embodiment, subcutaneous structures overlying the sinuses lie within one or more of the areas selected from the group consisting of: forehead; malar; temporal; post auricular; and lip.

In another embodiment, a patient suffering from sinus headache pain or facial pain associated with acute or recurrent chronic sinusitis is treated by administering any of the pharmaceutical formulations of the present invention to an afflicted area of the patient. In a preferred embodiment, the pharmaceutical formulations disclosed herein are administered to the projections of a trigeminal nerve innervating a sinus.

Patients suffering from sinus headache pain or facial pain associated with acute or recurrent chronic sinusitis often exhibit symptoms including rhinitis, sinus hypersecretion and/or purulent nasal discharge. In one embodiment, the patients treated with the pharmaceutical formulations of the present invention exhibit symptoms of sinus hypersecretion and purulent nasal discharge.

The present invention also provides methods for treating a patient suffering from sinus headache pain or facial pain associated with acute or recurrent chronic sinusitis, wherein the subject suffers from neuralgia. Preferably, the neuralgia is trigeminal neuralgia. In another embodiment, the neuralgia is: associated with compressive forces on a sensory nerve; associated with intrinsic nerve damage, demyelinating disease, or a genetic disorder; associated with a metabolic disorder; associated with central neurologic vascular disease; or associated with trauma. In another embodiment of the present invention, the pain is associated with dental extraction or reconstruction.

In another embodiment, the present invention provides methods for cosmetically modifying soft-tissue features comprising the step of administering any of the pharmaceutical formulations of the present invention to a subject in need thereof in an amount sufficient to modify said features. In a preferred embodiment, the pharmaceutical formulation is administered via transcutaneous or transmucosal injection either at a single focus or multiple foci.

Preferably, the pharmaceutical formulations of the present invention are administered to the face or neck of the subject. In a preferred embodiment, the pharmaceutical formulations of the present invention are administered to the subject in an amount sufficient to reduce rhytides. Preferably, the formulation is administered between eyebrows of the subject in an amount sufficient to reduce vertical lines between the eyebrows and on a bridge of a nose. The pharmaceutical formulations may also be administered near either one or both eyes of the subject in an amount sufficient to reduce lines at corners of the eyes. In another embodiment, the pharmaceutical formulations of the present invention may also be administered to a forehead of the subject in an amount sufficient to reduce horizontal lines on said forehead. In yet another embodiment of the present invention the pharmaceutical formulation is administered to the neck of the subject in an amount sufficient to reduce muscle bands in the neck.

The present invention provides methods for reducing lip volume in one or both of the upper and lower lips of a patient. In one embodiment, the patient suffers from hypervolemic lip deformity. Preferably, the pharmaceutical formulations of the present invention are administered to a orbicularis oris muscle of the subject. The pharmaceutical *botulinum* toxin formulations of the present invention may also be administered to one or more lip retractor muscle. A patient desiring the cosmetic reduction of lip volume or other soft-tissue structure, or the patient suffering from hyper-volemic lip deformity preferably receives between about 2 to 20 Units per treatment of any of the pharmaceutical formulations of the present invention. More preferably, between about 2 to 5 Units, 2 to 7 Units, 2 to 10 Units, 2 to 12 Units, 2 to 15 Units, 2 to 20 Units, 5 to 10 Units, 5 to 15 Units, or 5 to 20 Units per treatment are administered to a patient desiring the cosmetic reduction of lip volume or other soft-tissue structure, or the patient suffering from hyper-volemic lip deformity. Most preferably, about 2, about 3, about 4, about 5, about 6, about 7, about 8 about 9, about 10, about 11, about 12, about 13, about 14, about 15, about 16, about 17, about 18, about 19 or about 20 Units per treatment are administered to a patient desiring the cosmetic reduction of lip volume or other soft-tissue structure, or the patient suffering from hyper-volemic lip deformity. Dosages greater than 20 Units per treatment may also be administered to patient desiring the cosmetic reduction of lip volume or other soft-tissue structure, or the patient suffering from hyper-volemic lip deformity to achieve a therapeutic response.

In another embodiment, the present invention provides methods for treating inflammation comprising the step of administering any of the pharmaceutical formulations of the present invention to a subject in need thereof in an amount sufficient to reduce inflammation. Preferably, the pharmaceutical formulations of the present invention are administered to a patient without producing muscle weakness. In one embodiment, the pharmaceutical formulations of the present invention are administered to patients with an inflammatory condition. Preferably, the inflammatory condition is neurogenic inflammation. In another embodiment, the subject suffers from rheumatoid arthritis or a gastro-intestinal inflammatory disease.

In a preferred embodiment, the patient suffers from an inflammatory disorder. A subject suffering from an inflammatory disorder preferably receives between about 1 to 100 Units per treatment of any of the pharmaceutical formulations of the present invention. More preferably, between about 1 to 10 Units, 1 to 20 Units, 1 to 30 Units, 1 to 40 Units, 1 to 50 Units, 1 to 60 Units, 1 to 70 Units, 1 to 80 Units, 1 to 90, 5 to 20, 5 to 30, 5 to 40, 5 to 50, 5 to 60, 5 to 70, 5 to 80, 5 to 90, or 5 to 100 Units per treatment are administered to a patient with an inflammatory disorder. Most preferably, about 1, about 10, about 20, about 30, about 40, about 50, about 60, about 70, about 80, about 90, or about 100 Units per treatment are administered to a patient with tension-headache pain. Dosages greater than 100 Units per treatment may also be administered to patients suffering from inflammation or an inflammatory disorder to achieve a therapeutic response.

In a preferred embodiment, the inflammatory disorder is blepharitis. A subject suffering from blepharitis preferably receives between about 1 to 10 Units per treatment of any of the pharmaceutical formulations of the present invention. More preferably, between about 1 to 3 Units, about 1 to 5 Units, about 1 to 7 Units, or 1 to 10 Units per treatment are administered to a patient with an inflammatory disorder. Most preferably, about 1, about 2, about 3, about 4, about 5, about 6, about 7, about 8, about 9, or about 10 Units per treatment are administered to a patient with tension-headache pain. Dosages greater than 10 Units per treatment may also be administered to patients suffering from inflammation or an inflammatory disorder to achieve a therapeutic response.

In a preferred embodiment, the inflammatory disorder is prostatitis. A subject suffering from prostatitis preferably receives between about 10 to 100 Units per treatment of any of the pharmaceutical formulations of the present invention. More preferably, between about 10 to 20 Units, about 10 to 30 Units, about 10 to 40 Units, about 10 to 50 Units, about 10 to 60 Units, about 10 to 70 Units, about 10 to 80 Units, or about 10 to 90 Units per treatment are administered to a patient with prostatitis. Most preferably, about 10, about 20, about 30, about 40, about 50, about 60, about 70, about 80, about 90, or about 100 Units per treatment are administered to a patient with prostatitis. Dosages greater than 100 Units per treatment may also be administered to patients with prostatitis to achieve a therapeutic response.

In another embodiment, the present invention provides methods for treating cutaneous disorders comprising the step of administering any of the pharmaceutical formulations of the present invention to a subject in need thereof in an amount sufficient to reduce a sebaceous or mucous secretion. Preferably, the pharmaceutical formulations of the present invention are administered to a patient without producing muscle weakness. In one embodiment, the pharmaceutical formulations of the present invention are administered to patients with chalazion or hordeola. Preferably, the pharmaceutical formulations of the present invention are injected into one or more sites of an eyelid or conjunctiva. In another embodiment, the formulations of the present invention are administered to a body surface. In another embodiment, the pharmaceutical formulations are administered in an amount sufficient to reduce cutaneous bacterial or fungal growth, including but not limited to *Staphylococcus; Streptococcus* and *Moraxella*. Preferably, the pharmaceutical formulations of the present invention are administered to an area selected from the group consisting of: eyelid; scalp; feet; groin; and armpit to reduce cutaneous infection.

In another embodiment, the cutaneous disorder is hyperhydrosis.

The present invention also provides methods for treating inflammation comprising the step of administering any of the pharmaceutical formulations of the present invention to a subject in need thereof in an amount sufficient to reduce inflammation. Preferably, the pharmaceutical formulations of the present invention are administered to a patient without producing muscle weakness. In one embodiment, the pharmaceutical formulations of the present invention are administered to patients with an inflammatory condition. Preferably, the inflammatory condition is neurogenic inflammation. In another embodiment, the subject suffers from rheumatoid arthritis or a gastrointestinal inflammatory disease.

In one embodiment, the present invention provides methods for treating cervical dystonia comprising the step of administering between 150 to 3500 picograms per treatment of a pharmaceutical formulation comprising a *botulinum* toxin to a subject in need thereof in an amount sufficient to produces local muscle weakness in said subject. A subject in need of muscle denervation preferably receives between about 150 to 300 picograms, about 150 to 400 picograms, about 150 to 500 picograms, about 150 to 750 picograms, about 150 to 1000 picograms, about 150 to 1250 picograms, about 150 to 1500 picograms, about 150 to 1750 picograms, about 150 to 2000 picograms, about 150 to 2250 picograms, about 150 to 2500 picograms, about 150 to 2750 picograms, about 150 to 3000 picograms, or about 150 to 3500 picograms of a pharmaceutical formulation comprising a *botulinum* toxin per treatment. Most preferably, about 150, about 250, about 350, about 450, about 550, about 650, about 750, about 850, about 950, about 1050, about 1150, about 1250, about 1350, about 1450, about 1550, about 1650, about 1750, about 1850, about 1950, about 2050, about 2150, about 2250, about 2350, about 2450, about 2550, about 2650, about 2750, about 2850, about 2950, about 3000, about 3100, about 3200, about 3300 about 3400 or about 3500 picograms per treatment are administered to a subject to produce muscle denervation. Dosages greater than 3500 picograms per treatment may also be administered to patients with cervical dystonia to achieve a therapeutic response.

The present invention also provides methods for treating blepharospasm comprising the step of administering between about 2.5 to 45 picograms per treatment of a pharmaceutical formulation comprising *botulinum* toxin to a subject in need thereof, wherein the administration of said *botulinum* toxin produces muscle weakness in said subject. A subject with blepharospasm preferably receives between about 2.5 to 5 picograms, about 2.5 to 7.5, about 2.5 to 10, about 2.5 to 12.5, about 2.5 to 15, about 2.5 to 17.5, about 2.5 to 20, about 2.5 to 25, about 2.5 to 30, about 2.5 to 35 about 2.5 to 40, about 2.5 to 45 picograms of a pharmaceutical formulation comprising *botulinum* per treatment. Most preferably, about 2.5, about 3.0, about 3.5, about 4.0, about 4.5, about 5.0, about 6.0, about 6.5, about 7.0 about 7.5, about 8.0, about 8.5, about 9.0 about 10, about 12, about 15, about 17, about 20, about 22, about 25, about 27, about 30, about 32, about 35, about 37, about 40, about 42, or about 45 picograms per treatment are administered to a subject to produce muscle weakness. Dosages greater than 45 picograms per treatment may also be administered to patients with blepharospasm to achieve a therapeutic response.

The present invention also provides methods for treating strabismus comprising the step of administering between about 2.5 to 45 picograms per treatment of a pharmaceutical formulation comprising a *botulinum* toxin to a subject in need thereof, wherein the administration of said *botulinum* toxin produces produce muscle weakness in said subject. A subject with strabismus preferably receives between about 2.5 to 5 picograms, about 2.5 to 7.5, about 2.5 to 10, about 2.5 to 12.5, about 2.5 to 15, about 2.5 to 17.5, about 2.5 to 20, about 2.5 to 25, about 2.5 to 30, about 2.5 to 35 about 2.5 to 40, about 2.5 to 45 picograms of a pharmaceutical formulation comprising *botulinum* toxin per treatment. Most preferably, about 2.5, about 3.0, about 3.5, about 4.0, about 4.5, about 5.0, about 6.0, about 6.5, about 7.0, about 7.5, about 8.0, about 8.5, about 9.0 about 10, about 12, about 15, about 17, about 20, about 22, about, 25, about 27, about 30, about 32, about 35, about 37, about 40, about 42, or about 45 picograms per treatment are administered to a subject to produce muscle weakness. Dosages greater than 45 picograms per treatment may also be administered to patients with strabismus to achieve a therapeutic response.

The present invention also provides methods for treating muscle spasticity comprising the step of administering between about 20 to 350 picograms per treatment of a pharmaceutical formulation comprising a *botulinum* toxin to a subject in need thereof, wherein the administration of said *botulinum* toxin produces produce muscle weakness in said subject. A subject with muscle spasticity preferably receives between about 20 to 30 picograms, about 20 to 40 picograms, about 20 to 50 picograms, about 20 to 60 picograms, about 20 to 70 picograms, about 20 to 80 picograms, about 20 to 90 picograms, about 20 to 100 picograms, about 20 to 150 picograms, about 20 to 200 picograms, about 20 to 250 picograms, about 20 to 300 or about 20 to 350 picograms of a pharmaceutical formulation comprising a *botulinum* toxin per treatment. Most preferably, about 20, about 30, about 40, about 50, about 60, about 70, about 80, about 90, about 100, about 110, about 120, about 130, about 140, about 150, about 160 about 170, about 180, about 190, about 200, about 210, about, 220, about 230, about 240, about 250, about 260, about 270, about 280, about 290, about 300, about 310, about 320, about 330, about 340, or about 350 picograms per treatment are administered to a subject to produce muscle weakness. Dosages greater than 350 picograms per treatment may also be administered to patients with muscle spasticity to achieve a therapeutic response.

In a preferred embodiment, the pharmaceutical formulation comprising a *botulinum* toxin is administered to a subject suffering muscle spasticity in the flexor digitorum profundus muscle or the flexor digitorum sublimus muscle.

In another embodiment between about 20 to 450 picograms per treatment of a pharmaceutical formulation comprising a *botulinum* toxin is administered to a subject suffering muscle spasticity to produce muscle weakness in the flexor carpii ulnaris muscle. Preferably between about 20 to 50 picograms, about 20 to 75 picograms, about 20 to 100 picograms, about 20 to 125 picograms, about 20 to 150 picograms, about 20 to 175 picograms, about 20 to 200 picograms, about 20 to 225 picograms, about 20 to 250 picograms, about 20 to 275 picograms, about 20 to 300 picograms, about 20 to 325 picograms, about 20 to 350 picograms, about 20 to 375 picograms, about 20 to 400 picograms, about 20 to 425 picograms, or about 20 to 450 picograms of a pharmaceutical formulation comprising a *botulinum* toxin are administered per treatment to a subject in need thereof. Most preferably, about 20, about 30, about 40, about 50, about 60, about 70, about 80, about 90, about 100, about 110, about 120, about 130, about 140, about 150, about 160 about 170, about 180, about 190, about 200, about 210, about, 220, about 230, about 240, about 250, about 260, about 270, about 280, about 290, about 300, about 310, about 320, about 330, about 340, about 350, about 360, about 370, about 380, about 390, about 400, about 410, about 420, about 430 about 440, or about 450 picograms per treatment are administered to a subject to produce muscle weakness in the flexor carpii ulnaris muscle. Dosages greater than 450 picograms per treatment may also be administered to patients with muscle spasticity to achieve a therapeutic response.

In another embodiment between about 35 to 725 picograms per treatment of the pharmaceutical formulation comprising a *botulinum* toxin is administered to a subject suffering muscle spasticity to produce muscle weakness in the flexor carpii radialis muscle. Preferably between about 35 to 50 picograms, about 35 to 75 picograms, about 35 to 100 picograms, about 35 to 125 picograms, about 35 to 150 picograms, about 35 to 175 picograms, about 0.35 to 200 picograms, about 35 to 225 picograms, about 35 to 250 picograms, about 35 to 275 picograms, about 35 to 300 picograms, about 35 to 325 picograms, about 35 to 350 picograms, about 35 to 375 picograms, about 35 to 400 picograms, about 35 to 425 picograms, about 35 to 450, about 35 to 475, about 35 to 500, about 35 to 525, about 35 to 550, about 35 to 575, about 35 to 600, about 35 to 625, about 35 to 650, about 35 to 675, about 35 to 700, about 35 to 725, or about 35 to 750, picograms of a pharmaceutical formulation comprising a *botulinum* toxin are administered per treatment to a subject in need thereof. Most preferably, about 35, about 45, about 55, about 65, about 75, about 85, about 95, about 100, about 110, about 120, about 130, about 140, about 150, about 160 about 170, about 180, about 190, about 200, about 210, about, 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, or about 725 picograms per treatment are administered to a subject to produce muscle weakness in the flexor carpii radialis muscle. Dosages greater than 725 picograms per treatment may also be administered to patients with muscle spasticity to achieve a therapeutic response.

In another embodiment between about 100 to 2250 picograms per treatment of the pharmaceutical formulation comprising a *botulinum* toxin, is administered to a subject suffering muscle spasticity to produce muscle weakness in the biceps brachii muscle. Preferably between about 100 to 125 picograms, about 100 to 150 picograms, about 100 to 175 picograms, about 100 to 200 picograms, about 100 to 250 picograms, about 100 to 300 picograms, about 100 to 350 picograms, about 100 to 400 picograms, about 100 to 450 picograms, about 100 to 500 picograms, about 100 to 600 picograms, about 100 to 700 picograms, about 100 to 800 picograms, about 100 to 900 picograms, about 100 to 1000 picograms, about 100 to 1100 picograms, about 100 to 1200 picograms, about 100 to 1300 picograms, about 100 to 1400 picograms, about 100 to 1500 picograms, about 100 to 1600 picograms, about 100 to 1700 picograms, about 100 to 1800 picograms, about 100 to 1900 picograms, about 100 to 2000 picograms, about 100 to 2100 picograms, or about 100 to 2250 picograms of a pharmaceutical formulation comprising a *botulinum* toxin is administered per treatment to a subject in need thereof. Most preferably, about 100, about 150, about 200, about 250, about 300, about 350, about 400, about 450, about 500, about 550, about 600, about 650, about 700, about 750 about 800, about 850, about 900, about 950, about 1000, about, 1050, about 1100, about 1150, about 1200, about 1250, about 1300, about 1350, about 1400, about 1450, about 1500, about 1550, about 1600, about 1650, about 1700, about 1750, about 1800, about 1850, about 1900, about 1950, about 2000, about 2050, about 2100, about 2150, about 2200, or about 2250 picograms per treatment are administered to a subject to produce muscle weakness in the biceps brachii muscle. Dosages greater than 2250 picograms per treatment may also be administered to patients with muscle spasticity to achieve a therapeutic response.

The present invention also provides methods for treating pain and pain syndromes comprising the step of administering between about 1.0 to 20 picograms per treatment of a pharmaceutical composition comprising a *botulinum* toxin to a subject in need thereof, wherein the administration of said *botulinum* toxin formulation reduces pain in said subject. Preferably, a patient suffering from pain or a pain syndrome receives between about 1 to 3, about 1 to 5, about 1 to 7, about 1 to 10, about 1 to 12, about 1 to 15, about 1 to 17, about 5 to 10, about 5 to 15, about 5 to 20, or about 1 to 20 picograms per treatment of a pharmaceutical composition comprising *botulinum* toxin. Most preferably, about 1, about, 2, about 3, about 4, about 5, about 6, about 7, about 8, about 9, about 10, about 11, about 12, about 13, about 14, about 15, about 16, about 17, about 18, about 19, or about 20 picograms per treatment are administered to a subject to reduce pain. Dosages greater than 20 picograms per treatment may also be administered to patients with muscle spasticity to achieve a therapeutic response.

The present invention also provides methods for cosmetically modifying soft-tissue features comprising the step of administering between about 5 to 70 picograms per treatment of a pharmaceutical formulation comprising a *botulinum* toxin to a subject in need thereof, wherein the administration of said *botulinum* toxin is sufficient to modify said features in said subject. Preferably, a patient desiring to modify soft tissue features receives between about 5 to 10, about 5 to 15, about 5 to 20, about 5 to 25, about 5 to 30, about 5 to 35, about 5 to 40, about 5 to 45, about 5 to 55, about 5 to 60, about 5 to 65 or about 5 to 75 picograms per treatment of a pharmaceutical composition comprising *botulinum* toxin. Most preferably, about 5, about 7, about 10, about 12, about 15, about 17, about 20, about 22, about 25, about 27, about 30, about 32, about 35, about 37, about 40, about 42, about 45, about 47, about 50, about 52, about 55, about 57, about 60, about 62, about 65, about 67, or about 70 picograms per treatment are administered to a subject to modify soft tissue features. Dosages greater than 70 picograms per treatment may also be administered to achieve a therapeutic response.

The present invention also provides methods for treating inflammation comprising the step of administering between about 1.0 to 20 picograms per treatment of a *botulinum* toxin to a subject in need thereof, wherein the administration of said *botulinum* toxin reduces inflammation in said subject. Preferably, a patient suffering from inflammation receives between about 1 to 2, about 1 to 5, about 1 to 7, about 1 to 10, about 1 to 12, about 1 to 15, about 1 to 17, or about 1 to 20 picograms per treatment of a pharmaceutical composition comprising a *botulinum* toxin. Most preferably, about 1, about 2, about 3, about 4, about 5, about 6, about 7, about 8, about 9, about 10, about 11, about 12, about 13, about 14, about 15, about 16, about 17, about 18, about 19, or about 20 picograms per treatment are administered to a subject to reduce inflammation. Dosages greater than 20 picograms per treatment may also be administered to reduce inflammation.

The present invention also provides methods of treating cutaneous disorders comprising the step of administering between about 1.0 to 10 picograms per treatment of a *botulinum* toxin to a subject in need thereof, wherein the administration of said *botulinum* toxin reduces a sebaceous, meibomian or mucous secretion in said subject. Preferably, a patient suffering from cutaneous disorders receives between about 1 to 2, about 1 to 3, about 1 to 4, about 1 to 5, about 1 to 6, about 1 to 7, about 1 to 8, about 1 to 9, or about 1 to 10 picograms per treatment of a pharmaceutical composition comprising a *botulinum* toxin. Most preferably, about 1, about 2, about 3, about 4, about 5, about 6, about 7, about 8, about 9, or about 10 picograms per treatment are administered to a subject to reduce a sebaceous, meibomian or mucous secretion. Dosages greater than 10 picograms per treatment may also be administered to reduce sebaceous, meibomian or mucous secretions.

The present invention also provides methods for producing a high-potency *botulinum* toxin formulation comprising the step of adding greater than about 500 micrograms of a sequestration agent per 100 $LD_{50}$ Units of a *botulinum* neurotoxin, wherein said formulation has an increased clinical potency. Preferably, greater than about 550, greater than about 600, greater than about 650, greater than about 700, greater than about 750, greater than about 800, greater than about 850, greater than about 900, greater than about 950, greater than about 1000, greater than about 1500, greater than about 2000, greater than about 2500, greater than about 3000, greater than about 3500, greater than about 4000, greater than about 4500, greater than about 5000, greater than about 5500, greater than about 6000, greater than about 6500, greater than about 7000, greater than about 7500, greater than about 8000, greater than about 8500, greater than about 9000, greater than about 9500, greater than about 10,000, greater than about 15,000, greater than about 20,000, greater than about 25,000, greater than about 50,000, greater than about 100,000, greater than about 150,000, greater than about 200,000 or greater than about 250,000 micrograms of a sequestration agent is added per 100 $LD_{50}$ Units of a *botulinum* neurotoxin. More preferably, between about 500 to 1000, about 500 to 1500, about 500 to 2000, about 500 to 2500, about 500 to 3000, about 500 to 3500, about 500 to 4000, about 500 to 4500, about 500 to 5000, about 500 to 10,000, about 500 to 20,000, about 1000 to 1500, about 1000 to 2000, about 1000 to 2500, about 1000 to 3000, about 1000 to 3500, about 1000 to 4000, about 1000 to 4500, about 1000 to 5000, about 1000 to 5500, about 1000 to 6000, about 1000 to 6500, about 1000 to 7000, about 1000 to 7500, about 1000 to 8000, about 1000 to 8500, about 1000 to 9000, about 1000 to 9500, about 1000 to 10,000, about 1000 to 15,000, about 1000 to 20,000, about 1000 to 25,000, or about 1000 to 50,000 micrograms of a sequestration agent is added to 100 $LD_{50}$ Units o a *botulinum* neurotoxin, and wherein the resultant formulation has an increased clinical potency.

The present invention also provides methods of treating cervical dystonia comprising the step of administering between about 15 to 150 Units per treatment of a pharmaceutical formulation comprising a *botulinum* toxin to a subject in need thereof, wherein administration of said formulation produces muscle weakness. In a preferred embodiment, the pharmaceutical formulation is administered to one or more of the muscles selected from the group consisting of: sternomastoid, levator scapulae, splenius cervis, capitus, scalene, and trapezium. Preferably, between about 15 to 30 Units, 15 to 50 Units, 15 to 75 Units, 15 to 100 Units, 15 to 125 Units, 15 to 150 Units, 20 to 100 Units, 20 to 150 Units, or 100 to 150 Units per treatment are administered to a patient with cervical dystonia. Most preferably, about 15, about 20, about 25, about 30, about 35, about 40, about 45 about 50, about 55, about 60, about 65, about 70, about 75, about 80, about 85, about 90, about 95, about 100, about 105, about 110, about 115, about 120, about 125, about 130, about 135, about 140, about 145, or about 150 Units per treatment are administered to a patient with cervical dystonia. Dosages greater than 150 Units per treatment may also be administered to patients with cervical dystonia to achieve a therapeutic response.

In another embodiment, the present invention provides methods of treating blepharospasm comprising the step of administering between about 1.5 to 20 Units per treatment of a pharmaceutical formulation comprising a *botulinum* toxin to a subject in need thereof, wherein administration of said formulation produces muscle weakness. Preferably, the pharmaceutical formulation is administered to an orbicular muscle of said subject. In another embodiment, between about 1.5 to 5 Units, 1.5 to 7 Units, 1.5 to 10 Units, 1.5 to 12 Units, 1.5 to 15 Units, 1.5 to 17 Units, 2.0 to 5 Units, 2 to 10 Units, 2 to 15, 2 to 20, 5 to 10, 5 to 15, or 5 to 20 Units per treatment are administered to a patient with blepharospasm. Most preferably, about 1.5, about 2.0, about 2.5, about 3.0, about 3.5, about 4.0, about 4.5 about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, or about 20.0 Units per treatment are administered to a patient with blepharospasm. Dosages greater than 20 Units per treatment may also be administered to patients with blepharospasm to achieve a therapeutic response.

In yet another embodiment, the present invention provides methods of treating hyperhydrosis comprising the step of administering between about 0.5 to 50 Units per treatment of a pharmaceutical formulation comprising a *botulinum* toxin to a subject in need thereof, wherein administration of said formulation reduces sweating. Preferably, the pharmaceutical formulation is administered to an axillae. In another embodiment, between about 0.5 to 5 Units, 0.5 to 10 Units, 0.5 to 15 Units, 0.5 to 20 Units, 0.5 to 25 Units, 0.5 to 30 Units, 0.5 to 35 Units, 0.5 to 40 Units, 0.5 to 45, 0.5 to 50, 2 to 10, 2 to 20, 2 to 30, 2 to 40, or 2 to 50 Units per treatment are preferably administered to a patient suffering from hyperhydrosis. Most preferably, about 0.5, about 1.0, about 1.5, about 2.0, about 2.5, about 3.0, about 3.5 about 4.0, about 4.5, about 5.0, about 5.5, about 6.0, about 6.5, about 7.0, about 7.5, about 8.0, about 8.5, about 9.0, about 9.5, about 10.0, about 12, about 15, about 17, about 20, about 22, about 25, about 27, about 30, about 32, about 35, about 37, about 40, about 42, about 45, about 47, or about 50 Units per treatment are administered to a patient with hyperhydrosis. Dosages greater than 50 Units per treatment may also be administered to patients with hyperhydrosis to achieve a therapeutic response.

The present invention also provides methods of treating migraine headache pain comprising the step of administering between about 0.5 to 50 Units per treatment of a pharmaceutical formulation comprising a *botulinum* toxin to a subject in need thereof, wherein administration of said formulation reduces migraine headache pain. In another embodiment, between about 0.5 to 5 Units, 0.5 to 10 Units, 0.5 to 15 Units, 0.5 to 20 Units, 0.5 to 25 Units, 0.5 to 30 Units, 0.5 to 35 Units, 0.5 to 40 Units, 0.5 to 45, 0.5 to 50, 2 to 10, 2 to 20, 2 to 30, 2 to 40, or 2 to 50 Units per treatment are preferably administered to a patient suffering from migraine headache pain. Most preferably, about 0.5, about 1.0, about 1.5, about 2.0, about 2.5, about 3.0, about 3.5 about 4.0, about 4.5, about 5.0, about 5.5, about 6.0, about 6.5, about 7.0, about 7.5, about 8.0, about 8.5,. about 9.0, about 9.5, about 10.0, about 12, about 15, about 17, about 20, about 22, about 25, about 27, about 30, about 32, about 35, about 37, about 40, about 42, about 45, about 47, or about 50 Units per treatment are administered to a patient with migraine headache pain. Dosages greater than 50 Units per treatment may also be administered to patients with migraine headache pain to achieve a therapeutic response.

The present invention also provides methods of treating facial pain comprising the step of administering between about 4 to 40 Units per treatment of a pharmaceutical formulation comprising a *botulinum* toxin to a subject in need thereof, wherein administration of said formulation reduces facial pain. In one embodiment, the facial pain is associated with sinusitis. In another embodiment, the facial pain is associated with trigeminal neuralgia. In yet another embodiment, the facial pain is post-surgical wound pain. In another embodiment, between about 4 to 7 Units, about 4 to 10 Units, about 4 to 15 Units, about 4 to 20 Units, about 4 to 25 Units, about 4 to 30 Units, about 4 to 35 Units, or about 4 to 40 Units per treatment are preferably administered to a patient suffering from facial pain. Most preferably, about 4.0, about 4.5, about 5.0, about 5.5, about 6.0, about 6.5, about 7.0, about 7.5, about 8.0, about 8.5, about 9.0, about 9.5, about 10.0, about 12, about 15, about 17, about 20, about 22, about 25, about 27, about 30, about 32, about 35, about 37, about 40, about 42, about 45, about 47, or about 50 Units per treatment are administered to a patient with facial pain. Dosages greater than 40 Units per treatment may also be administered to patients with facial pain to achieve a therapeutic response.

The present invention also provides methods of treating strabismus comprising the step of administering between about 4 to 40 Units per treatment of a pharmaceutical formulation comprising a *botulinum* toxin to a subject in need thereof, wherein administration of said formulation reduces symptoms of strabismus. Preferably, between about 4 to 7 Units, about 4 to 10 Units, about 4 to 15 Units, about 4 to 20 Units, about 4 to 25 Units, about 4 to 30 Units, about 4 to 35 Units, or about 4 to 40 Units per treatment are preferably administered to a patient suffering from strabismus. Most preferably, about 4.0, about 4.5, about 5.0, about 5.5, about 6.0, about 6.5, about 7.0, about 7.5, about 8.0, about 8.5, about 9.0, about 9.5, about 10.0, about 12, about 15, about 17, about 20, about 22, about 25, about 27, about 30, about 32, about 35, about 37, about 40, about 42, about 45, about 47, or about 50 Units per treatment are administered to a patient with strabismus. Dosages greater than 40 Units per treatment may also be administered to patients with strabismus to achieve a therapeutic response.

The present invention also provides methods of treating hyperactive bladder comprising the step of administering between about 4 to 40 Units per treatment of a pharmaceutical formulation comprising a *botulinum* toxin to a subject in need thereof, wherein administration of said formulation reduces urination frequency. Preferably, between about 4 to 7 Units, about 4 to 10 Units, about 4 to 15 Units, about 4 to 20 Units, about 4 to 25 Units, about 4 to 30 Units, about 4 to 35 Units, or about 4 to 40 Units per treatment are preferably administered to a patient suffering from hyperactive bladder. Most preferably, about 4.0, about 4.5, about 5.0, about 5.5, about 6.0, about 6.5, about 7.0, about 7.5, about 8.0, about 8.5, about 9.0, about 9.5, about 10.0, about 12, about 15, about 17, about 20, about 22, about 25, about 27, about 30, about 32, about 35, about 37, about 40, about 42, about 45, about 47, or about 50 Units per treatment are administered to a patient with hyperactive bladder. Dosages greater than 40 Units per treatment may also be administered to patients with facial pain to achieve a therapeutic response.

The present invention also provides methods of treating muscle spasticity comprising the step of administering between about 20 to 200 Units per treatment of a pharmaceutical formulation comprising a *botulinum* toxin to a subject in need thereof, wherein administration of said formulation produces muscle weakness. Preferably, between about 20 to 30 Units, 20 to 40 Units, 20 to 60 Units, 20 to 80 Units, 20 to 100 Units, 20 to 125 Units, 20 to 150 Units, or 20 to 175 Units per treatment a administered to a patient with muscle spasticity. Most preferably, about 20, about 25, about 30, about 35, about 40, about 45 about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 Units per treatment are administered to a patient with muscle spasticity. Dosages greater than 200 Units per treatment may also be administered to patients with muscle spasticity to achieve a therapeutic response.

The present invention also provides methods of treating hemifacial spasm comprising the step of administering between about 1.5 to 15 Units per treatment of a pharmaceutical formulation comprising a *botulinum* toxin to a subject in need thereof, wherein administration of said formulation produces muscle weakness. Preferably, between about 1.5 to 5 Units, about 1.5 to 7 Units, about 1.5 to 10 Units, about 1.5 to 12 Units, about 1.5 to 15 Units, about 2.0 to 5 Units, about 2 to 10 Units, about 2 to 15, about 5 to 10, about 5 to 15, or about 5 to 20 Units per treatment are administered to a patient with hemifacial spasm. Most preferably, about 1.5, about 2.0, about 2.5, about 3.0, about 3.5, about 4.0, about 4.5 about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, about 14.0, about 14.5, or about 15.0 Units per treatment are administered to a patient with hemifacial spasm. Dosages greater than 15 Units per treatment may also be administered to patients with hemifacial spasm to achieve a therapeutic response.

The present invention also provides methods of myofascial pain comprising the step of administering between about 5 to 100 Units per treatment of a pharmaceutical formulation comprising a *botulinum* toxin to a subject in need thereof, wherein administration of said formulation reduces myofascial pain. In a preferred embodiment, the myofascial pain is pain associated with cervical dystonia or temporal mandibular joint syndrome. More preferably, the myofascial pain is pain associated with cervical dystonia. In another embodiment, between about 5 to 10 Units, 5 to 20 Units, 5 to 30 Units, 5 to 40 Units, 5 to 50 Units, 5 to 60 Units, 5 to 70 Units, 5 to 80 Units, 5 to 90, 10 to 20, 10 to 30, 10 to 50 or 10 to 60, or 10 to 70, or 10 to 80, 10 to 90 or 10 to 100 Units per treatment are administered to a patient suffering from myofascial pain. Most preferably, about 5, about 10, about 15, about 20, about 25, about 30, about 35 about 40, about 45, about 50, about 55, about 60, about 65, about 70, about 75, about 80, about 85, about 90, about 95 or about 100 Units per treatment are administered to a patient with myofascial pain. Dosages greater than 100 Units per treatment may also be administered to patients with myofascial pain to achieve a therapeutic response.

The present invention also provides methods of treating facial pain comprising the step of administering between about 4 to 40 Units per treatment of a pharmaceutical formulation comprising a *botulinum* toxin to a subject in need thereof, wherein administration of said formulation reduces facial pain. Preferably, between about 4 to 10 Units, 4 to 15 Units, 4 to 20 Units, 4 to 25 Units, 4 to 30 Units, 4 to 35 Units, 7 to 15 Units, 7 to 20 Units, 7 to 25, 7 to 30, 7 to 35, or 7 to 40 Units per treatment are administered to a patient suffering from facial pain. Most preferably, about 4, about 5, about 7.5, about 10, about 12.5, about 15, about 17.5 about 20.0, about 22.5, about 25.0, about 27.5, about 30.0, about 32.5, about 35, about 37.5, or about 40 Units per treatment are administered to a patient with facial pain. Dosages greater than 40 Units per treatment may also be administered to patients with facial pain to achieve a therapeutic response.

The present invention also provides methods of treating inflammation comprising the step of administering between about 5 to 100 Units per treatment of a pharmaceutical formulation comprising a *botulinum* toxin to a subject in need thereof, wherein administration of said formulation reduces inflammation. In a preferred embodiment, the inflammation is associated with arthritis or the inflammation is intestinal. In another embodiment, between about 1 to 10 Units, 1 to 20 Units, 1 to 30 Units, 1 to 40 Units, 1 to 50 Units, 1 to 60 Units, 1 to 70 Units, 1 to 80 Units, 1 to 90, 5 to 20, 5 to 30, 5 to 40, 5 to 50, 5 to 60, 5 to 70, 5 to 80, 5 to 90, or 5 to 100 Units per treatment are administered to a patient with an inflammatory disorder. Most preferably, about 1, about 10, about 20, about 30, about 40, about 50, about 60, about 70, about 80, about 90, or about 100 Units per treatment are administered to a patient with tension-headache pain. Dosages greater than 100 Units per treatment may also be administered to patients suffering from inflammation or an inflammatory disorder to achieve a therapeutic response.

The present invention also provides methods of method of treating blepharitis comprising the step of administering between about 1 to 10 Units per treatment of a pharmaceutical formulation comprising a *botulinum* toxin to a subject in need thereof, wherein administration of said formulation reduces inflammation. In a preferred embodiment, between about 1 to 3 Units, about 1 to 5 Units, about 1 to 7 Units, or 1 to 10 Units per treatment are administered to a patient with an inflammatory disorder. Most preferably, about 1, about 2, about 3, about 4, about 5, about 6, about 7, about 8, about 9, or about 10 Units per treatment are administered to a patient with tension-headache pain. Dosages greater than 10 Units per treatment may also be administered to patients suffering from inflammation or an inflammatory disorder to achieve a therapeutic response.

The present invention also provides methods of treating scoliosis comprising the step of administering between about 30 to 300 Units per treatment of a pharmaceutical formulation comprising a *botulinum* toxin to a subject in need thereof, wherein administration of said formulation improves posture. In a preferred embodiment, between about 30 to 50 Units, about 30 to 75 units, about 30 to 100 Units, about 30 to 125 Units, about 30 to 150 Units, about 30 to 175 Units, about 30 to 200 Units, about 30 to 225 Units, about 30 to 250 Units, about 30 to 275 Units, or about 30 to 300 Units per treatment are administered to a patient with scoliosis. More preferably, about 30, about 35, about 40, about 45, about 50, about 55, about 60, about 65, about 70, about 75, about 80, about 85, about 90, about 100, about 110, about 120, about 130, about 140, about 145, about 150, about 155, about 160, about 165, about 170, about 175, about 180, about 185, about 190, about 200, about 210, about 220, about 230, about 240, about 245, about 250, about 255, about 260, about 265, about 270, about 275, about 280, about 285, about 290, or about 300 Units per treatment are administered to a patient with scoliosis. Dosages greater than 300 Units per treatment may also be administered to patients suffering from scoliosis to achieve a therapeutic response.

The present invention also provides methods of treating tension headache comprising the step of administering between about 5 to 50 Units per treatment of a pharmaceutical formulation comprising a *botulinum* toxin to a subject in need thereof, wherein administration of said formulation reduces pain. Preferably, between about 5 to 10 Units, 5 to 15 Units, 5 to 20 Units, 5 to 25 Units, 5 to 30 Units, 5 to 35 Units, 5, to 40 Units, 5 to 45 Units, 10 to 20, 10 to 25, 10 to 30, 10 to 35, 10 to 40, 10 to 45, or 10 to 45 Units per treatment are administered to a patient with tension-headache pain. Most preferably, about 5, about 10, about 20, about 25, about 30, about 35, about 40, about 45, or about 50 Unit per treatment are administered to a patient with tension-headache pain. Dosages greater than 50 Units per treatment may also be administered to patients with tension-headache pain to achieve a therapeutic response.

The present invention also provides methods of treating lower back pain comprising the step of administering between about 15 to 150 Units per treatment of a pharmaceutical formulation comprising a *botulinum* toxin to a subject in need thereof, wherein administration of said formulation reduces pain. Preferably, between about 15 to 30 Units, 15 to 50 Units, 15 to 75 Units, 15 to 100 Units, 15 to 125 Units, 15 to 150 Units, 20 to 100 Units, 20 to 150 Units, or 100 to 150 Units per treatment are administered to a patient with lower-back pain. Most preferably, about 15, about 20, about 25, about 30, about 35, about 40, about 45 about 50, about 55, about 60, about 65, about 70, about 75, about 80, about 85, about 90, about 95, about 100, about 105, about 110, about 115, about 120, about 125, about 130, about 135, about 140, about 145, or about 150 Units per treatment are administered to a patient with lower-back pain. Dosages greater than 150 Units per treatment may also be administered to patients with lower-back pain to achieve a therapeutic response.

The present invention also provides methods of treating scleroderma comprising the step of administering between about 30 to 300 Units per treatment of a pharmaceutical formulation comprising a *botulinum* toxin to a subject in need thereof, wherein administration of said formulation reduces a symptom of scleroderma. In a preferred embodiment, between about 30 to 50 Units, about 30 to 75 units, about 30 to 100 Units, about 30 to 125 Units, about 30 to 150 Units, about 30 to 175 Units, about 30 to 200 Units, about 30 to 225 Units, about 30 to 250 Units, about 30 to 275 Units, or about 30 to 300 Units per treatment are administered to a patient with scleroderma. More preferably, about 30, about 35, about 40, about 45, about 50, about 55, about 60, about 65, about 70, about 75, about 80, about 85, about 90, about 100, about 110, about 120, about 130, about 140, about 145, about 150, about 155, about 160, about 165, about 170, about 175, about 180, about 185, about 190, about 200, about 210, about 220, about 230, about 240, about 245, about 250, about 255, about 260, about 265, about 270, about 275, about 280, about 285, about 290, or about 300 Units per treatment are administered to a patient with scleroderma. Dosages greater than 300 Units per treatment may also be administered to patients suffering from scleroderma to achieve a therapeutic response.

The present invention also provides methods of treating asthma and/or hayfever comprising the step of administering between about 5 to 50 Units per treatment of a pharmaceutical formulation comprising a *botulinum* toxin to a subject in need thereof, wherein administration of said formulation reduces inflammation. Preferably, between about 5 to 10 Units, 5 to 15 Units, 5 to 20 Units, 5 to 25 Units, 5 to 30 Units, 5 to 35 Units, 5 to 40 Units, 5 to 45 Units, 10 to 20, 10 to 25, 10 to 30, 10 to 35, 10 to 40, 10 to 45, or 10 to 45 Units per treatment are administered to a patient with asthma and/or hayfever. Most preferably, about 5, about 10, about 20, about 25, about 30, about 35, about 40, about 45, or about 50 Units per treatment are administered to a patient with asthma and/or hayfever. Dosages greater than 50 Units per treatment may also be administered to patients with asthma and/or hayfever to achieve a therapeutic response.

The present invention also provides methods of treating prostatitis comprising the step of administering between about 10 to 100 Units per treatment of a pharmaceutical formulation comprising a *botulinum* toxin to a subject in need thereof, wherein administration of said formulation reduces inflammation. In a preferred embodiment, the administration of said formulation reduces prostate size. Preferably, between about 10 to 30 Units, about 10 to 50 Units, about 10 to 75 Units, about 10 to 100 Units, about 20 to 50 Units, about 20 to 75 Units, or about 20 to 100 Units per treatment are administered to a patient with prostatitis. Most preferably, about 10, about 15, about 20, about 25, about 30, about 35, about 40, about 45 about 50, about 55, about 60, about 65, about 70, about 75, about 80, about 85, about 90, about 95, or about 100 Units per treatment are administered to a patient with prostatitis. Dosages greater than 100 Units per treatment may also be administered to patients with prostatitis to achieve a therapeutic response.

The present invention also provides methods of treating facial rhytides comprising the step of administering between about 2 to 20 Units per treatment of a pharmaceutical formulation comprising a *botulinum* toxin a subject in need thereof, wherein administration of said formulation reduces facial lines. In a preferred embodiment, the pharmaceutical formulation is administered to reduce vertical lines between the eyebrows and/or on a bridge of a nose. In another embodiment, the pharmaceutical formulation is administered to reduce lines at corners of the eyes. In yet another embodiment, the pharmaceutical formulation is administered to reduce horizontal lines on said forehead. In a preferred embodiment, between about 2 to 5 Units, about 2 to 6 Units, about 2 to 7 Units, about 2 to 8 Units, about 2 to 9 Units, about 2 to 10 Units, about 2 to 11 Units, about 2 to 12 Units, about 2 to 13 Units, about 2 to 14 Units, about 2 to 15 Units, about 2 to 16 Units, about 2 to 17 Units, about 1 to 18 Units, 1 to 19 Units, or about 2 to 20 Units per treatment are administered to a patient with facial rhytides. Most preferably, about 2, about 3, about 4, about 5, about 6, about 7, about 8, about 9, about 10, about 11, about 12, about 13, about 14, about 15, about 16, about 17, about 18, about 19, or about 20 Units per treatment are administered to a patient with facial rhytides. Dosages greater than 20 Units per treatment may also be administered to a patient with facial rhytides to achieve a therapeutic response.

The present invention also provides methods for reducing scarring and/or cosmetic deformity associated with burns or skin disorders such as blistering dermatosis comprising the step of administering a pharmaceutical formulation comprising a *botulinum* toxin to a subject in need thereof, wherein administration of said formulation reduces scarring and/or cosmetic deformity. In another embodiment, the pharmaceutical formulation comprises a *botulinum* toxin and a sequestration agent, as disclosed herein. In yet another embodiment, the pharmaceutical formulation comprises a *botulinum* toxin, a sequestration agent, as disclosed herein, and a stabilizing agent, such as trehalose. Further, the pharmaceutical formulation comprises an agent that promotes cutaneous absorption and penetration. In a preferred embodiment, the pharmaceutical formulation is administered to a body surface of said subject. In a preferred embodiment, the pharmaceutical formulation is administered as a liquid formulation. More preferably, the pharmaceutical formulation is applied as an aerosol. In another embodiment, between about 1 and 10, about 1 and 50, about 1 and 100, about 1 and 200, about 1 and 500, about 1 and 1000, about 1 and 1250, about 1 and 1500, about 1 and 2000, or about 1 and 2500 Units per treatment are administered to a subject suffering from a burn. As used herein, "burn" includes but is not limited to thermal, electrical, or chemical burns and also includes blistering caused by dermatitis and other blistering disorders. In an alternative embodiment, mechanical abrasion, chemical, thermal, laser-induced disruption of skin barriers, and the like, may be used to improve the delivery of topical administration of pharmaceutical formulations of *botulinum* toxin.

The present invention provides a composition comprising *botulinum* toxin and a sequestration agent for use in treating various neuromuscular diseases and localized denervation. In one embodiment, the sequestration agent is present in an amount between 550 and 550,000 µg sequestration agent per 100 $LD_{50}$ units *botulinum* toxin. In another embodiment, the sequestration agent is present in an amount between 550 and 5,500 µg sequestration agent per 100 $LD_{50}$ units *botulinum* toxin. In a further embodiment, the sequestration agent is present in an amount between 5,500 and 13,000 µg sequestration agent per 100 $LD_{50}$ units *botulinum* toxin. In a preferred embodiment, the sequestration agent is present in an amount between 13,000 and 50,500 µg sequestration agent per 100 $LD_{50}$ units *botulinum* toxin. In a more preferred embodiment, the sequestration agent is present in an amount between 50,500 and 505,000 µg sequestration agent per 100 $LD_{50}$ units *botulinum* toxin. In the most preferred embodiment, the sequestration agent is formulated as encapsulated microspheres in an amount between 50,500 and 90,500 µg sequestration agent per 100 $LD_{50}$ units *botulinum* toxin.

The *botulinum* toxin of the present compositions may be selected from a variety of strains of *Clostridium botulinum*. In a preferred embodiment, the compositions of the present invention comprises a *botulinum* toxin selected from the group consisting of *botulinum* toxin types A, B, C, D, E, F and G. In a preferred embodiment, the *botulinum* toxin is *botulinum* toxin type A. In a more preferred embodiment, the *botulinum* toxin is *botulinum* toxin type A from the Hall strain of *Clostridium botulinum*.

In another embodiment, the compositions of the present invention comprise a *botulinum* toxin that consists essentially of fractionated-light-chain *botulinum* toxin. In yet another embodiment, the *botulinum* toxin consists essentially of a mixture of hybrid and chain-translocated forms of *botulinum* toxin. In a further embodiment, the *botulinum* toxin consists essentially of chimeric forms of *botulinum* toxin. Although the present invention may utilize any *botulinum* toxin, *botulinum* toxin fragment that retains neurotoxic activity, *botulinum* toxin chimeras and hybrids, chemically-modified *botulinum* toxin, and specific activities well known to those of ordinary skill in the art, in one embodiment the *botulinum* toxin is purified to a specific activity greater than or equal to 20 $LD_{50}$ units per nanogram *botulinum* toxin.

The present invention provides compositions of *botulinum* toxin and a sequestration agent wherein the ratio of $LD_{50}$ units of *botulinum* toxin to µg sequestration agent is less than or equal to 0.2 for *botulinum* toxin type A and is less than or equal to 10 for *botulinum* toxin type B.

Each composition of the present invention, in addition to comprising a *botulinum* toxin and a sequestration agent, may further comprise a pharmaceutically acceptable carrier and/or zinc and/or a zinc salt. In one embodiment, the *botulinum* toxin is noncovalently bound to the sequestration agent. In another embodiment, the *botulinum* toxin is covalently bound to the sequestration agent.

The present invention provides compositions of a *botulinum* toxin and a sequestration agent, wherein the sequestration agent is selected from the group consisting of: proteins, lipids and carbohydrates. In a preferred embodiment, the sequestration agent is albumin, collagen, epinephrine or hyaluronate. In a more preferred embodiment, the sequestration agent is hyaluronate. In the most preferred embodiment, the sequestration agent is albumin.

The present invention further provides compositions comprising a *botulinum* toxin and a sequestration agent, wherein the sequestration agent is an albumin, preferably human serum albumin. Furthermore, in one embodiment, the albumin of the present compositions is recombinantly produced. In one embodiment, albumin is present in an amount between 550 and 5,500 µg albumin per 100 $LD_{50}$ units *botulinum* toxin. In a further embodiment, albumin is present in an amount between 5,500 and 13,000 µg albumin per 100 $LD_{50}$ units *botulinum* toxin. In a preferred embodiment, albumin is present in an amount between 13,000 and 50,500 µg albumin per 100 $LD_{50}$ units *botulinum* toxin. In a more preferred embodiment, albumin is present in an amount between 50,500 and 505,000 µg albumin per 100 $LD_{50}$ units *botulinum* toxin. In a most preferred embodiment, albumin is formulated as encapsulated microspheres in an amount between 50,500 and 90,500 µg albumin per 100 $LD_{50}$ units *botulinum* toxin.

In another embodiment, the present invention provides a composition comprising *botulinum* toxin and a sequestration agent, wherein the sequestration agent is present in an amount between 550 and 900,500 µg sequestration agent per 100 $LD_{50}$ units *botulinum* toxin, wherein the albumin may be formulated as a solid albumin particle.

In one embodiment of the present invention, the compositions comprise a *botulinum* toxin and at least one sequestration agent. In a preferred embodiment, the compositions of the present invention comprising a *botulinum* toxin and albumin and further comprising one or more additional sequestration agents.

The present invention also provides methods of producing localized denervation in a subject in need thereof, comprising administering an effective amount of any of the compositions of the present invention that are described herein. In one embodiment, the methods of the present invention are used to produce denervation in a subject that suffers from a neuromuscular disease associated with increased muscle tone with involuntary movement. In another embodiment, the methods of the present invention are used to produce denervation in a subject that suffers from a neuromuscular disease. Preferably, the neuromuscular disease is characterized by increased muscle tone and/or involuntary movement, including but not limited to dystonias, spinal cord injury or disease, multiple sclerosis, spasticity, cerebral palsy, stroke, and the like. Preferably, the neuromuscular disease associated with increased muscle tone and/or involuntary movement is blepharospasm or torticollis. More preferably, the neuromuscular disease associated with increased muscle tone with involuntary movement is blepharospasm.

In one embodiment, the present invention provides methods for producing denervation in a subject suffering from blepharospasm comprising administering between 10-200 $LD_{50}$ units of a composition of the present invention, as described herein. In another embodiment, the present invention provides methods for producing denervation in a subject suffering from torticollis. Preferably, the effective amount of a composition of the present invention is between 10 and 3000 $LD_{50}$ units.

In another embodiment, the present invention provides a method of treating a condition selected from the group consisting of facial wrinkles, rhytides and cosmetic alteration of lip and brow, in a subject in need thereof, comprising administering an effective amount of a composition of the present invention, as disclosed herein. Preferably, the effective amount is between 2.5 and 400 $LD_{50}$ units.

In yet another embodiment, the present invention provides a method of treating human headache disorders in a subject in need thereof, comprising administering an effective amount of a composition of the present invention, as disclosed herein. Preferably, the effective amount is between 5 and 1000 $LD_{50}$ units.

In a further embodiment, the present invention provides a method of treating human migraine headache disorders in a subject in need thereof, comprising administering an effective amount of a composition of the present invention, as disclosed herein. Preferably, the effective amount is between 5 and 1,000 $LD_{50}$ units.

The present invention also provides a method of treating human inflammatory conditions in a subject in need thereof, comprising administering an effective amount of a composition of the present invention, as disclosed herein. Preferably, the effective amount is between 5 and 4,000 $LD_{50}$ units.

The present invention also provides a method of treating myopathic or neuropathic pain in a subject in need thereof, comprising administering an effective amount of a composition of the present invention, as disclosed herein. Preferably, the effective amount is between 5 and 4,000 $LD_{50}$ units.

The present invention also provides a method of treating back pain or arthritic pain in a subject in need thereof, comprising administering an effective amount of a composition of the present invention, as disclosed herein. Preferably, the effective amount is between 5 and 4,000 $LD_{50}$ units.

In yet another embodiment, the present invention provides a method of treating gastrointestinal spasm and strictures in a subject in need thereof, comprising administering an effective amount of a composition of the present invention, as disclosed herein. Preferably, the effective amount is between 5 and 4,000 $LD_{50}$ units.

The present invention provides a method of treating a hyperhyrosis syndrome in a subject in need thereof, comprising administering an effective amount of a composition of the present invention, as disclosed herein. Preferably, the effective amount is between 5 and 4,000 $LD_{50}$ units.

The present invention also provides a method of producing the compositions described herein. In one embodiment, the method comprises mixing a sequestration agent with botulinum toxin. In another embodiment, the method comprises freeze drying or flash drying a sequestration agent with botulinum toxin. Preferably, the botulinum toxin and the sequestration agent are in a weight to weight ratio which exceeds 100 µg sequestration agent to 1 ng of botulinum toxin.

DETAILED DESCRIPTION OF THE INVENTION

Figure 1:
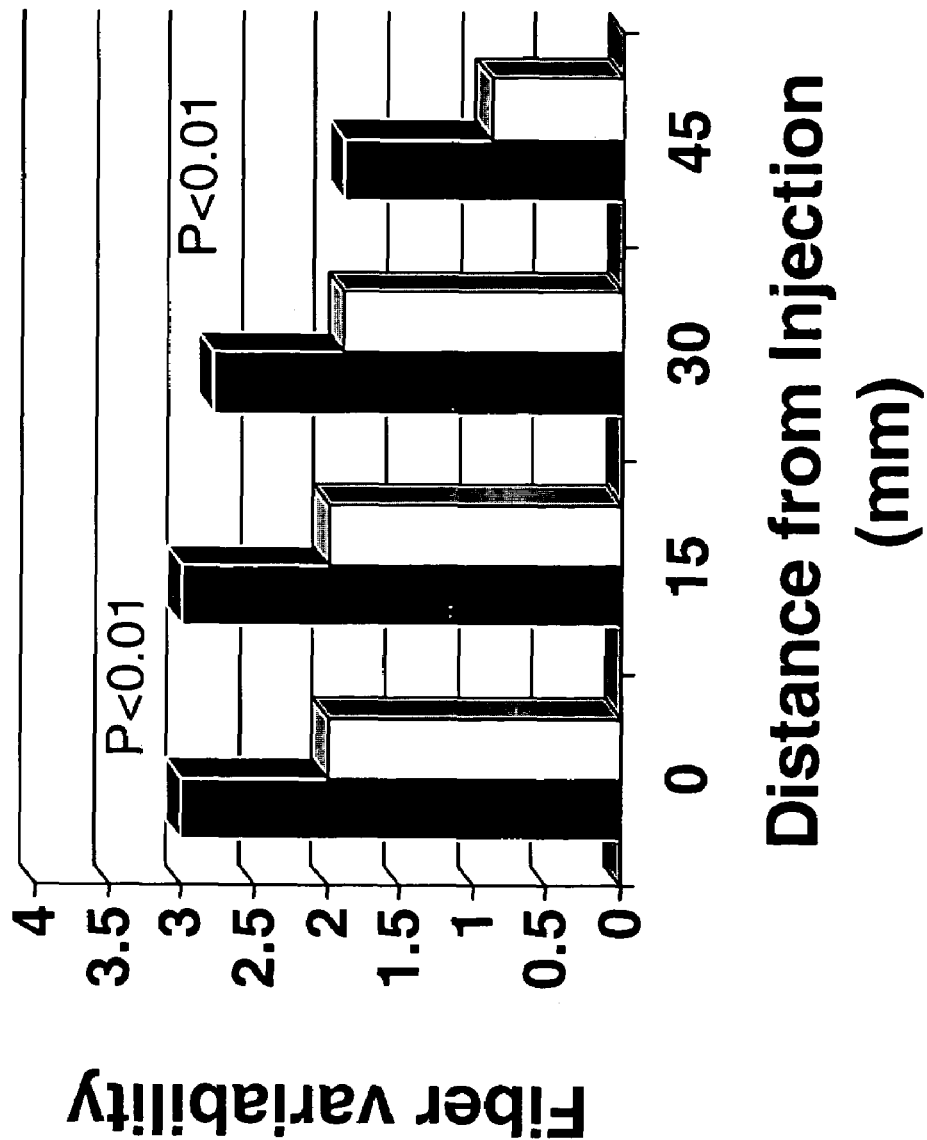
FIG. 1 depicts the denervation potency of two botulinum toxin preparations as determined by muscle fiber variability.

The present invention describes a method and composition to enhance the clinical effectiveness of botulinum-toxin preparation for clinical use by means of increasing sequestration of botulinum neurotoxin molecules in the region targeted for therapy through the use of a sequestration agent or "molecular anchor". Enhanced sequestration using higher concentration of macromolecules such as proteins (e.g., albumin, collagen and the like), and/or lipids and/or polysaccharides (e.g., hyaluronate, and the like) can be useful to provide a molecular anchor to neurotoxin molecules preventing diffusion away from the injection point, causing maximal saturation of botulinum neurotoxin receptors, thereby achieving greater efficacy with the amount of neurotoxin used to achieve desired clinical effects. The sequestration agent enhances containment of regional denervation, and enhances clinical outcomes. The increased sequestration allows for better delivery to nerve ending, with enhanced uptake and augmentation of denervative and other biologic effects. The invention requires a sequestration agent added to a formulation of neurotoxin which binds to the neurotoxin, prevents dissemination of the neurotoxin and demonstrates improvement in clinical response in patients who were previously treated without the carrier molecule at preferred concentrations. The sequestration agent may be an existing excipient at significantly higher concentrations than previously used (such as human serum albumin), or a material that has not been previously used to stabilize botulinum toxin ( such as sodium hyaluronate). The sequestration agent must bind to the botulinum toxin molecule and prevents its diffusion so that the neurotoxin may react with the nerve-terminal ending or any neural structure so that effectiveness of the therapy is improved.

A. Definitions.

As used herein, "Botulinum toxin" means a protein toxin isolated from strains of Clostridium botulinum, including mixtures of its protein complexes, toxoid and/or other clostridial proteins. "Botulinum toxin" includes all of the various immunotypes such as A, B, $C_1$, $C_2$, $C_3$, D, E, F and G.

As used herein, "an effective amount" is an amount sufficient to produce a therapeutic response. An effective amount may be determined with dose escalation studies in open-labeled clinical trials or bin studies with blinded trials.

As used herein, "increased clinical potency" means that fewer $LD_{50}$ Units of a pharmaceutical formulation comprising a botulinum toxin and a sequestration agent (as described herein) are necessary for "an effective amount" of a botulinum toxin for the treatment of glabellar lines than a botulinum toxin preparation without an added sequestration agent.

As used herein "neuromuscular diseases" refer to any disease adversely affecting both nervous elements (brain, spinal cord, peripheral nerve) or muscle (striated or smooth muscle), including but not limited to involuntary movement disorders, dystonias, spinal cord injury or disease, multiple sclerosis, and spasticity from cerebral palsy, stroke, or other cause.

As used herein, the term "pharmaceutically acceptable carrier" means a chemical composition, compound, or solvent with which an active ingredient may be combined and which, following the combination, can be used to administer the active ingredient to a subject. As used herein, "pharmaceutically acceptable carrier" includes, but is not limited to, one or more of the following: excipients; surface active agents; dispersing agents; inert diluents; granulating and disintegrating agents; binding agents; lubricating agents; preservatives;

physiologically degradable compositions such as gelatin; aqueous vehicles and solvents; oily vehicles and solvents; suspending agents; dispersing or wetting agents; emulsifying agents, demulcents; buffers; salts; thickening agents; fillers; antioxidants; stabilizing agents; and pharmaceutically acceptable polymeric or hydrophobic materials and other ingredients known in the art and described, for example in Genaro, ed., 1985, Remington's Pharmaceutical Sciences, Mack Publishing Co., Easton, Pa., which is incorporated herein by reference.

As used herein, "sequestration agent" means an agent that enhances localization and/or retention of the *botulinum* toxin to the site of administration.

B. *Botulinum* Toxin.

*Botulinum* toxin type A is the most lethal natural biological agent known to man. Seven immunologically distinct *botulinum* neurotoxin serotypes have been characterized—A, B, $C_1$, D, E, F and G. Each *botulinum* toxin serotype is distinguished by neutralization with type-specific antibodies. The different serotypes of *botulinum* toxin vary in the animal species that they affect and in the severity and duration of the paralysis they evoke.

Since its introduction as a therapeutic agent, the pharmaceutical measurement of the denervating or biologic activity of *botulinum* toxin has been the $LD_{50}$ Unit ($LD_{50}$ Unit and Unit are used interchangeably herein) determined by using 18-22 gram Swiss-Webster mice, quantitated statistically by injecting cohorts of mice at different dilutions from the purified *botulinum* neurotoxin protein and its protein complexes. This measurement has the advantage of a clear endpoint (living or dead mouse), however the $LD_{50}$ unit does not predict clinical behavior of various *botulinum* toxin formulations when compared in clinical studies. For instance, one preparation of type B *botulinum* toxin (MYOBLOC®) requires 5,000-15,000 $LD_{50}$ units to treat torticollis whereas another preparation of *botulinum* toxin Type A (BOTOX®) requires only 100-300 $LD_{50}$ units. Similarly, the $LD_{50}$ unit has failed to distinguish differences in therapeutic behavior of different sources of the same *botulinum* toxin immunotype. For instance, approximately 50-300 units of BOTOX® is required to treat blepharospasm and cervical dystonia compared to 200-1200 units of DYSPORT®, another preparation of *botulinum* type A toxin. Table 1 illustrates the varying doses for different diseases.

TABLE 1

Dosing comparisons between various pharmaceutical formulations of botulinum toxin.

| Formulation | Essential Blepharospasm | Torticollis |
| --- | --- | --- |
| BOTOX ® | 50 U[1] | 200 U |
| DYSPORT ® | 200 U | 600-1,200 U |
| MYOBLOC ® | 3,000-5,000 U | 10,000-15,000 U |

[1]Units (U) are $LD_{50}$ units determined using 20-30 g Swiss-Webster mice, as described herein.

Toxins of the different *C. botulinum* serotypes are produced in culture as aggregates of neurotoxin and other non-toxic proteins non-covalently associated into a polypeptide complex. (Schantz (1964) Purification and characterization of *C. botulinum* toxins, In *Botulism. Proceedings of a symposium*. K. Lewis and K. Cassel, Jr. (eds.), U.S. Department of Health, Education, and Welfare, Public Health Service, Cincinnati, pp. 91-104; Sugii et al. (1975) *Infect. Immun.* 12: 1262-1270; Kozaki et al., (1974) *Jpn. J. Med. Sci. Biol.* 28: 70-72; Miyazaki et al. (1977) *Infect. Immun.* 17: 395-401; Kitamura et al. (1969) *J. Bacteriol.* 98: 1173-1178; Ohishi et al. (1974) *Appl. Environ. Microbiol.* 28: 923-928; Yang et al. (1975) *Appl. Microbiol.* 29: 598-603). Toxin complexes are described as M for medium, L for large and LL for very large. These toxin complexes vary in size from about 900 kD for type A LL toxin complex to about 300 kD for the type B M complex and type E complex, to 235 kD for type F M complex. The Hall strain of type A *Clostridium botulinum* is preferably used for the production of type A neurotoxin. (Goodnough et al. (1992) *Appl. Environ. Microbiol.* 58(10): 3426-3428); Goodnough and Johnson (1994) *ACS Symposium Series No.* 567, J. Cleland and R. Linger (eds); Tse et al. (1982) *Eur. J. Biochem.* 122: 493-500). *Botulinum* neurotoxin may be prepared by culturing *Clostridium botulinum*, harvesting, solubilizing and purifying using standardized methods that ensure quality and sterility. (Schantz and Johnson (1992) *Microbiol. Rev.* 56: 80-99; (Goodnough et al. (1992) *Appl. Environ. Microbiol.* 58(10): 3426-3428); Goodnough and Johnson (1994) *ACS Symposium Series No.* 567, J. Cleland and R. Langer (eds); Tse et al. (1982) *Eur. J. Biochem.* 122: 493-500). incorporated herein by reference in its entirety).

C. Albumin.

Endogenous human serum albumin binds native circulating molecules, such as free fatty acids, bilrubin, hormones and zinc. Additionally, circulating human albumin can bind with many pharmaceutical agents which can influence potency, complication rate, clearance, and other pharmacodynamic properties of these agents. Examples include salicylates, sulfisoxazoles, warfarin, phenylbutazone, digitoxin, phenytoin, oxacillin, benyzlpenicillin, lasix, indomethacin, diazepam, and quinidine among others. Peptides and proteins also are known to bind human serum albumin. Peptide hormones such as gastrin, corticotropin, melatonin are also known to bind human serum albumin.

Several binding sites have been identified and binding has been thought to be non-covalent. Additionally, albumin can non-covalently bind cations that serve as cofactors for enzymatic reactivity of portions of the *botulinum* toxin polypeptide complex. Specifically, zinc is a cofactor for the endopeptidase activity of the *botulinum* toxin light chain which enters the target cells after heavy chain binding to the cell surface protein receptors. Higher quantities of zinc bound to albumin enhance endopeptidase activity. Zinc binding to albumin is dose dependent. Saturation of zinc binding on albumin enhances the denervating effect of *botulinum* toxin.

Albumin, because of larger atomic mass and other protein properties, is physiologically cleared from the injection area by lymph vessel absorption, not blood vessel absorption), a process which is much slower than removal of smaller molecular species. The relevance of albumin to *botulinum* toxin pharmaceuticals depends on its role in maintaining biologic activity by promoting nerve and other receptor contact and preventing wash out from free neurotoxin release at injection points. DYSPORT®, with its lower albumin concentration, offers less sequestration for the neurotoxin complex, and subsequently, after injected, diffusion away from the targeted anatomic area results. The clinical effect is a greater regional diffusion and chemodenervation over greater area, which results in increased complications (ptosis, Dyspahgia see Table 2). In order to compensate for this behavior, clinicians have given four to five time as much neurotoxin to achieve the same degree of biologic activity as formulations such as BOTOX® have higher albumin concentrations. With less potent immunotypes such as *botulinum* toxin type B (MYOBLOC®), larger dose are needed to achieve the same regional bioeffect, thereby further increasing diffusion and complication rates (see Table 2). The lower potency observed for immunotypes are thought to be related to poor receptor binding or binding to alternative less efficient receptor sites. Administration of more *botulinum* toxin (higher protein load), in addition to increased diffusion, also results in higher immunity rates after repeated injections. (Borodic et al. (1996) *Botulinum* Toxin, Immunology and Problems with Available Materials. *Neurology* 46: 26-29).

MYOBLOC® is formulated at an acidic pH<6.0 which provides for increased stability and stability of the liquid formulation at room temperature. Unfortunately, the acidic pH has an adverse side effect on the structure and probably tissue carrying properties of the human serum albumin in this formulation. The isomerization, tertiary structure and physical properties of albumin can vary considerably at various pH. (see Peters (1996) All about Albumin. Academic Press, New York; incorporated herein by reference in its entirety). Alterations in physical properties (via changes in binding of *botulinum* toxin and the dynamics of *botulinum* toxin molecular release in tissues) may contribute to differences in dose requirements comparing BOTOX® and MYOBLOC® in clinical practice.

Although other proteins (e.g. gelatin, lactalbumin, lysozyme), lipids and carbohydrates may serve as effective sequestration agents, albumin, including encapsulated albumin and solid microspheres is the preferred protein sequestration agent, in part, because of its low immunogenicity. Other proteins, polysaccharides, lipids, polymers, gels and hydrogels that are potentially suitable as sequestration agents are disclosed in U.S. Pat. No. 4,861,627, which is incorporated herein by reference in its entirety. Methods of using and making protein microspheres, including albumin microspheres, are disclosed in U.S. Pat. Nos. 6,620,617; 6,210,707; 6,100,306; and 5,069,936 which are each incorporated herein by reference in their entirety.

D. Sequestration.

The concept of sequestration has been used by the inventor to explain altered lidocaine toxicity when periocular injections are given in the absence of Wydase. (Troll et al. (1999) Diplopia after cataract surgery using 4% lidocaine in the absence of Wydase™. *Clin Anesth.* 11(7): 615-6). Diffusion, in the absence of Wydase, of injectable lidocaine in this circumstance causes toxicity of myofibrils of the extra-ocular muscles with contraction scarring and damage to extra-ocular movement. The lidocaine example indicates how sequestration from dynamic diffusion of an injectable drug can be important to the drug's basic pharmacology.

There has, however, never been a suggestion or recommendation that albumin can alter regional denervation potency or enhance clinical effects or be used to treat patients not responding to BOTOX®, DYSPORT® or MYOBLOC®. The present invention provides compositions and methods that enhance the clinical effectiveness of *botulinum* toxin pharmaceuticals.

As pointed out in the potency section above, sequestration—the regional containment of chemodenervation—is one of the most important properties of the formulations of the present invention. Minimizing diffusion enhances potency, reduces diffusion associated complications, and reducing *botulinum* toxin antigenicity because lower doses are necessary to achieve a therapeutic effect. Preparations which require higher dosing, that is administration of an increased protein load, are associated with higher rates of immunity (comparing 79-11 original Oculinum Batch to current BOTOX® Batch, MYOBLOC® compared to BOTOX®). Enhanced sequestration allows for lower protein load, less diffusion, and enhanced biologic effect within the region targeted for treatment. The utility of this improved composition is demonstrated by its therapeutic effectiveness when conventional formulations (e.g., BOTOX®, MYOBLOC®) currently in use have failed or given suboptimal results.

E. Dosing of High-Potency *Botulinum* Toxin Formulations.

Isolated type A toxin complex has a specific toxicity of about 2040 $LD_{50}$/ng in 18-22 g Swiss-Webster mice. Specific toxicities of other *C. botulinum* toxin complexes are 40-50 $LD_{50}$/ng for the type B M complex; 10-20 $LD_{50}$/ng for the type $C_1$ M complex; 70-80 $Ld_{50}$/ng for the type D M complex; 10 $Ld_{50}$/ng for the type E M complex; 20-30 $Ld_{50}$/ng for the type F M complex (Sugiyama (1980) *Microbiol. Rev.* 44: 419-448); and 80-90 $Ld_{50}$/ng for the type G complex (Schiavo et al. (1994) *J. Biol. Chem.* 269: 20213-20216).

Type A neurotoxin produced by *C. botulinum* is present as part of a complex of at least seven different noncovalently bound proteins. High quality type A toxin complex has a specific neurotoxicity of 30 $LD_{50}$ Units/nanogram. The purified neurotoxin, that is the neurotoxin that has been chromatographically separated from the other proteins of the toxin complex, has a specific toxicity of between about 100 and 250 $LD_{50}$ Units/nanogram. Clinically, a unit (U) is considered to be 1 $LD_{50}$. One unit of *botulinum* neurotoxin is defined as the $LD_{50}$ upon intraperitoneal injection into female Swiss Webster mice weighing 18-22 grams each, or about 50 picograms a purified *botulinum* neurotoxin (essentially free of *botulinum* toxin complex proteins). (Schantz and Kautter (1978) *Association of Official and Analytical Chemistry* 61: 96; See also, U.S. Pat. No. 5,512,547).

The current commercial type A *botulinum* toxin (BOTOX®) is produced by combining up to 500 ng/ml of type A toxin complex in 5.0 mg/ml human serum albumin (HSA) with 9.0 mg/ml sodium chloride at a pH of 7.3. The pre-lyophilization fluid is reduced to 0.1 ml. After dissolution, 0.1 ml is dried to obtain 100±30 Units of toxin, 0.5 mg of HSA, and 0.9 mg of sodium chloride per vial. This product has a saline concentration of 0.9% when reconstituted in 1.0 ml of water. The original commercial formulation of BOTOX®, which employs the toxin complex, had a specific neurotoxicity of about 2.5 U/ng after drying (Allergan, Inc. of Irvine, Calif.). The considerable loss (up to 90%) of activity during drying causes the formation of inactive toxin (toxoid) that can induce antibody formation. More recently, improvements have been made to raise the specific toxicity of BOTOX® to 18-20 U/ng neurotoxin.

Compositions of *botulinum* toxin that require a lower effective amount to treat particular conditions are particularly desirable, because the administration of *botulinum* toxin has been associated with the development of immunologic resistance. Consequently, this complication requires increased dosing (higher $LD_{50}$ units) to achieve a therapeutically-effective amount of the *botulinum* toxin. Ultimately, immunity renders the use of *botulinum* toxin ineffective.

A composition of Hall-strain-derived *botulinum* toxin was formulated with a specific activity of 20 $LD_{50}$ units/ng toxin and 900 µg human serum albumin to 100 $LD_{50}$ units of *botulinum* toxin (0.11 $LD_{50}$ unit/µg albumin)(US FDA IND 4891). The indication for therapy for this new formulation was aberrant regeneration of the facial nerve with involuntary synkinetic blepharospasm. The study was conducted using between 5 and 15 $LD_{50}$ units of *botulinum* type A toxin formulated with the increased amount of albumin to $LD_{50}$ content.

TABLE 5

Reduction in effective amount of botulinum toxin
using high-albumin botulinum toxin compositions.

| Open-Lable Trials | 15 patients each receiving 5-15 LD$_{50}$ units | 100% demonstrated decreased involuntary movement | No ptosis complication |
|---|---|---|---|
| Double-Blind Placebo Controlled Trials | 30 patients (ratio 1:1 treatment/control) each receiving 15 LD$_{50}$ units | 1. Degree of involuntary movements significantly better than controls. 2. Subjective parameters significantly better than controls | No ptosis complications |

Prior literature has indicated that existing BOTOX® preparations require 20 LD$_{50}$ units to achieve favorable results for this indication. (Borodic et al. (1993) Botulinum Toxin for aberrant facial nerve regeneration. Dose response relationships. *Plastic and Reconstructive Surgery*, (91)6: 1042-1045. 1993). Furthermore, there has been a 20% incidence of ptosis (a diffusion complication) associated with the use of *botulinum* toxin for involuntary blepharospasm, based on a 100 patient study on BOTOX® for the treatment of blepharospasm and using comparable LD$_{50}$ doses (see new batch approval study from Allergan Pharmaceuticals, 1998; incorporated herein by reference in its entirety). Comparing the incidence of this complication in the high-albumin study shown above with the BOTOX® equivalency study (19/99, compared to 0/30, P<0.01, Chi Square), it appears that the high-albumin type A *botulinum* toxin composition required fewer LD$_{50}$ units to achieve acceptable therapeutic results (reduction in effective amount of toxin) arid was associated with limited diffusion into the orbit which frequently results in ptosis. The decreased incidence of this complication indicated sequestration of the effects of *botulinum* toxin was enhanced by the higher albumin content.

In the clinical setting, *botulinum* neurotoxin type A (BOTOX®) is used at doses that vary depending on the clinical indication and the size and type of the muscle being treated. The following dosing ranges exemplify the clinical use of BOTOX®: (1) about 75-125 Units of BOTOX® per intramuscular injection (multiple muscles) to treat cervical dystonia (200-300 Units per injection cycle); (2) 5-10 Units of BOTOX® per intramuscular injection to treat glabellar lines (brow furrows)(20-50 Units per injection cycle)(5 units injected intramuscularly into the procerus muscle and 10 Units injected intramuscularly into each corrugator supercilii muscle, and frontalis and orbicularis muscles); (3) about 30-80 Units of BOTOX® to treat constipation by intrasphincter injection of the puborectalis muscle; (4) about 20-40 Units per muscle of intramuscularly injected BOTOX® to treat blepharospasm by injecting the lateral pre-tarsal orbicularis oculi muscle of the upper lid and the lateral pre-tarsal orbicularis oculi of the lower lid; (5) to treat strabismus, extraocular muscles have been injected intramuscularly with between about 2.5-10 Units of BOTOX®, the amount injected varying based upon both the size of the muscle to be injected and the extent of muscle paralysis desired (i.e. amount of diopter correction desired); and (6) to treat upper limb spasticity following stroke by intramuscular injections of BOTOX® into five different upper limb flexor muscles, as follows: (a) flexor digitorum profundus: 7.5-30 Units; (b) flexor digitorum sublimus: 7.5-30 Units; (c) flexor carpii ulnaris: 10-40 Units; (d) flexor carpii radialis: 15-60 Units; (e) biceps brachii: 50-200 Units. (See, U.S. Pat. No. 6,358,926 (col. 5, lines 18-48); U.S. Patent Publication No. 20020197278).

F. Potency

The potency of a particular *botulinum* toxin preparation or formulation may be determined clinically or in animal models of muscle denervation. Clinically, a first *botulinum* toxin preparation exhibits greater potency than a second preparation when fewer LD$_{50}$ Units of the first preparation are required to achieve a desired therapeutic effect.

In animal models, the potency of a *botulinum* toxin preparation may be determined by measuring the extent of denervation produced when a preparation is administered to a muscle. Post mortem sectioning of rabbit muscle about a site of toxin injection, demonstrates that *botulinum* toxin produces a gradient of denervation similar to that observed in mouse muscle (Duchen (1970) *J. Neurl. Neurosurg.* 33:40-54; *J. Physiol.* (*Lond*) (1969) 204:17-18). The extent of this denervation gradient (a measure of the spread of a given dose of the toxin) is a measure of potency. Animal models for muscle denervation are disclosed and described in U.S. Pat. No. 5,298,019, which is incorporated herein by reference in its entirety.

The *longissimus dorsi* muscle of New Zealand white rabbits is the preferred animal model for determining the denervating potency of a *botulinum* toxin preparation. Denervation may be assessed by any available analytical method. For example, denervation may be determined at various distances from the injection site by post mortem sectioning of the treated muscle and staining for acetylcholinesterase activity. Techniques for acetylcholinesterase-activity staining are described by Karnovsky (See Woolf and Coers, *The Innervation of Muscle*, Charles Thomas Pub, Springfield, Ill., 1959, which is incorporated by reference herein in its entirety). Inhibition of acetylcholine release may also be measured by single-fiber electromyography (See, for example, Sanders et al. (1985) Botulinum Toxin for Blepharospasm, Single Fiber EMG Studies, *Neurology* 35: 271-272). Labeled binding proteins, including polyclonal or monoclonal antibodies, may also be used to detect acetylcholinesterase, acetylcholine receptors, and acetylcholinesterase activity. Binding proteins may be labeled using, for example, fluorescein or other fluorescent moieties, colloidal metallic particles, other remotely-detectable substances, and the like. Antibodies can be produced, using known techniques, to acetylcholine receptors or to acetylcholinesterase, both of which can serve as a marker for effective denervation, or to epitopes which are newly exposed, or which remain after binding of the toxin to the receptor on the presynaptic motor end plate. Other stains such as hematoxylin, eosin, masson trichrome, and the like may also be used.

G. Neuromuscular Disorders

The *botulinum* toxin formulations of the present invention may be used to treat a variety of neuromuscular disorders that are characterized by involuntary muscle contractions and/or spasms. These neuromuscular disorders include, but are not limited to dystonias, including cervical dystonia (spasmodic torticollis), spasmodic dysphonia, hemifacial spasm, blepharospasm, bruxism, and spasticity caused by cerebral palsy, stroke, and the like.

Cervical dystonia or spasmodic torticollis is a focal dystonia characterized by neck muscles contracting involuntarily, causing abnormal movements and posture of the head and neck. The abnormal movements and spasms may occur in any direction. Contractions producing forward movements are frequently referred to as anterocollis, whereas spasm that produce backwards or sideways movements are referred to as retrocollis and torticollis, respectively. The movements may be sustained or sporadic. Sustained contractions produce abnormal head and neck posture, whereas periodic spasm produce jerky head movements. The spasms and muscle contractions that produce cervical dystonia are also associated with considerable neck pain and discomfort.

The cause of cervical dystonia is unknown, but is believed to be associated with defects in the basal ganglia which control movement. Although a dopamine deficiency or imbalance may be the underlying chemical basis for the disorder, the exact etiology of cervical dystonia remains unknown. Cervical dystonia may be diagnosed through a medical history, physical and neurological examination. Currently, there is no laboratory or clinical test to confirm a diagnosis of blepharospasm.

Cervical dystonias usually increase in severity, reaching a plateau and remaining stable within five years after onset. This form is unlikely to spread or become generalized dystonia, though patients with generalized dystonia may also have cervical dystonia. Occasionally, there may be associated focal dystonia. Cervical dystonia should not be confused with other conditions which cause a twisted neck such as local orthopedic, congenital problems of the neck, ophthalmologic conditions where the head tilts to compensate for double vision. It is sometimes misdiagnosed as stiff neck, arthritis, or wry neck.

*Botulinum* toxin injections are the primary and most effective form of treatment for cervical dystonia. Injections are made directly into the affected neck muscles. A crucial element to successful *botulinum* toxin injections is that the appropriate muscles are injected. For example, the muscles most commonly involved in cervical dystonia include the splenius capitis, the levator scapulae, upper trapezius, sternocleidomastoid, anterior, middle and posterior scalene. The Dystonia Medical Research Foundation, for example, recommends low-dose (about 150 U BOTOX®) administration of *botulinum* toxin to avoid immunity. Single and especially chronic dosing with greater than 200 U BOTOX® greatly increases the risk of inducing the production of neutralizing antibodies and resistance to the toxin.

H. Neurosensory Disorders (Pain)

The *botulinum* toxin formulations of the present invention may also be used to treat a variety of sensory disorders such as pain syndromes, including myofascial pain, migraine, tension headaches, post-operative wound pain, nerve compression, neuralgias, trigeminal neuralgia, pain associated with cervical dystonia and other dystonias, neuropathy, and sinusitis-related facial pain.

Sinus-related headaches are distinctly different from migraine headache, myofascial headaches, and headaches associated with bruxism, temporal mandibular joint syndrome (TMJ) and temporal mandibular muscle dysfunction (TMD), trigeminal neuralgia, tooth related facial pain, pain associated with elevated intraocular pressure, or internal ocular inflammation. Sinus headaches are associated with pressure, or irritating processes within the sinus cavities, sometimes associated with inflammation and impaired flow of mucous secretion. At some point in the diagnostic workup, excessive signs of inflammation within the sinus or nasal cavity, or edema within the sinus or nasal cavity is demonstrated on exam or via radiographic methods. The present inventors have discovered that *botulinum* toxin relieves the headache and facial pain associated with sinusitis.

The present invention provides methods of treating headache and facial pain associated with acute recurrent or chronic sinusitis in a subject in need thereof, comprising the step of administering a therapeutically effective amount of a composition comprising *botulinum* toxin to the nasal mucosa or to the subcutaneous structures overlying the sinuses, wherein the administration of the composition reduces the headache and facial pain associated with acute recurrent or chronic sinusitis. In a preferred embodiment, the sinuses are one or more of the sinuses selected from the group consisting of: ethmoid; maxillary; mastoid; frontal; and sphenoid. Preferably, the subcutaneous structures overlying the sinuses lie within one or more of the areas selected from the group consisting of: forehead; malar; temporal; post auricular; and lip.

*Botulinum* toxin may be administered to the nasal mucosa or to the subcutaneous structures overlying the sinuses by any number of methods. Preferably, the composition comprising *botulinum* toxin is administered by injection at one or more injection sites. More preferably, the composition comprising *botulinum* toxin is administered to the cutaneous projections of the trigeminal nerve innervating the sinus.

In one embodiment of the present invention, a subject is treated by administration of a composition comprising *botulinum* toxin, wherein the subject, prior to the onset of facial pain or headache, exhibits symptoms or history of sinus rhinorrhea (nasal hypersecretion) and purulent nasal discharge.

Sinusitis is defined as any inflammatory pathology involving the ethmoid, maxillary, frontal, or sphenoid sinuses. It is generally accepted that the cause of pain occurring with acute sinusitis involves infiltration of sinus mucosa with inflammatory cells, as well as increased pressure within the sinuses. What is generally not appreciated, and is herein disclosed, is that sinusitis can cause sensitization of the trigeminal nerve in cutaneous and subcutaneous tissues overlaying the sinus structures. When sensitization of sensory nerves occurs from repeated bouts of sinusitis, the patient can experience a chronic facial pain syndrome or headache. The mechanism by which sensory nerves become up-regulated or sensitized still is not clear. Nerve sensitization is provoked by alterations in the afferent first-order-sensory nervous system, such that thresholds are lowered to the perception of pain (hyperalgesia) and central second-order or higher-neuronal alterations can occur, resulting in an exaggerated response and interpretation of sensory stimuli (central sensitization). This process has been experimentally associated with increased expression and/or responsiveness of NMDA receptors on membranes of nociceptors and possible alterations in transcription and translation of proteins within the nerve cell. The trigeminal ganglia represent a very large collection of afferent sensory neurons, which send projects not only into cutaneous regions of the head, but also internally into osseous sinus structures, and mucous membranes of the nasal and sinus cavities.

The arborization pattern of afferent sensory nerve distribution is extensive, but reactivity within any region of the afferent sensory nerve distribution has the capability of altering the genetic and cellular-protein expression of the sensory nerve cell body within the ganglion. The process of changing cell physiology has been variously coined neuroplasticity or sensitization. Alterations can be in the form of increased expression of nerve cell receptors, such as AMPA and NMDA receptors, modulation of effectors of inflammation, alteration of cellular responses from blood-vessel neural regulation via nitric oxide, substance P, histamine, CRGP, prostaglandins, other known cellular autocoids, and not yet defined autocoids and neuropeptides. The mechanism for sensitization of human nerve cells is still not well understood, and invoking inflammatory mediators, neurogenic inflammatory autocoids, and transcriptional and phenotypic changes of nociceptors and sensory neurons as the only mechanisms for nerve sensitization is not necessary to elicit responses from therapeutic *botulinum* toxin for this indication. Sensitization in the periphery is thought to occur following a sufficient or prolonged exposure to inflammatory substances, causing altered physiology, possible conformational changes of certain biochemical receptors, responsiveness, and lowered thresholds for nociceptor and sensory nerve depolarization.

Sinus pain usually begins in the mid facial region over the maxillary sinus and can radiate to temporal regions, ocular regions, vertex, and over the forehead. At times, referred pain can project into the posterior cervical region or peri-auricular areas. Generalized headaches can occur. The trigeminal nucleus is somatotropically well organized, and from the brain stem area, directly extends and connects anatomically to the upper-cervical areas of the dorsal horn of the spinal cord. In addition, there are interneuronal connections between the trigeminal nucleus and other cranial nerve nuclei, the autonomic nervous system, the reticular activating system, and other descending and ascending pathways. This interconnecting system has been described as the trigeminal sensory complex. Since there are many more peripheral upper cervical and trigeminal sensory nerves synapsing on fewer central nerves, this has been described as convergence and projection. This can explain the referral patterns of head and neck pains, and the therapies employed in one area of the head and neck to affect an outcome on a another area of the head and neck with shared and referred sensory pathways.

Distinct differences in headache diagnosis have been formulated at international conventions and remain the basis for both general and research practice. For migraine headaches, the presence of episodic headaches lasting 4-48 hrs, associated with light sensitivity (photophobia), sound sensitivity (phonophobia), nausea or vomiting, pain of a throbbing or pulsating quality, and more often unilateral than bilateral location of headache. Cluster headaches can be associated with some basal transient nasal congestion but occur over a distinct time period (cluster period) and are not associated with any persistent sinus abnormalities on MRI or computerized tomography. Myofascial and tension headaches often have a cap-like squeezing pain across and around the top of the head, often associated with a cervical musculoskeletal pain location, frequently associated with trigger points, and sometimes associated with decreased jaw motility and bruxism if the masseter and temporalis muscles are involved. Ocular-related headaches are associated with increased intraocular pressure or signs of intra-ocular inflammation on slit lamp microscopic exam or measured refractive error. Dental-related headaches are associated with findings on dental examination and radiographs. Trigeminal neuralgia is usually limited to one or two dermatomes and is sharp and stabbing in quality, with a rapid "on-off" episodic pattern sometimes associated with stimulation of trigger points.

Chronic-sinusitis-related headache and facial pain can linger for many months to years after an acute or subacute bout of sinus disease or bout of repeated acute sinus headaches. Often, the patient complains of continued pain when radiologic imaging studies, such as computerized tomography and magnetic resonance imaging fail to show any persisting signs of inflammation such as mucosal thickening or fluid accumulation. Often out of desperation, the surgeon performs decompressive surgery via endoscopes or direct approaches (Culdwell luc, external ethmoidectomy) with poor results with respect to the chronic pain. The above observation explains a very common clinical. phenomenon associated with chronic facial pain and headache caused by sinusitis. The reason for the persisting pain despite the absence of active sinus findings is peripheral sensory nerve upregulation or sensitization. Direct treatment of sinus-related headache by *botulinum* toxin injected into the subcutaneous region to down-regulate sensory nerves is therapeutic.

The convention in treating sinus-related headaches involves decongestants to augment mucous clearance and drainage from sinus cavities, antibiotics to treat bacterial infection, anti-inflammatory medication (e.g. corticosteroids), and surgical decompression. Conventional analgesics such as aspirin and acetaminophen may be used. The present inventors have made the unexpected discovery that administration of *botulinum* toxin over the surface dermatomes containing the sensory branches corresponding to the neurons projecting into the sinus cavity effectively treats facial and headache pain associated with sinusitis.

A convention held in 1985 by the International Headache Society (I.H.S.) put forth an exhaustive classification of distinct headache syndromes. Experts in the headache therapeutic field formulated this classification, and such experts explicitly agreed on the importance of headache distinction both for practice and research. The reasons for distinctions are to promote better communication among practitioners and to provide more exacting therapy for specific headache syndromes. For instance, procedures used to treat trigeminal neuralgia, such as glycerol injections, gamma knife application, and microvascular decompression at the level of the brainstem are not effective for the treatment of recurrent sinus headache. Tryptin-related pharmaceuticals (e.g. Imitrex™, Zomig™)) would be ineffective for the treatment of sinus headache and laser iridectomy for the treatment of narrow angle glaucoma would be ineffective for the treatment of migraine. Cluster headache needs to be distinguished from migraine. Hence, one skilled in the art of treatment of pain would require specific and professionally acceptable diagnosis in order to recommend reasonable therapy or to conduct clinical trials with potentially effective new therapies. The convention held in 1985 and subsequently published in Cephalgia (1988 Vol 8 (supplement 7), 1-96) has served as a benchmark for diagnosis and classification of human headaches (nosology) for the past 15 years.

In order for the physician to function and recommend therapeutic interaction with patients suffering from pain, classification with diagnostic criteria of an affliction must be determined. Classification of disease must be operationally specified with quantitative parameters and not just descriptive. The International Headache Society (I.H.S.) formed a committee in 1995 which lead to the first adopted international headache classification, which in turn permitted uniform operational criteria for diagnosis. The I.H.S. is internationally accepted and has been incorporated into the World Health Organization (W.H.O.) classification of disease. This classification has been translated into multiple languages and competes with no other classification system (see Jes Olesen Classification of Headache in Chapter 2, The Headaches, $2^{nd}$ Edition, Lippincott, Williams and Wilkins ed Olesen, Hansen, Walsh, Philadelphia, 1999).

In the classification system, headaches in category 1-4 are primary headache disorders with no associated anatomic pathologic process. Groups 5-11 are headaches and cervical pain associated with some other demonstrable disease process (trauma, vascular disease, increased intracranial pressure, withdrawal from substances, systemic infection, metabolic disorder, eye, ear, nose, and throat disease, or dental disease. Group 12 relates to cranial neuralgias.

I. Inflammation

Inflammation is a normal response to tissue damage. Inflammation is often characterized by edema, erythema and pain. Acute inflammation may caused by a variety of injury, including physical and chemical injury and tissue damage caused by microorganisms and other agents. The inflammatory response consist of changes in blood flow, increased permeability of blood vessels and the escape of cells from the blood into the tissues.

Acute inflammation is short-lasting, lasting only a few days. Chronic inflammation is characterized by a longer duration. Examples of acute inflammation include hives, swelling, itching and pain associated with insect bites, burns or exposure to a chemical agent or allergen. Inflammatory conditions may also affect internal organs such as the lungs, gastrointestinal tract, heart, kidneys and the like.

Disease known to be inflammation driven in etiology include rheumatoid arthritis, inflammatory bowel disease, Crohn's Disease, interstitial cystitis, eczema, hay fever, inclusion arthritis, myositis, post surgical inflammatory states, reflex sympathetic dystrophy, arteritis, nephritis, scleroderma, asthma, prostatitis, sarcoidosis, bacterial infections, seborrhea, acne, osteomyleotitis, wound healing sites, systemic lupus erythematosis, Stevens Johnson syndrome, cutaneous and deep burns, myofascial pain syndromes, osteoarthritis, conjunctitis, blepharitis, uveitis, sialoadenitis, gastritis, tendonitis, keratitis, and post traumatic tissue damage, and the like.

*Botulinum* toxin in doses lower than that necessary to treat regional movement disorders has been shown to reduce inflammation and adverse sensory experiences associated with the inflammatory response. These observations are explained by the fact that it has been found that low dosages of the subject chemodenervative agent reduces histamine releases and releases of other preformed mediators associated with mast cell degranulation. The anti-inflammatory activity is observed at low doses in animal models for ocular surface disease that are well noted for histamine release and release of other preformed mediators associated with mast cell degranulation and rapid inflammatory response. Accordingly, *botulinum* toxin blocks edema, erythema, abnormal sensory experiences, and heat transfer that occur rapidly over a predefined region.

The anti-inflammatory action of *botulinum* toxin is explained by the resultant blockage of mast and nerve cell release of histamine and other preformed mediators which result in vascular dilation, increased permeability, altered sensory experience, edema and erythema—the hallmarks of the rapid-phase inflammatory response. It will be appreciated that mast cells are known to contain a number of substances important to inflammatory responses in hypersensitivity reactions, and substantially participate in more generalized inflammatory reactions. The mast cell is abundantly found in pathologic tissue specimens in patients with rheumatoid arthritis, inflammatory bowel disease, certain forms of ocular uveitis, eczema, and asthma.

Mast cell activation has been associated with the production of both preformed mediators such as histamine, newly formed mediators such as leukotrienes and prostaglandins, cytokines, including interleukin-5, interleukin-8, kininogenase, and platelet activating factor. A number of these mast cell constituents play a role in the inflammatory response functioning as chemoattractants, activators and spasmogens. Additionally, a number of these constituents are activated and released in response to neural stimulation and play a role in neural sensory adaptation systems. Histamine is well known to produce itching sensation causing a compulsion to scratch or stimulate the activated area. Histamine also causes pain in patients with genetic predisposition to develop essential headaches.

An especially important cytokine identified as being important to inflammation and pain is tumor necrosis factor alpha. Tumor necrosis factor alpha has been identified in activated mast cells, and plays a role in modulation of mast cell activity. (Cocchiara et al. (1999) Histamine and Tumor Necrosis Factor-alpha Production from Purified Rat Brain Mast Cells Mediated by Substance P. *Neuroreport* 10(3):575-8; Olejnik et al. (1998) Tumor Necrosis Factor Alpha (TNF-alpha) Modulates Rat Mast Cell Reactivity. *Immunol. Lett. (*2-3): 167-71). Anti-tumor necrosis factor, as well as other pre-formed and newly formed mediators are autocoids which are reduced when suppressing mast-cell releases.

The *botulinum* toxin formulations of the instant invention are given in a therapeutically effective dose to reduce inflammation, and may be used in any application in which inflammation is present or to augment other inflammatory agents. The administration may be by injection, topical application, or other means to assure a therapeutically effective dose delivered to the site. Not only is the subject treatment efficacious in disease treatment normally associated with the occurrence of inflammation, it is also efficacious in the treatment of other diseases. Note that mechanical or adjuvant chemical activity may be necessary to increase penetration by topical application.

Urticaria refers to the formation of hives occurring usually in response to allergic reactions to pollens, foods, dander or other forms of antigens. The process often involves binding of allergens to the IgE receptor of the mast cell membrane bound IgE, causing release of preformed mediators such as histamine and serotonin as well as newly formed mediators from arachadonic acid such as prostaglandins and leukotrienes, platelet activating factor, kinoginase and tryptase, as well as cytokines. A late response can be seen after an allergic urticaria reaction which may be painful.

Urticaria may be provoked by non-allergens, including codeine, morphine, compound 48/80, synthetic ACTH, and anaphylatoxins C3a, C5a. Important, relative to the case observation, is the reactivity of mast cells to acetylcholine. (Fantozzi et al. (1978) Release of Histamine from Rat Mass Cells by Acetycholine. *Nature* 273 (5662): 473-4).

Mast cells are known to be abundant around blood vessels in the scalp, orbit and lids, and are thought to be important in allergic conjunctivitis. (Allensmith et al. (1981) Percentage of Degranulated Mast Cells in Vernal and Giant Papillary Conjunctivitis. *Am. J. Ophthalmol.* 9: 71-75; Henriquez et al.

(1981) Mast Cell Ultrastructure, Comparison in Contact Lens-associates Giant Papillary Conjunctivitis and Vernal Conjunctivitis. *Arch. Ophthalmol.* 99: 1266-1272). Mast cell reactivity has been associated with hayfever blepharoconjunctivitis, asthma, allergic rhinitis, and allergic forms of eczema. Mast cells are also seen abundantly in inflammatory responses in rheumatoid arthritis and inflammatory bowel disease.

Mast cells are closely associated with Type-1 hypersensitivity reactions. In such reactions, the typical response involves sensitization with an antigen, formation of immunoglobulin, IgE class, binding of immunoglobulin to the external cell membrane by its FcE receptor, and setting the stage for hypersensitivity to the second exposure to the antigen. Upon second exposure, IgE reacts with the antigen effect in a degranulation response of the mast cell, in which there is a release of preformed mediators such as histamine and serotonin, platelet activating factor, and newly formed mediators such as leukotrienes, prostaglandins, tryptase, kininogenase which effect vasodilatation, vascular permeability, micro thrombi, edema, mucous secretion. The response persists manifesting a late response after 8 hours. The late response is associated with pain as described by Roit, I., Brostoff, J., Male, D., Immunology $5^{th}$ Edition Mosby, 1998.

Internal inflammatory diseases may also be treated with *botulinum* toxin. In the past, it was thought that the tissue mechanisms associated with using chemodenervating agents have solely involved the use of *botulinum* toxin as a means of causing muscle relaxation or to produce certain autonomic effects blocking decreased sweating. Although there have been conditions treated by chemodenervating agents which have had associated inflammatory reaction as a part of the clinical syndrome, the concept of muscle relaxation induced by such agents has been thought to be the mechanism by which such agents induce the beneficial effects. It has now been found that the subject agent has useful anti-inflammatory properties capable of blocking ocular surface allergic inflammation in man and animal models, as well as generalized inflammation within the denervation field created.

For treatment, the practitioner defines a fixed anatomic area in which symptomatic and/or destructive inflammatory processes are occurring. Knowledgeable of dose related diffusion properties and potency of the preparation being used, the practitioner defines the anatomic area to be treated. Avoiding critical structures, e.g. blood vessels, nerves and anatomic cavities, the practitioner injects a fixed dosage of the chemodenervating agent so as to create a denervation field reducing the intensity of tissue destruction occurring within the area of treatment. Such a field can be defined internally, e.g. stomach mucosae-gastrits, joint-arthritis and muscle myositis. Follow-up involves monitoring for the cardinal sign of inflammation-pain redness, edema and discharge. Adjuvant therapy with other anti-inflammatory agents would be contemplated.

One of the most devastating chronic internal inflammatory diseases is rheumatoid arthritis, characterized by joint and periocular involvement and chronic inflammatory causing destruction of cartilage and ligamentous structures involving joints throughout the body. Immunologic causes have been cited as the underlying pathologic mechanism of the chronic destructive process, and mast cells have been noted in large quantities within the tissue pannus surrounding joints afflicted. Edema, joint effusions, stiffness, spasms, pain, and erythema, are all components of the arthritis involved regions. Multiple anti-inflammatory agents have been tried, with variable results to suppress the destructive effects of this systemic disease on bone and joints.

The formulations of the instant invention offer a means of localized application of an anti-inflammatory agent which is injected directly into joints or perarticular muscular tissues which creates an effect on the rapid inflammatory response and peripheral neural elements governing the inflammatory response. The application may be repeated at 3-month intervals and at titrated doses by clinical methods so as to limit any weakness within the injected region.

J. Cosmetic Applications

Lines and wrinkles of the skin are the products of multiple causes that reduce the collagen and fat content of the skin, including aging and sun exposure. Aging produces wrinkles that may be characterized as fine lines that disappear when the skin is stretched. Wrinkles and lines resulting from sun damage are coarser and deeper and do not disappear when the skin is stretched. The treatment for wrinkles varies with the degree of severity.

In some cosmetic applications, the *botulinum* toxin formulations of the present invention may be administered to the muscles of the face, including the forehead and eye area, to reduce lines and wrinkles. The disclosed *botulinum* toxin formulations may be administered through a variety of modalities including surface application, subcutaneous and intramuscular injection. Specifically, *botulinum* toxin may be used, for example, to treat glabellar frown lines, crow's feet, horizontal forehead lines, nasolabial fold, mental crease, upper lip, platysmal bands, horizontal neck lines and wrinkles of the lower part of the face. Generally, one to five injections are given per muscle. The selection of muscles and the number of injections per muscle, however, depend on the desired effect and the severity of the lines and wrinkles and are within the skill of the treating physician. Administration of *botulinum* toxin produces smoothing of the skin and reduction of fine lines and superficial wrinkles in the area of treatment.

The *botulinum* toxin formulations of the present invention are particularly suitable for use in methods for cosmetically modifying soft-tissue features. In particular, these soft tissue features are features of the face and neck. For example, the disclosed formulations may be used to alter the shape and volume of facial features such as the lips. Hypervolemic lips, for example, are anatomically caused by one or more of the following structural deviations: 1) excessive tone of lip retractor function of the certain facial muscles such as levator labii superioris, zygomaticus major and minor, levator labii inferioris, platysma, and depressor labii inferioris; excessive prominence and development of orbicularis oris muscle; and excessive non-muscular soft tissue volume within the lip itself. As a consequence of the long duration of *botulinum*-toxin-induced neuromuscular blockade, catabolism occurs within the innervated, striated muscle that produces shrinkage of muscle fiber and decreased muscle bulk and size. Consequently, administration of the disclosed formulations to muscles of the lip provide a method to reduce the shape and volume of the lips. The formulations disclosed herein, may be injected one or more locations and muscles to produce cosmetic modification of the soft tissue in the area of administration. Multiple administration of *botulinum* toxin may be required to achieve the desired degree of muscle shrinkage and the cosmetic modification of soft tissues.

K. Cutaneous Disorders

The *botulinum* toxin formulations of the present invention may also-be used to treat a variety of cutaneous disorders, including hypersecretion disorders of the meibomian glands (chalazion), sebaceous glands (hordeola) and sweat glands (hyperhydrosis). Chalazion is a chronic granulomatous enlargement of a meibomian gland of the eyelid. This disorder is characterized by hypersecretion of meibum from the meibomian glands. This hypersecretion leads to an accumulation of fatty materials that that form lesions that occlude the ductal elements of the gland, leading to an encroachment of the occlusion into the surrounding tissue, which further induces an inflammatory response. Similarly, hordeola is characterized by hypersecretion of sebum from sebaceous glands. Individuals suffering from Chalazia and/or hordeola are often treated by warm compresses or lid soaps which mechanically remove the excess secretion. This approach is often ineffective. The use of antibacterial eyedrops are occasionally effective, but rarely cure the underlying problem—hypersecretion of the meibomian and sebaceous glands that causes inflammation. Patients usually undergo multiple surgical procedures to remove fatty secretions and associated inflammatory cells within the glands to effect relief. Such procedures are painful and occasionally result in lid scarring and misdirection of the eyelashes. The present invention, however, provides an improved method of treating subjects suffering from Chalazion, hordeola and cutaneous infections, comprising the administration of *botulinum* toxin to reduce or prevent the secretion of meibum and sebum from meibomian and sebaceous glands, respectively.

Chalazia occurs as a chronic deep inflammation of the lid associated with the accumulation of lipid material within macrophages (epithelioid cells) surrounding meibomian glands within the tarsal plate of the eyelid. The inflammation is characterized as a granulomatous-type inflammation associated with lipid and cellular lesions within soft tissues. In the case of chalazia, the lesions are formed by the secretion of the meibomian glands, the glands which contribute to the outer layers of the tear film covering the ocular surface. Histological analysis of these lesions reveal clear regions representing the lipid material, surrounded by polymorphonuclear leukocytes, plasma cells, giant cells, and lymphocytes.

Hordeola presents a similar pathologic process, however, these lesions occur from occluded sebaceous glands at the extreme of the eyelid margin. The resulting occlusion and excess sebum produces an inflammatory reaction similar to that observed in chalazion.

Chalazion formation has been associated with hypersecretion of the lipid-rich meibum from the meibomian gland. Alterations in the lipid composition of meibomian secretions, including free fatty acid and cholesterol content, have also been linked to Chalazion, producing tear film instability, irritation of conjunctival and corneal epithelium, and increased susceptibility to bacterial and fungal infections. Although numerous organism have been identified in the infections frequently associated with Chalazion, the most common isolated bacteria from blepharitic eyelids include species of *Staphylococcus, Corynebacterium*, and *Proprionibacterium*. *Staphylococcus aureus* has been thought to flourish on hypersecretion of meibomian and related eyelid glands. In summary, the pathophysiology of chalazia and hordeola involves: 1) altered meibomian secretion and hypersecretion; 2) inflammation from secretion backup into soft tissue of the lid; and 3) secondary inflammation.

The methods of the present invention may also be used to treat pathology associated with the occlusion of sebaceous gland ducts, and the resultant inflammation and infection in areas other than the eyelid (e.g. folliculitis).

The present invention also provides methods of treating a bacterial or fungal cutaneous infection in a subject in need thereof, comprising the step of administering a therapeutically effective amount of a composition comprising *botulinum* toxin to the subject, wherein the composition reduces cutaneous bacterial or fungal growth. In one embodiment, the infection is caused by an organism selected from the group consisting of: *Staphylococcus; Streptococcus* and *Moraxella*. Preferably, the methods of the present invention treat bacterial of fungal cutaneous infections in the eyelid, scalp, feet, groin, and armpit.

The present invention also provides methods of reducing a sebaceous or mucous secretion on a body surface in a subject in need thereof, comprising the step of administering a therapeutically effective amount of a composition comprising *botulinum* toxin to the subject, wherein the composition reduces sebaceous or mucous secretion.

EXAMPLES

The following Examples serve to further illustrate the present invention and are not to be construed as limiting its scope in any way.

Example 1

Treatment of Blepharospasm

The subject is a 52-year-old female with severe bilateral involuntary blepharospasm. Involuntary movements have prevented her from driving and maintaining gainful employment. BOTOX® was administered by injection on five separate occasions without producing any significant clinical improvement. Surgery was performed to remove a portion of the protractors of eyelid closure (orbicularis oculii). No lasting improvement was observed.

The albumin content of the BOTOX® was altered by adding 5,000 µg human serum albumin to a vial of BOTOX® (100 $LD_{50}$ units). The resulting composition has an albumin concentration of 2,750 µg/cc (0.018 $LD_{50}$/µg albumin). Administration of 60 $LD_{50}$ units of the high-albumin preparation produced a nearly complete resolution of symptoms. The high-albumin concentration was clinically effective even when used in subsequent administrations (4 injection cycles) for over two years.

Example 2

Treatment of Hemifacial Spasm

The subject is a 62-year-old male with a history of bilateral hemifacial spasm. *Botulinum*-toxin therapy using BOTOX® had been ineffective. The spasms impaired his day to day ability to function. Decompression of a facial nerve was attempted surgically on two separate occasions. Both surgeries proved ineffective in attaining acceptable relief of involuntary facial spasms and produced deafness in one ear.

The albumin content of the BOTOX® was increased by adding human serum albumin sufficient to achieve a concentration of 5,250 µg/cc (0.00952 $LD_{50}$/µg albumin). Administration of 30 $LD_{50}$ units of the high-albumin preparation proved highly effective and substantially relieved the clinical symptoms.

Example 3

Treatment of Hemifacial Spasm

The subject is a 66-year-old man with right hemifacial spasm. Although he was successfully treated with BOTOX® for 11 years, resistance developed that rendered further injections ineffective. Immunologic-resistance testing, using a remote point injection, demonstrated an absence of circulating antibody. A trial of another *botulinum* toxin formulation, MYOBLOC®, was also ineffective at relieving signs and symptoms.

The albumin content of BOTOX® was increased by adding human serum albumin sufficient to achieve a concentration of 5,250 µg/cc (0.00952 $LD_{50}$/µg albumin). Administration of 40 $LD_{50}$ units of the high-albumin preparation proved highly effective and substantially relieved the clinical symptoms.

Example 4

Treatment of Benign Essential Blepharospasm

The subject is a 72-year-old university president who was diagnosed with benign essential blepharospasm. Four prior injections of the standard BOTOX® preparation failed to achieve any significant improvement. The subject was referred for possible surgical removal of muscle and nerve to weaken muscles necessary for eyelid closure. Instead, a high-albumin preparation of *botulinum* toxin was administered to the usual injections sites that are specific for benign essential blepharospasm. The high-albumin preparation was produced by adding 12,250 µg/cc (0.004 $LD_{50}$/µg albumin). Administration of 60 $LD_{50}$ units of the high-albumin preparation achieved excellent results when the administration of the conventional BOTOX® formulation had failed. Three months after the initial administration of the high-albumin *botulinum* toxin preparation, 40 $LD_{50}$ units of a high-albumin preparation comprising 25,000 µg albumin per 100 $LD_{50}$ units (0.002 $LD_{50}$/µg albumin) were administered and produced greater than 80% relief of the clinical symptoms of blepharospasm.

Example 5

Treatment of Blepharospasm

The subject is a 67-year-old female with blepharospasm that was not responsive to BOTOX® injections. Surgical removal of nerve and muscle failed to provide any relief from involuntary eyelid closures.

Albumin was added to a conventional BOTOX® preparation to produce a high-albumin preparation of *botulinum* toxin with a concentration of 50,250 µg albumin/cc (0.001 $LD_{50}$/µg albumin). Injection of 50 units the high-albumin preparation produced a greater than 50% reduction of symptoms.

Example 6

Treatment of Blepharospasm

The subject is a 77-year-old male who noted tachyphylaxis following repeated *botulinum* toxin injections. Conventional formulations of *botulinum* toxin type B were injected without relief of blepharospasm.

Human serum albumin and 0.5 cc Healone (hyaluronate) were both added to a 100 $LD_{50}$ units of *botulinum* toxin type A (BOTOX®). The high-albumin preparation produced contained 25,500 µg albumin per 100 $LD_{50}$ units (0.005 $LD_{50}$/µg albumin). Administration of 60 $LD_{50}$ units reduced the clinically-observed involuntary-eyelid contractions.

Example 7

Treatment of Essential Blepharospasm

The subject was a 66-year-old female with essential blepharospasm. Repeated treatment with BOTOX® (type A), using a range between 40 to 300 $LD_{50}$ units, produced no therapeutic benefit. *Botulinum* toxin type B (MYOBLOC®) was administered at a dose of 10,000 $LD_{50}$ units within the periocular region and also failed to produce any relief. Bilateral-facial neurectomy also failed to produce any substantial relief of symptoms. Additional surgical procedures to remove muscles necessary for eyelid closure were similarly ineffective.

Human serum albumin was added to a 100 $LD_{50}$ units of *botulinum* toxin type A (BOTOX®). The high-albumin preparation produced contained 12,750 µg albumin per 100 $LD_{50}$ units (0.00196 $LD_{50}$/µg albumin). Administration of 50 $LD_{50}$ units produced substantial relief of symptoms for a period of three to four months, when other formulations and surgical approaches had failed.

Example 8

Treatment of Severe Chronic Blepharospasm

The subject is an 83-year-old male with severe chronic blepharospasm. The subject had developed ptosis, a diffusion side effect, after repeated treatments with therapeutic doses of conventional *botulinum* toxin formulations. The emergence of ptosis complicated the treatment of this subject by requiring lower doses of *botulinum* toxin. The lower dosing proved less effective.

The patient received an a high-albumin formulation of *botulinum* toxin that was produced by mixing 25,000 µg human serum albumin 100 $LD_{50}$ units of BOTOX®. The high-albumin preparation contained 12,750 µg albumin per cc (0.004 $LD_{50}$/µg albumin). Using the high-albumin preparation, 60-70 $LD_{50}$ units were administered with excellent clinical results and no evidence of ptosis after the therapy. The enhanced sequestration of much higher concentrations of *botulinum* toxin depressed the spread of the neurotoxin into the muscles within the eye socket.

Example 9

Treatment of Essential Blepharospasm

The subject is a 67-year-old woman with essential blepharospasm. The subject underwent treatment with conventional formulations of *botulinum* toxin without relief. In addition, these treatments produced ptosis.

A high-albumin *botulinum* toxin composition (20,000 µg albumin per cc; 0.0025 $LD_{50}$ BOTOX®/µg albumin) was administered to the subject with a resultant clinical improvement of the blepharospasm and no diffusion-related side effects (ptosis).

TABLE 4

Comparison of albumin concentrations used in Examples 1-9 with other formulations.

| Example | Albumin Concentration (µg/cc) | High-Albumin Preparation ($LD_{50}$/µg albumin/cc) | BOTOX ® ($LD_{50}$/µg albumin/cc) | DYSPORT ® ($LD_{50}$/µg albumin/cc) | MYOBLOC ® ($LD_{50}$/µg albumin/cc) |
|---|---|---|---|---|---|
| 1 | 2,750 | 0.0180 | 0.2 | 5 | 10 |
| 2 | 5,250 | 0.0095 | 0.2 | 5 | 10 |
| 3 | 5,250 | 0.0095 | 0.2 | 5 | 10 |
| 4 | 12,500 | 0.0040 | 0.2 | 5 | 10 |
|   | 25,000 | 0.0020 |     |   |    |
| 5 | 50,250 | 0.0001 | 0.2 | 5 | 10 |
| 6* | 10,200 | 0.0050 | 0.2 | 5 | 10 |
| 7 | 25,000 | 0.0020 | 0.2 | 5 | 10 |
| 8 | 12,500 | 0.0040 | 0.2 | 5 | 10 |
| 9 | 20,000 | 0.0025 | 0.2 | 5 | 10 |

$LD_{50}$/mcg albumin/cc for BOTOX ®, DYSPORT ®, MYOBLOC ® given for direct comparison

Example 10

Preparation of a High-Albumin Composition of *Botulinum* Toxin

After quantitating the biologic effect by dilution of purified *botulinum* toxin, a quantity of albumin is added to the lyophilized or liquid material in a quantity sufficient to exceed 500 mg per 100 $LD_{50}$. The increased albumin binds to *botulinum* toxin and enhances sequestration of the injected neurotoxin providing for better saturation of neurotoxin receptors and improved clinical effect.

Example 11

Preparation of a High-Albumin Composition of *Botulinum* Toxin further Comprising Hyaluronate After quantitating the biologic effect by dilution of purified *botulinum* toxin, a quantity of albumin is added to the lyophilized material in a quantity sufficient to exceed 500 µg per 100 $LD_{50}$ units. Additionally, another sequestration agent, which further enhances sequestration, is added to keep the *botulinum* neurotoxin from diffusing away from the injections site. Such a sequestration agent includes but is not limited to a diluted solution of sodium hyaluronate. The increased albumin non-covalently binds to *botulinum* toxin and an enhances the sequestration of the neurotoxin providing better saturation of neurotoxin receptors and, consequently, an improved clinical effect.

Example 12

Preparation of a High-Albumin Composition of *Botulinum* Toxin further Comprising Collagen After quantifying the denervating effect of a *botulinum* neurotoxin by dilution of a purified *botulinum* toxin, albumin is mixed with the lyophilized *botulinum* neurotoxin in a quantity sufficient to exceed 500 µg albumin per 100 $LD_{50}$ units. Additionally, another physical agent, which further enhances sequestration, is added to keep *botulinum* neurotoxin from diffusing away from the injections field. Such an agent would be a diluted mixture of animal or human collagen. The increased albumin non-covalently binds *botulinum* toxin, an enhances sequestration of the neurotoxin, providing better neurotoxin receptor saturation and improved clinical effect.

Example 13

Preparation of a High-Albumin Composition of *Botulinum* Toxin Comprising a Recombinantly-Produced *Botulinum* Toxin-Albumin Fusion Protein

*Botulinum* toxin is produced as a fusion protein with albumin thereby producing an albumin molecule that is covalently linked to a *botulinum* toxin. The fusion protein is tested using the mouse $LD_{50}$ bioassay to determine the effective amount. The regional denervation rabbit ptosis bioassay and mouse hindlimb bioassay may be used to confirm the effective amount of a composition comprising the fusion protein. A clinical-dose-escalation study would be further used to confirm and refine effective amount.

Example 14

Resistance to *Botulinum* Toxin after Treatment for Cosmetic Indications

A 44-year-old woman received multiple injections of *botulinum* type A toxin for the effacement of glabellar rhytides and crowsfeet. After 8 injections, she noted the medication no longer was effective. A maximal facial dose of 80 U failed to produce any significant benefit. Substitution of *botulinum* toxin type B caused effacement indicating resistance to *botulinum* type A.

Example 15

Preparation of a High Specific Activity *Botulinum* Toxin Preparation with Increased Potency Per $LD_{50}$ Unit for the Treatment of Facial Rhytides

*Botulinum* toxin formulated as pure neurotoxin (accessory proteins removed and high specific activity of about 80 $LD_{50}$ units per nanogram), 1 mg trehalose, with 4000 mcg of albumin per 100 $LD_{50}$ was used to treat glabellar rhytides injected over 5 sites between and over the eye-brow region in an FDA-approved phase-1-human-clinical trial. The purpose of the study was to determine safety and efficacy using a dose-escalation paradigm. An initial dose of 6.25 U or 1.25 U per injection site (5) was selected. This starting dose (6.25.U per injection cycle) was selected, because it was expected to be below a therapeutically effective dose. The initial dose was chosen by a panel of expert physicians, and was accepted by regulators at the United States Food and Drug Administration as below that necessary to produce any therapeutic effect. Surprisingly, this low dose proved efficacious in about 75-80% of patients, a result unexpected both in view of experience with pre-clinical animal models and prior clinical experience with BOTOX®. The response rates were corroborated by multiple primary endpoints, using both patient and physician assessment. Furthermore, the unexpected favorable response lasted 10 weeks in over 50% of the patients in this dosing cohort, a result similar to a 20 U dose of BOTOX®.

and a grading of "3" is indicative of severe rhytides with respect to depth, extent, and prominence with facial muscles at rest and during forced frown.

A 75% response rate for in patients receiving 6.125 Units was obtained at Day 22 (three weeks) using the physician photo-scale assessment (Table 5A). A 62.5% response rate was to observed by SGA (Table 5B). A significant number of the 6.25 U patients sustained the beneficial effect through at least Day 71 (10 weeks).

The results obtained from this dose escalation study are contrary to expected outcomes based on prior experience with immunotype A *botulinum* neurotoxins formulated with 500 mcg or less human serum albumin per 100 $LD_{50}$ U (such as BOTOX®). The package insert for BOTOX®, representing the results from multiple clinical studies indicates 20 units (4 U per injection site) as the dose sufficient to diminish glabellar rhytides.

TABLE 5

Effect of 6.25 Units of High-Potency Botulinum Toxin Formulation on Treatment of Glabellar Rhytides.

A.

| Subject 6.25 U | Investigator Baseline Rest (R) | Frown (F) | Day 22 R | F | Δ Response (CFB #steps) R | F | Day 29 R | F | Δ Response R | F | Day 71 R | F | Δ Response R | F |
|---|---|---|---|---|---|---|---|---|---|---|---|---|---|---|
| 1101 | 1 | 2 | 1 | 2 | 0 | 0 | 1 | 2 | 0 | 0 | 1 | 2 | 0 | 0 |
| 1102 | 1 | 2 | 1 | 1 | 0 | 1 | 1 | 1 | 0 | 1 | 1 | 1 | 0 | 1 |
| 1103 | 2 | 3 | 2 | 2 | 0 | 1 | 2 | 2 | 0 | 1 | 2 | 2 | 0 | 1 |
| 1104 | 0 | 2 | 0 | 1 | 0 | 1 | 0 | 1 | 0 | 1 | 0 | 1 | 0 | 1 |
| 1105 | 1 | 3 | 1 | 2 | 0 | 1 | 1 | 2 | 0 | 1 | 1 | 2 | 0 | 1 |
| 1106 | 1 | 3 | 1 | 2 | 0 | 1 | 2 | 2 | −1 | 1 | 2 | 2 | 1 | 1 |
| 1107 | 2 | 2 | 2 | 2 | 0 | 0 | 2 | 2 | 0 | 0 | 2 | 2 | 0 | 0 |
| 1108 | 2 | 3 | 2 | 2 | 0 | 1 | 2 | 2 | 0 | 1 | 2 | 2 | 0 | 1 |
| % Primary Endpoint Responders = | | | | | 75 | | | | 75 | | | | 75 | |

B.

| Subject 6.25 | SGA Baseline R | F | Day 22 R | F | Δ Response (% CFB) R | F | Day 29 R | F | Δ Response R | F | Day 71 R | F | Δ Response R | F |
|---|---|---|---|---|---|---|---|---|---|---|---|---|---|---|
| 1101 | 69 | 93 | 19 | 32 | 72.5 | 65.6 | 8 | 31 | 88.4 | 66.7 | 29 | 48 | 57.9 | 48.4 |
| 1102 | 68 | 82 | 3 | 7 | 95.6 | 91.5 | 16 | 19 | 76.5 | 76.8 | 17 | 28 | 75 | 65.9 |
| 1103 | 69 | 89 | 59 | 67 | 14.5 | 24.7 | 63 | 67 | 8.7 | 24.7 | 69 | 76 | 0 | 14.6 |
| 1104 | 45 | 68 | 2 | 2 | 95.6 | 97.1 | 1 | 2 | 97.8 | 97.1 | 8 | 25 | 82.2 | 63.2 |
| 1105 | 55 | 82 | 3 | 25 | 94.5 | 69.5 | 1 | 19 | 98.2 | 76.8 | 22 | 38 | 60 | 53.7 |
| 1106 | 85 | 92 | 56 | 66 | 34.1 | 28.3 | 69 | 69 | 18.8 | 25.0 | 77 | 75 | 9.4 | 18.5 |
| 1107 | 92 | 98 | 72 | 87 | 21.7 | 11.2 | 73 | 88 | 20.7 | 10.2 | 73 | 93 | 20.6 | 5.1 |
| 1108 | 74 | 80 | 28 | 11 | 62.2 | 86.3 | 22 | 10 | 70.3 | 87.5 | 58 | 76 | 21.6 | 5.0 |
| % Primary Endpoint Responders = | | | | | 62.5 | | | | 62.5 | | | | | 37.5 |

Table 5 depicts the data obtained from the administration of the high-albumin formulation of *botulinum* neurotoxin type A to eight patients for the treatment of glabellar rhytides using an FDA-approved human studies protocol to determine safety and efficacy. The response to treatment was measured using a visual, patient-based self-grading assessment (SGA) using an analog scale (0-100 mm) and investigator-based photo-scale grading (FDA-approved primary endpoints for Phase-1 protocol). The visual SGA scale ranges from 0-100 mm. A grading of "0" represents no self-perceived rhytides, whereas a grading of "100" represents a self-perception of extreme or severe rhytides. Grading was done with facial muscles at rest and during a forced frown. The physician photo-scale ranges from 0-3. A grading of "0" indicates no observable rhytides Example 16

Treatment of Rhytides Using a High Specific Neurotoxicity *Botulinum* Toxin Formulation Eight patients interested in having glabellar rhytides effaced were injected with a composition comprising a *botulinum* toxin with a specific activity of about 80 u/ng,. 1 mg trehalose and 4,000 mcg human serum albumin per 100 $LD_{50}$ Units neurotoxin. Patients received 6.125 U total in 5 injection sites (1.25 U per site). Patients were followed for 3, 4 and 10 weeks for safety and efficacy using a visual analog scale for patient global self-assessment and a photo-scale rating severity of rhytides. Surprisingly, the composition described herein produced a substantial improvement within 72 hours of injection with 75%. of cases improved as assessed using a physicians grading scale and over 62% improvement using a patient self assessment scale (p.0.01, compared to saline controls). To achieve similar results, at least 20 U of BOTOX® is necessary.

Example 17

Determining the Immunogenicity of Botulinum Toxin Formulations

A rabbit model has been used to assess the immunogenicity of various toxin preparations. In that model, albino rabbits receive repetitive sublethal injections of various toxin preparations over a period of time. Rabbit serum is assessed for neutralizing *botulinum* toxin antibodies by exposing a *botulinum* toxin to serum from the immunized rabbit and comparing the denervating activity (denervation potency) of equivalent dosages of *botulinum* toxin exposed to the rabbit serum against unexposed *botulinum* toxin. Animal models for muscle denervation are disclosed and described in U.S. Pat. No. 5,298,019, which is incorporated herein by reference in its entirety. An observation of decreased denervation potency, when comparing exposed *botulinum* toxin to the unexposed toxin, indicates that the toxin preparation induced neutralizing antibody formation. Similarly, differences in denervation potency between *botulinum* toxin preparations indicate different immunogenicity of the preparations. Reduced denervation potency is proportional to the immunogenicity of the preparation.

Example 18

Denervation Potency in Rabbit Muscle

Figure 2:
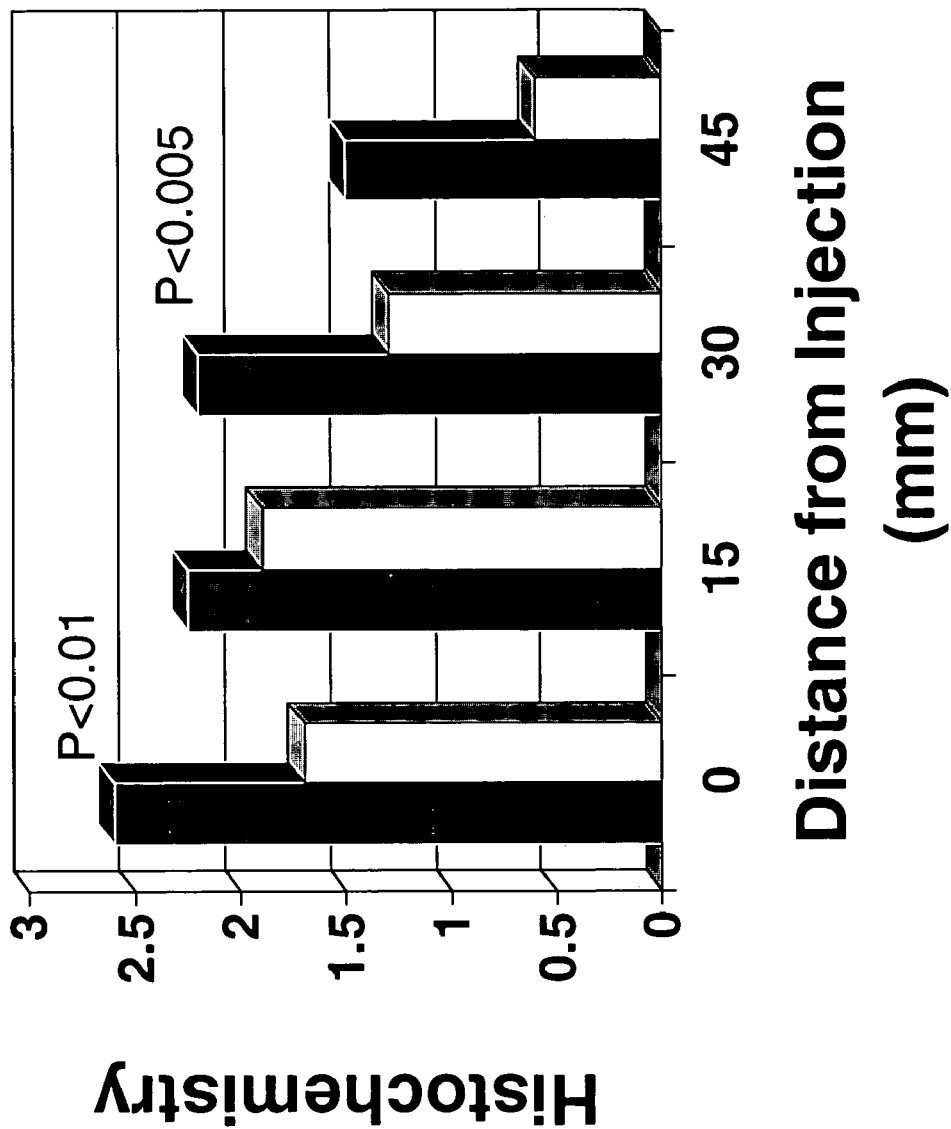
FIG. 2 depicts the denervation potency of two botulinum toxin preparations as determined by histochemical methods (acetylcholinesterase staining).

In animal models, the potency of a *botulinum* toxin preparation may be determined by measuring the extent of denervation produced when a preparation is administered to a muscle. The longissimus dorsi muscle of New Zealand white rabbits are injected with *botulinum* toxin. Five weeks after administration of the *botulinum* toxin, the animals were sacrificed and denervation of the muscle a 0, 15, 30 and 45 mm from the injection site was determined by examining muscle-fiber variability (FIG. 1) and acetylcholinesterase activity histochemical staining (FIG. 2).

The longissimus dorsi muscle of twenty-eight (28) white New Zealand rabbits were injected with 5 $LD_{50}$ Units of a commercial preparation of BOTOX®. BOTOX® is a composition comprising *botulinum* toxin type A and 500 µg human serum albumin (HSA) per 100 $LD_{50}$ Units. Thirty-two (32) white New Zealand rabbits were injected with 5 $LD_{50}$ Units of a composition comprising *botulinum* toxin type A and 4,000 µg HSA per 100 $LD_{50}$ Units. Each toxin preparation was reconstituted with physiological saline. The point of injection was marked with a tattoo. The injections were made 5 to 8 mm deep directly into the muscle. A control animal was injected with the saline diluent. After five weeks, the animals were sacrificed, and muscle biopsies were taken 0, 15, 30, and 45 mm from the injection site transverse to the spine and in a direction parallel to the spine on the contralateral side. Tissues were analyzed for denervation based on muscle fiber variability using standard hematoxylin-eosin staining and acetylcholinesterase staining. The reversible neurogenic muscle fiber atrophy begins within about 10 to 14 days following injection. The general reduction in fiber diameter is often accompanied by a large degree of fiber size variability. The spreading of acetylcholinesterase staining (normally localized almost exclusively to the neuromuscular junction) over the sarcolemma of muscle fibers occurs over a 3 to 4 week period following injection and is useful for assessing the denervation activity of *botulinum* toxin preparations.

Biopsies were studied microscopically to compare muscle fiber variability with muscle fibers from a saline-injected control animal. Assessment of *botulinum* toxin activity within muscle was accomplished using a four point histologic grading scale (0=normal fiber variability; 1=low fiber variability; 3=moderate fiber variability; and 4=extensive fiber variability) based on the severity of muscle fiber neurogenic atrophy and extra-junctional acetylcholinesterase staining intensity. The results are depicted in FIG. 1.

The longissimus dorsi muscle of thirty-two (32) white New Zealand rabbits were injected with 5 $LD_{50}$ Units of a commercial preparation of BOTOX®. Nineteen (19) white New Zealand rabbits were injected with 5 $LD_{50}$ Units of a composition comprising *botulinum* toxin type A and 4,000 µg HSA per 100 $LD_{50}$ Units. Each toxin preparation was reconstituted with physiological saline. The point of injection was marked with a tattoo. The injections were made 5 to 8 mm deep directly into the muscle. A control animal was injected with the saline diluent. After five weeks, the animals were sacrificed, and muscle biopsies were taken 0, 15, 30, and 45 mm from the injection site transverse to the spine and in a direction parallel to the spine on the contralateral side. Tissues were analyzed for denervation based on acetylcholinesterase activity staining. Assessment of *botulinum* toxin activity within muscle was accomplished using a four point grading scale of acetylcholinesterase activity staining (0=no staining; 1=low intensity; 3=moderate intensity; and 4=high intensity). The results are depicted in FIG. 2.

I claim:

1. A pharmaceutical formulation comprising
   a therapeutically effective amount of *botulinum* neurotoxin type A having a specific activity between 100 and 250 $LD_{50}$ Units per nanogram *botulinum* toxin type A; and
   a human serum albumin present in an amount greater than 500 micrograms human serum albumin per 100 $LD_{50}$ Units neurotoxin,
   wherein said formulation has an increased clinical potency.

2. A method for muscle denervation comprising the step of administering a formulation of claim 1 to a human subject in need thereof in a therapeutically effective amount to produce local muscle denervation.

3. A method for treating neuromuscular diseases comprising the step of administering a formulation of claim 1 to a human subject in need thereof in a therapeutically effective amount to produce muscle weakness.

4. A method for treating pain comprising the step of administering a formulation of claim 1 to a human subject in need thereof in a therapeutically effective amount to reduce pain.

5. A method for cosmetically modifying soft-tissue features comprising the step of administering a formulation of claim 1 to a human subject in need thereof in a therapeutically effective amount to modify said features.

6. The method of claim 5, wherein the formulation is administered to the subject in a therapeutically effective amount to reduce rhytides.

7. A method for treating inflammation comprising the step of administering a formulation of claim 1 to a human subject in need thereof in a therapeutically effective amount to reduce inflammation.

8. A method of treating cutaneous disorders comprising the step of administering a formulation of claim 1 to a human subject in need thereof in a therapeutically effective amount to reduce a sebaceous or mucous secretion.

9. A method of producing a high-potency *botulinum* toxin formulation comprising the step of adding human serum albumin to *botulinum* neurotoxin type A in an amount greater than about 500 micrograms of a human serum albumin per 100 $LD_{50}$ Units of a *botulinum* neurotoxin type A having a specific activity between 100 and 250 $LD_{50}$ Units per nanogram *botulinum* toxin type A, wherein said formulation has an increased clinical potency.

10. The pharmaceutical formulation of claim 1, wherein the human serum albumin is present in an amount greater than 500 and less than 750 μg per 100 $LD_{50}$ Units neurotoxin.

11. The pharmaceutical formulation of claim 1, wherein the human serum albumin is present in an amount between 1000 and 1250 μg per 100 $LD_{50}$ Units neurotoxin.

12. The pharmaceutical formulation of claim 1, wherein the human serum albumin is present in an amount between 1250 and 1500 μg per 100 $LD_{50}$ Units neurotoxin.

13. The pharmaceutical formulation of claim 1, wherein the human serum albumin is present in an amount between 1500 and 1750 μg per 100 $LD_{50}$ Units neurotoxin.

14. The pharmaceutical formulation of claim 1, wherein the human serum albumin is present in an amount between 1750 and 2000 μg per 100 $LD_{50}$ Units neurotoxin.

15. The pharmaceutical formulation of claim 1, wherein the human serum albumin is present in an amount between 2000 and 2250 μg per 100 $LD_{50}$ Units neurotoxin.

16. The pharmaceutical formulation of claim 1, wherein the human serum albumin is present in an amount between 2250 and 2500 μg per 100 $LD_{50}$ Units neurotoxin.

17. The pharmaceutical formulation of claim 1, wherein the human serum albumin is present in an amount between 2500 and 2750 μg per 100 $LD_{50}$ Units neurotoxin.

18. The pharmaceutical formulation of claim 1, wherein the human serum albumin is present in an amount between 2750 and 3000 μg per 100 $LD_{50}$ Units neurotoxin.

19. The pharmaceutical formulation of claim 1, wherein the human serum albumin is present in an amount between 3000 and 3250 μg per 100 $LD_{50}$ Units neurotoxm.

20. The pharmaceutical formulation of claim 1, wherein the human serum albumin is present in an amount between 3250 and 3500 μg per 100 $LD_{50}$ Units neurotoxin.

21. The pharmaceutical formulation of claim 1, wherein the human serum albumin is present in an amount between 3500 and 3750 μg per 100 $LD_{50}$ Units neurotoxin.

22. The pharmaceutical formulation of claim 1, wherein the human serum albumin is present in an amount between 4750 and 5000 μg per 100 $LD_{50}$ Units neurotoxin.

23. The pharmaceutical formulation of claim 1, wherein the human serum albumin is present in an amount between 5000 and 5250 μg per 100 $LD_{50}$ Units neurotoxin.

24. The pharmaceutical formulation of claim 1, wherein the human serum albumin is present in an amount between 5250 and 5500 μg per 100 $LD_{50}$ Units neurotoxin.

25. The pharmaceutical formulation of claim 1, wherein the human serum albumin is present in an amount between 5500 and 5750 μg per 100 $LD_{50}$ Units neurotoxin.

26. The pharmaceutical formulation of claim 1, wherein the human serum albumin is present in an amount between 5750 and 6000 μg per 100 $LD_{50}$ Units neurotoxin.

27. The pharmaceutical formulation of claim 1, wherein the human serum albumin is present in an amount between 6000 and 6250 μg per 100 $LD_{50}$ Units neurotoxin.

28. The pharmaceutical formulation of claim 1, wherein the human serum albumin is present in an amount between 6250 and 6500 μg per 100 $LD_{50}$ Units neurotoxin.

29. The pharmaceutical formulation of claim 1, wherein the human serum albumin is present in an amount between 6500 and 6750 μg per 100 $LD_{50}$ Units neurotoxin.

30. The pharmaceutical formulation of claim 1, wherein the human serum albumin is present in an amount between 6750 and 7000 μg per 100 $LD_{50}$ Units neurotoxin.

31. The pharmaceutical formulation of claim 1, wherein the human serum albumin is present in an amount between 7000 and 7500 μg per 100 $LD_{50}$ Units neurotoxin.

32. The pharmaceutical formulation of claim 1, wherein the human serum albumin is present in an amount between 7500 and 7750 μg per 100 $LD_{50}$ Units neurotoxin.

33. The pharmaceutical formulation of claim 1, wherein the human serum albumin is present in an amount between 7750 and 8000 μg per 100 $LD_{50}$ Units neurotoxin.

34. The pharmaceutical formulation of claim 1, wherein the human serum albumin is present in an amount between 8000 and 8250 μg per 100 $LD_{50}$ Units neurotoxin.

35. The pharmaceutical formulation of claim 1, wherein the human serum albumin is present in an amount between 8250 and 8500 μg per 100 $LD_{50}$ Units neurotoxin.

36. The pharmaceutical formulation of claim 1, wherein the human serum albumin is present in an amount between 8500 and 8750 μg per 100 $LD_{50}$ Units neurotoxin.

37. The pharmaceutical formulation of claim 1, wherein the human serum albumin is present in an amount between 8750 and 9000 μg per 100 $LD_{50}$ Units neurotoxin.

38. The pharmaceutical formulation of claim 1, wherein the human serum albumin is present in an amount between 9000 and 9250 μg per 100 $LD_{50}$ Units neurotoxin.

39. The pharmaceutical formulation of claim 1, wherein the human serum albumin is present in an amount between 9250 and 9500 μg per 100 $LD_{50}$ Units neurotoxin.

40. The pharmaceutical formulation of claim 1, wherein the human serum albumin is present in an amount between 9500 and 9750 μg per 100 $LD_{50}$ Units neurotoxin.

41. A method of treating cervical dystonia in a human patient comprising the step of injecting between 15 to 150 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation produces muscle weakness.

42. A method of treating blepharospasm in a human patient comprising the step of injecting between 2.5 to 45 picograms *botulinum* toxin type A per injection cycle of a pharmaceutical formulation comprising said *botulinum* toxin to said human patient, wherein administration of said formulation produces muscle weakness.

43. A method of treating blepharospasm in a human patient comprising the step of injecting between 2 to 20 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation produces muscle weakness.

44. A method of treating hyperhydrosis in a human patient comprising the step of injecting between 0.5 to 50 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces sweating.

45. A method of treating migraine headache in a human patient comprising the step of injecting between 0.5 to 50 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces migraine headache pain.

46. A method of treating strabismus in a human patient comprising the step of injecting between 2.5 to 45 picograms *botulinum* toxin type A per injection cycle of a pharmaceutical formulation comprising said *botulinum* toxin to said human patient, wherein administration of said formulation reduces symptoms of strabismus.

47. A method of treating strabismus in a human patient comprising the step of injecting between 4 to 40 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces symptoms of strabismus.

48. A method of treating hyperactive bladder in a human patient comprising the step of injecting between 4 to 40 $LD_{50}$ Units, having a specific activity between 100 and 250 $LD_{50}$ Units per nanogram *botulinum* toxin type A, *botulinum* toxin type A per injection cycle of a pharmaceutical formulation comprising said *botulinum* toxin to said human patient, wherein administration of said formulation reduces urination frequency.

49. A method of treating muscle spasticity in a human patient comprising the step of injecting between 20 to 200 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation produces muscle weakness.

50. A method of treating hemifacial spasm in a human patient comprising the step of injecting between 1.5 to 15 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation produces muscle weakness.

51. A method of myofascial pain in a human patient comprising the step of injecting between 5 to 100 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces myofascial pain.

52. A method of treating facial pain in a human patient comprising the step of injecting between 4 to 40 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces facial pain.

53. A method of treating inflammation in a human patient comprising the step of injecting between 1 to 20 picograms *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces inflammation.

54. A method of treating inflammation in a human patient comprising the step of injecting between 5 to 75 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces inflammation.

55. A method of treating blepharitis in a human patient comprising the step of injecting between 1 to 10 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces inflammation.

56. A method of treating scoliosis in a human patient comprising the step of injecting between 30 to 300 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation improves posture.

57. A method of treating scoliosis in a human patient comprising the step of injecting between 30 to 300 $LD_{50}$ Units *botulinum* toxin type A per injection cycle of the pharmaceutical formulation of claim 1 comprising said *botulinum* toxin to said human patient, wherein administration of said formulation improves posture.

58. A method of treating lower back pain in a human patient comprising the step of injecting between 15 to 150 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces pain.

59. A method of treating scleroderma in a human patient comprising the step of injecting between 30 to 300 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces a symptom of scleroderma.

60. A method of treating scleroderma in a human patient comprising the step of injecting between 30 to 300 $LD_{50}$ Units *botulinum* toxin type A per injection cycle of a pharmaceutical formulation comprising said *botulinum* toxin to said human patient, wherein administration of said formulation reduces a symptom of scleroderma.

61. A method of treating asthma and hayfever in a human patient comprising the step of injecting between 5 to 50 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces inflammation.

62. A method of treating prostatitis in a human patient comprising the step of injecting between 10 to 100 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces inflammation.

63. A method of treating tension headache in a human patient comprising the step of injecting between 5 to 50 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces pain.

64. A method of treating facial rhytides in a human patient comprising the step of injecting between 2 to 20 $LD_{50}$ Units *botulinum* toxin type A, having a specific activity between 100 and 250 $LD_{50}$ Units per nanogram *botulinum* toxin type A, per injection cycle of a pharmaceutical formulation comprising said *botulinum* toxin to said human patient, wherein administration of said formulation reduces facial lines.

65. The pharmaceutical formulation of claim 1, wherein the human serum albumin is present in an amount between 750 and 1000 μg per 100 $LD_{50}$ Units neurotoxin.

66. The pharmaceutical formulation of claim 1, wherein the human serum albumin is present in an amount between 3750 and 4000 μg per 100 $LD_{50}$ Units neurotoxin.

67. The pharmaceutical formulation of claim 1, wherein the human serum albumin is present in an amount between 4000 and 4250 μg per 100 $LD_{50}$ Units neurotoxin.

68. The pharmaceutical formulation of claim 1, wherein the human serum albumin is present in an amount between 4250 and 4500 μg per 100 $LD_{50}$ Units neurotoxin.

69. The pharmaceutical formulation of claim 1, wherein the human serum albumin is present in an amount between 4500 and 4750 μg per 100 $LD_{50}$ Units neurotoxin.

70. The method of claim 9, wherein the human serum albumin is added in an amount greater than 500 and less than 750 μg per 100 $LD_{50}$ Units neurotoxin.

71. The method of claim 9, wherein the human serum albumin is added in an amount between 750 and 1000 μg per 100 $LD_{50}$ Units neurotoxin.

72. The method of claim 9, wherein the human serum albumin is added in an amount between 1000 and 1250 μg per 100 $LD_{50}$ Units neurotoxin.

73. The method of claim 9, wherein the human serum albumin is added in an amount between 1250 and 1500 μg per 100 $LD_{50}$ Units neurotoxin.

74. The method of claim 9, wherein the human serum albumin is added in an amount between 1500 and 1750 μg per 100 $LD_{50}$ Units neurotoxin.

75. The method of claim 9, wherein the human serum albumin is added in an amount between 1750 and 2000 μg per 100 $LD_{50}$ Units neurotoxin.

76. The method of claim 9, wherein the human serum albumin is added in an amount between 2000 and 2250 μg per 100 $LD_{50}$ Units neurotoxin.

77. The method of claim 9, wherein the human serum albumin is added in an amount between 2250 and 2500 μg per 100 $LD_{50}$ Units neurotoxin.

78. The method of claim 9, wherein the human serum albumin is added in an amount between 2500 and 2750 μg per 100 $LD_{50}$ Units neurotoxin.

79. The method of claim 9, wherein the human serum albumin is added in an amount between 2750 and 3000 μg per 100 $LD_{50}$ Units neurotoxin.

80. The method of claim 9, wherein the human serum albumin is added in an amount between 3000 and 3250 μg per 100 $LD_{50}$ Units neurotoxin.

81. The method of claim 9, wherein the human serum albumin is added in an amount between 3250 and 3500 μg per 100 $LD_{50}$ Units neurotoxin.

82. The method of claim 9, wherein the human serum albumin is added in an amount between 3500 and 3750 μg per 100 $LD_{50}$ Units neurotoxin.

83. The method of claim 9, wherein the human serum albumin is added in an amount between 3750 and 4000 μg per 100 $LD_{50}$ Units neurotoxin.

84. The method of claim 9, wherein the human serum albumin is added in an amount between 4000 and 4250 μg per 100 $LD_{50}$ Units neurotoxin.

85. The method of claim 9, wherein the human serum albumin is added in an amount between 6250 and 6500 μg per 100 $LD_{50}$ Units neurotoxin.

86. The method of claim 9, wherein the human serum albumin is added in an amount between 6500 and 6750 μg per 100 $LD_{50}$ Units neurotoxin.

87. The method of claim 9, wherein the human serum albumin is added in an amount between 6750 and 7000 μg per 100 $LD_{50}$ Units neurotoxin.

88. The method of claim 9, wherein the human serum albumin is added in an amount between 4250 and 4500 μg per 100 $LD_{50}$ Units neurotoxin.

89. The method of claim 9, wherein the human serum albumin is added in an amount between 4500 and 4750 μg per 100 $LD_{50}$ Units neurotoxin.

90. The method of claim 9, wherein the human serum albumin is added in an amount between 4750 and 5000 μg per 100 $LD_{50}$ Units neurotoxin.

91. The method of claim 9, wherein the human serum albumin is added in an amount between 5000 and 5250 μg per 100 $LD_{50}$ Units neurotoxin.

92. The method of claim 9, wherein the human serum albumin is added in an amount between 5250 and 5500 μg per 100 $LD_{50}$ Units neurotoxin.

93. The method of claim 9, wherein the human serum albumin is added in an amount between 5500 and 5750 μg per 100 $LD_{50}$ Units neurotoxin.

94. The method of claim 9, wherein the human serum albumin is added in an amount between 5750 and 6000 μg per 100 $LD_{50}$ Units neurotoxin.

95. The method of claim 9, wherein the human serum albumin is added in an amount between 6000 and 6250 μg per 100 $LD_{50}$ Units neurotoxin.

96. The method of claim 9, wherein the human serum albumin is added in an amount between 7000 and 7500 μg per 100 $LD_{50}$ Units neurotoxin.

97. The method of claim 9, wherein the human serum albumin is added in an amount between 7500 and 7750 μg per 100 $LD_{50}$ Units neurotoxin.

98. The method of claim 9, wherein the human serum albumin is added in an amount between 7750 and 8000 μg per 100 $LD_{50}$ Units neurotoxin.

99. The method of claim 9, wherein the human serum albumin is added in an amount between 8000 and 8250 μg per 100 $LD_{50}$ Units neurotoxin.

100. The method of claim 9, wherein the human serum albumin is added in an amount between 8250 and 8500 μg per 100 $LD_{50}$ Units neurotoxin.

101. The method of claim 9, wherein the human serum albumin is added in an amount between 8500 and 8750 μg per 100 $LD_{50}$ Units neurotoxin.

102. The method of claim 9, wherein the human serum albumin is added in an amount between 8750 and 9000 μg per 100 $LD_{50}$ Units neurotoxin.

103. The method of claim 9, wherein the human serum albumin is added in an amount between 9000 and 9250 μg per 100 $LD_{50}$ Units neurotoxin.

104. The method of claim 9, wherein the human serum albumin is added in an amount between 9250 and 9500 μg per 100 $LD_{50}$ Units neurotoxin.

105. The method of claim 9, wherein the human serum albumin is added in an amount between 9500 and 9750 μg per 100 $LD_{50}$ Units neurotoxin.

106. The method of claim 9, wherein the human serum albumin is added in an amount between 9750 and 10,000 μg per 100 $LD_{50}$ Units neurotoxin.

107. The pharmaceutical formulation of claim 1, wherein the human serum albumin is present in an amount between 9750 and 10,000 μg per 100 $LD_{50}$ Units neurotoxin.

* * * * *